(12) United States Patent
Leonard et al.

(10) Patent No.: US 12,091,668 B2
(45) Date of Patent: Sep. 17, 2024

(54) PLATFORM OF COMPOSABLE MAMMALIAN ELEMENTS OF TRANSCRIPTION (COMET)

(71) Applicant: Northwestern University, Evanston, IL (US)

(72) Inventors: Joshua N. Leonard, Wilmette, IL (US); Patrick S. Donahue, Chicago, IL (US)

(73) Assignee: Northwestern University, Evanston, IL (US)

( * ) Notice: Subject to any disclaimer, the term of this patent is extended or adjusted under 35 U.S.C. 154(b) by 1245 days.

(21) Appl. No.: 16/496,140

(22) PCT Filed: Mar. 23, 2018

(86) PCT No.: PCT/US2018/023989
§ 371 (c)(1),
(2) Date: Sep. 20, 2019

(87) PCT Pub. No.: WO2018/175865
PCT Pub. Date: Sep. 27, 2018

(65) Prior Publication Data
US 2020/0024608 A1    Jan. 23, 2020

Related U.S. Application Data

(60) Provisional application No. 62/475,597, filed on Mar. 23, 2017.

(51) Int. Cl.
*C12N 15/63* (2006.01)
*C12N 15/85* (2006.01)

(52) U.S. Cl.
CPC .......... *C12N 15/635* (2013.01); *C12N 15/85* (2013.01); *C12N 2830/34* (2013.01)

(58) Field of Classification Search
None
See application file for complete search history.

(56) References Cited

U.S. PATENT DOCUMENTS

| 9,732,392 B2 * | 8/2017 | Leonard | G01N 33/566 |
| 2003/0049842 A1 * | 3/2003 | Baron | A61P 29/00 |
| | | | 435/456 |

FOREIGN PATENT DOCUMENTS

| WO | WO 96/20951 A1 | 7/1996 |
| WO | WO 2013/022739 A1 | 2/2013 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
International Search Report and Written Opinion dated Jun. 21, 2018, in PCT/US2018/023989.
Li et al., "Activation domains for controlling plant gene expression using designed transcription factors," Plant Biotechnology Journal, 2013, 11(6):671-680.

\* cited by examiner

*Primary Examiner* — Christian L Fronda
(74) *Attorney, Agent, or Firm* — Foley & Lardner LLP

(57) ABSTRACT

Disclosed are systems and methods that include or utilize composable mammalian elements of transcription (COMET) including engineered recombinant proteins that regulate transcription and engineered DNA promoter sequences that are regulated by the engineered recombinant proteins. The elements may be composed to form logic gates, gene expression cascades and programs, and cell-based biosensors.

20 Claims, 57 Drawing Sheets

B

PLATFORM OF COMPOSABLE MAMMALIAN ELEMENTS OF TRANSCRIPTION (COMET)

CROSS-REFERENCE TO RELATED PATENT APPLICATIONS

The present application claims the benefit of priority under 35 U.S.C. 119(e) to U.S. Provisional Patent Application No. 62/475,597, filed on Mar. 23, 2017, the content of which is incorporated herein by reference in its entirety.

BACKGROUND

The present invention is related to systems and methods for engineering biological reporting and gene expression systems. The systems and methods include or utilize composable mammalian elements of transcription (COMET) including engineered recombinant proteins that regulate transcription and engineered DNA promoter sequences that are regulated by the engineered recombinant proteins.

Mammalian cells can be programmed for numerous applications, ranging from customized cell-based therapeutics to tools for probing fundamental biological questions. To date, however, the tools available for composing such biological programs are limited in number, and tuning the performance of such biological parts is challenging, limiting the scope of applications that can be pursued. Here, we describe tools for composing such biological programs referred to as composable mammalian elements of transcription (COMET).

SUMMARY

Disclosed are systems and methods that include or utilize composable mammalian elements of transcription (COMET) including engineered recombinant proteins that regulate transcription and engineered DNA promoter sequences that are regulated by the engineered recombinant proteins. The elements may be composed to form logic gates, gene expression cascades and programs, and cell-based biosensors.

The disclosed systems and methods may be viewed as modular transcription systems and methods, respectively. The disclosed systems may include and the disclosed methods may utilize engineered proteins, which may include but are not limited to fusion proteins including heterologous domains. In some embodiments, the engineered proteins may be described as: (i) an engineered protein that activates gene expression, the engineered protein comprising a DNA binding domain and a transcription activator domain; (ii) an engineered protein that inhibits gene expression, the engineered protein comprising a DNA binding domain and optionally comprising a transcription inhibitor domain; and (iii) a combination of two engineered proteins comprising a first engineered protein comprising a DNA binding domain fused to a dimerization domain, and a second engineered protein comprising a transcription regulator domain fused to a dimerization domain, wherein the dimerization domains of the two engineered proteins dimerize in the presence of a ligand to which the dimerization domains of the two engineered proteins bind. In some embodiments, of the disclosed systems and methods the engineered protein of (ii) may inhibit activation of transcription by the engineered protein of (i).

The disclosed engineered proteins may include DNA binding domains. Suitable DNA binding domains may include, but are not limited to zinc fingers (e.g., 2, 3, 4 or more zinc fingers).

The disclosed engineered proteins may include a transcription activator domain. Suitable transcription activator domains may include, but are not limited to, a domain from a transcription activator selected from the group consisting of Herpes simplex virus protein 16 (VP16), a synthetic tetramer of VP16 (VP64), nuclear factor (NF) kappa-B (p65), heat shock transcription factor 1 (HSF1), and replication and transcription activator (RTA) of the gamma-herpesvirus family The disclosed systems may include and the disclosed methods may utilize engineered DNA sequences including engineered expression vectors. The engineered vectors may include a minimal promoter and one or more DNA binding sites for the DNA binding domains of the engineered proteins of (i), (ii), and/or (iii) described above. Optionally, the engineered expression vectors may include a gene of interest that may be expressed from the minimal promoter, for example, in the presence of a transcription activator bound to the one or more DNA binding sites.

The disclosed systems may be configured to utilize multiple different engineered proteins and multiple different DNA binding sites and/or engineered expression vectors. The disclosed systems may be configured as logic gates wherein expression from an engineered expression vector requires binding to multiple DNA binding sites by multiple different engineered proteins.

The disclosed systems may be configured to effect a cascade or program of expression. In some embodiments, the disclosed systems include: (a) a first engineered protein that activates gene expression, the first engineered protein comprising a first DNA binding domain and a transcription activator domain; (b) a first engineered expression vector comprising a minimal promoter and first DNA binding sites for the first DNA binding domain of the first engineered protein, and a first gene of interest that is expressed from the minimal promoter, wherein the gene of interest encodes a second engineered protein, the second engineered protein comprising a second DNA binding domain and a transcription activator domain; and (c) a second engineered expression vector comprising a minimal promoter and second DNA binding sites for the second DNA binding domain of the engineered protein, and a second gene of interest that is expressed from the minimal promoter, wherein the second gene of interest encodes a detectable reporter protein. In the disclosed systems that are configured to effect a cascade or program of expression as such, the first engineered protein may increase expression from the first engineered expression vector and the second engineered protein, which is expressed from the first engineered expression vector, may increases expression from the second engineered vector.

The engineered proteins described herein may be present in an exogenous extracellular sensor. In some embodiments, the extracellular sensor comprises: (a) a ligand binding domain, (b) a transmembrane domain, (c) a protease cleavage site, and (d) an engineered protein as contemplated herein.

The exogenous extracellular sensor comprising the engineered protein may be present in an exogenous extracellular sensor system for detecting an extracellular ligand. In some embodiments, the exogenous extracellular sensor systems contemplated herein include (i) a first exogenous extracellular sensor comprising: (a) a ligand binding domain, (b) a transmembrane domain, (c) a protease cleavage site, and (d) an engineered protein domain comprising a DNA binding domain and a transcription activator domain; (ii) a second exogenous extracellular sensor comprising (a) a ligand binding domain, (b) a transmembrane domain, and (c) a protease domain, and optionally (iii) an engineered expression vector comprising a minimal promoter and one or more DNA binding sites for the DNA binding domains of the first exogenous extracellular sensor, and optionally a gene of interest that is expressed from the minimal promoter.

In the disclosed exogenous extracellular sensor systems, the ligand binding domain of the first exogenous extracellular sensor and the ligand binding domain of the second exogenous extracellular sensor bind to the same ligand to form a tertiary complex, and the protease domain of the second exogenous extracellular sensor cleaves the protease cleavage site of the first exogenous extracellular sensor to release the engineered protein domain comprising the DNA binding domain and transcription activator domain. The engineered protein domain then may bind to the DNA binding sites of the engineered expression vector and increase expression from the minimal promoter. A reporter gene may be present in the engineered expression vector downstream of the minimal promoter, and expression of the reporter gene can be detected to indicate that the extracellular ligand is present.

DETAILED DESCRIPTION

Figure 1:
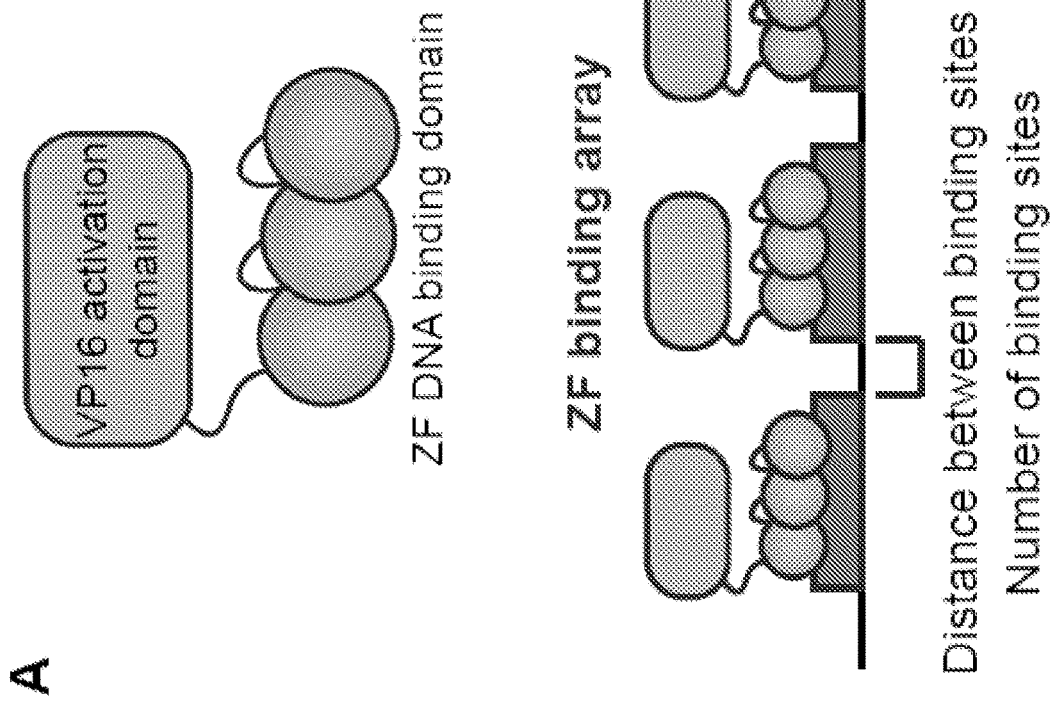
FIG. 1. Investigation of promoter design rules in mammalian cells. (A) Schematic showing the modular ZFa. Diagram of engineered promoter and reporter constructs depicting the tunable parameters. (C-F) Evaluation of ZF and promoter architectures design choices in mammalian cells. Spaced promoters have at least 16 bp between each binding site and compact promoters have exactly 6 bp. Experiments were conducted in biologic triplicate, and the mean fluorescence intensity (MFI) of single, transfected cells was background-subtracted and converted to MEFLs as described in Methods. Error bars represent the standard error of the mean (S.E.M.). Each panel is representative of one experiment.
Figure 1:
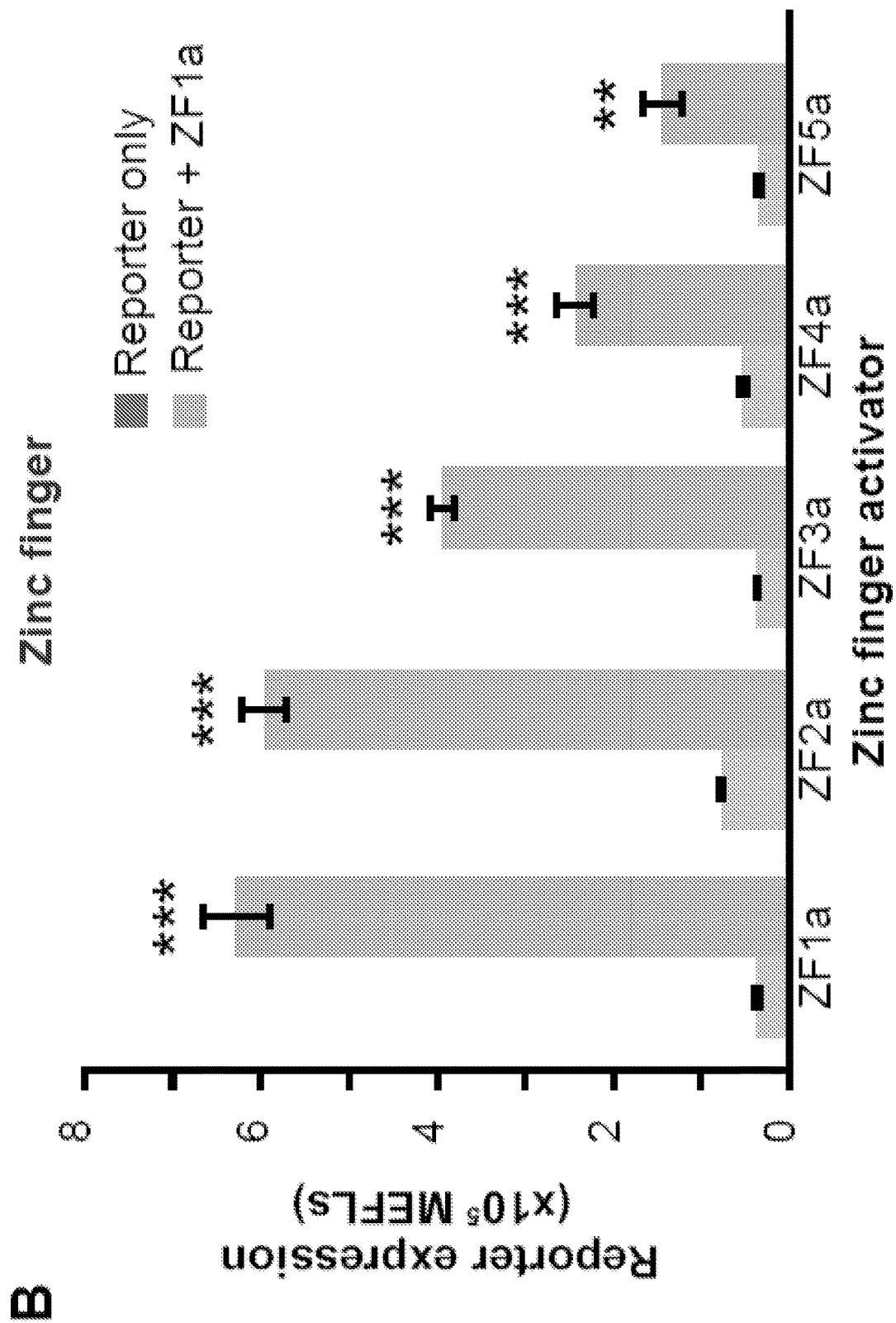
Figure 1:
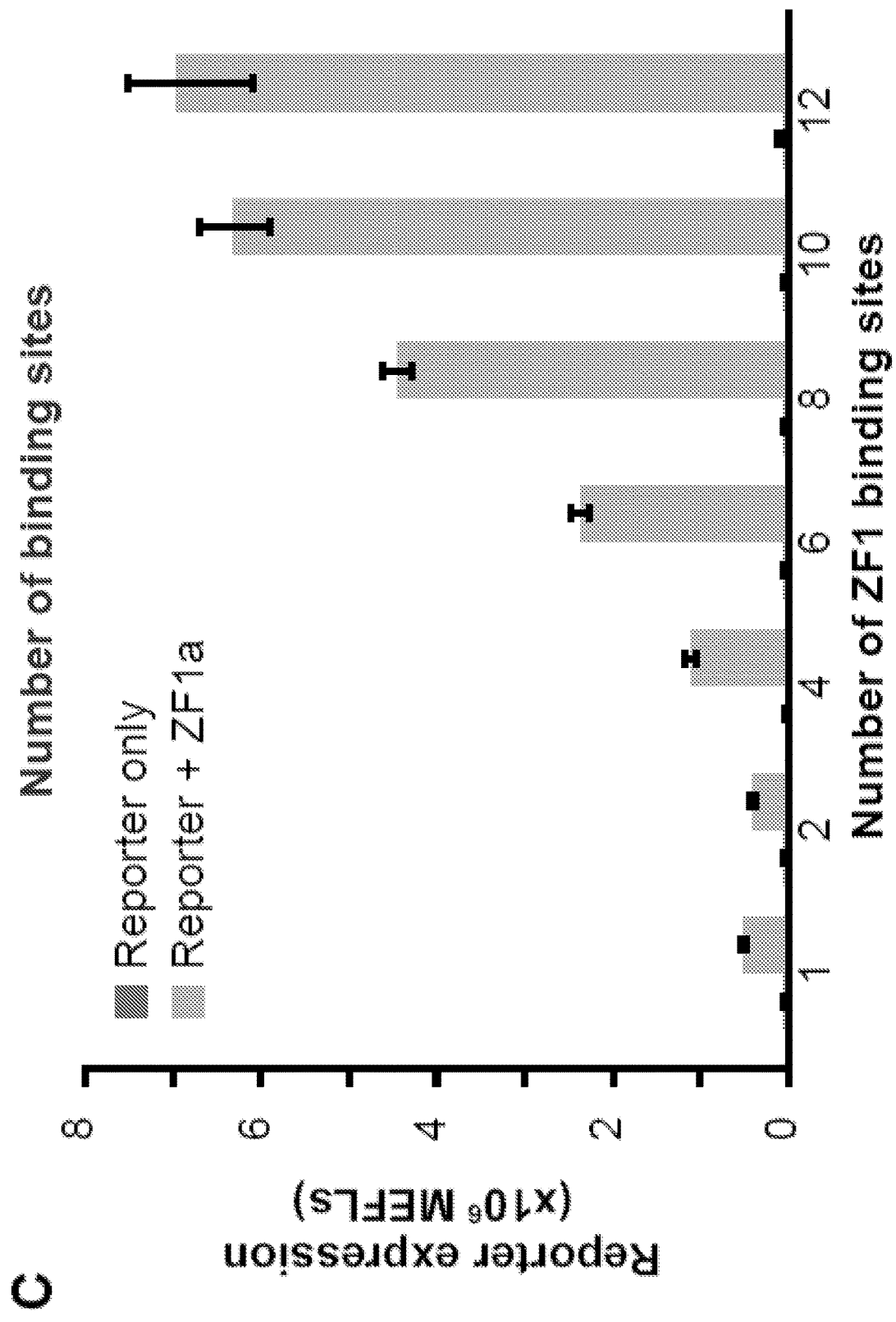
Figure 1:
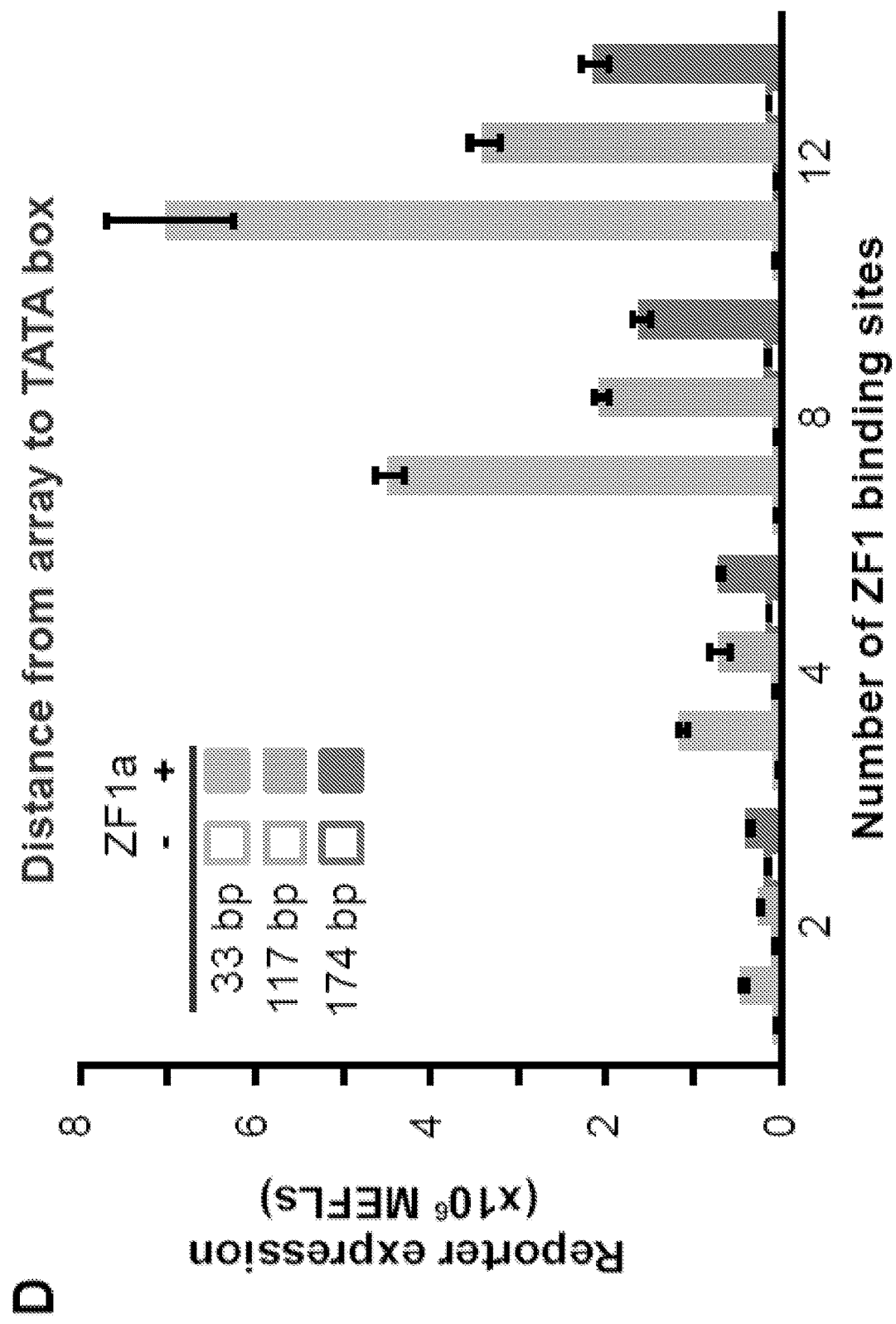
Figure 1:
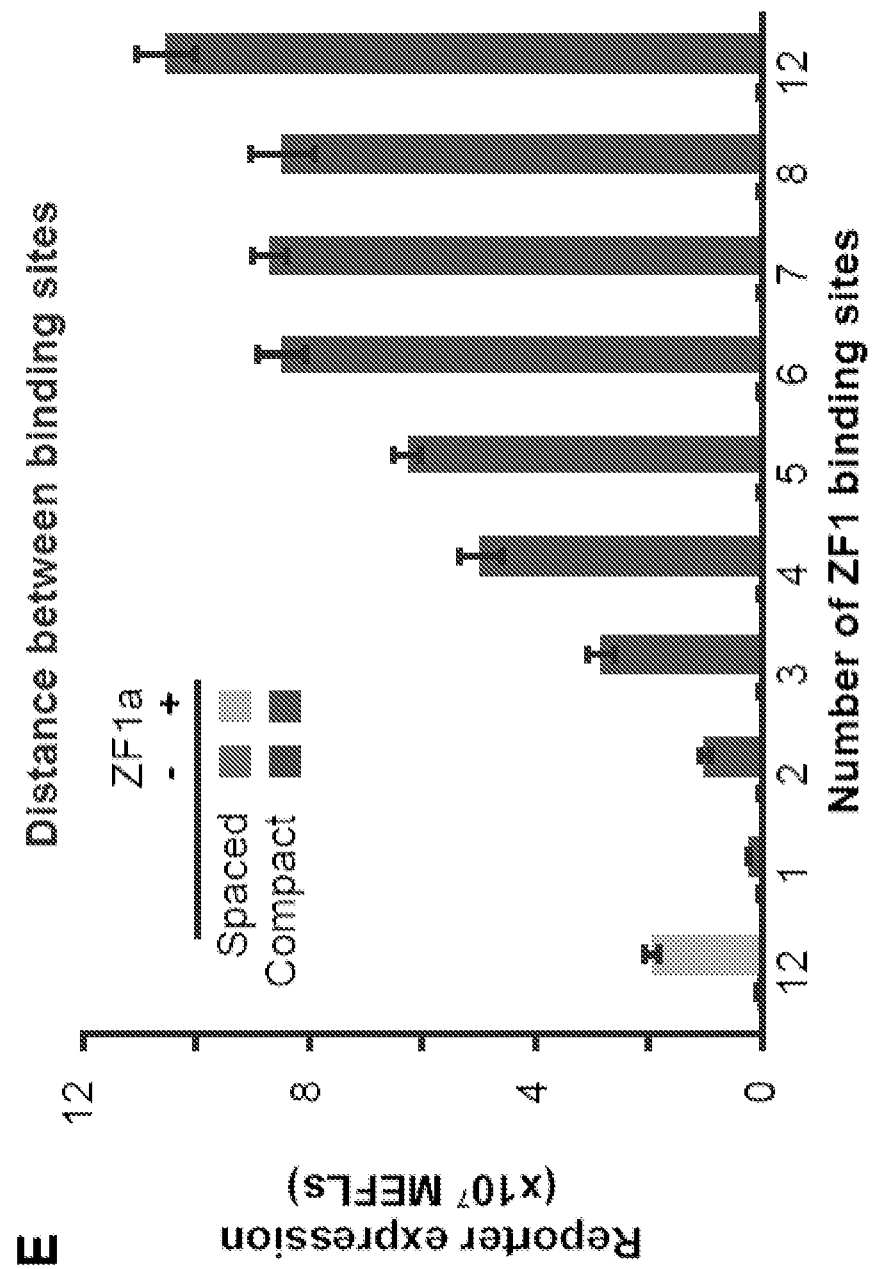

The present invention is described herein using several definitions, as set forth below and throughout the application.

Unless otherwise specified or indicated by context, the terms "a", "an", and "the" mean "one or more." For example, "a system," "a method," "a protein," "a vector," "a domain," and "a binding site" should be interpreted to mean "one or more systems," "one or more methods," "one or more proteins," "one or more vectors," "one or more domains," and "one or more binding sites," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned sing a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

Also disclosed herein are polynucleotides, for example polynucleotide sequences that encode proteins or polypeptides as disclosed herein. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, E. coli, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

"Transformation" or "transfection" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refers to a recombinant nucleic acid that has been engineered to express a heterologous polypeptide (e.g., the fusion proteins disclosed herein). The recombinant nucleic acid typically includes cis-acting elements for expression of the heterologous polypeptide.

Any of the conventional vectors used for expression in eukaryotic cells may be used for directly introducing DNA into a subject. Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter, SV40 later promoter, metallothionein promoter, human cytomegalovirus promoter, murine mammary tumor virus promoter, and Rous sarcoma virus promoter. Expression vectors as contemplated herein may include eukaryotic or prokaryotic control sequences that modulate expression of a heterologous protein (e.g. the fusion protein disclosed herein).

The presently disclosed methods may include delivering one or more polynucleotides, such as or one or more vectors as described herein and/or one or proteins transcribed therefrom, to a host cell. Further contemplated are host cells produced by such methods, and organisms (such as animals, plants, or fungi) comprising or produced from such cells. Conventional viral and non-viral based gene transfer methods can be used to introduce nucleic acids in mammalian cells or target tissues. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell.

In the methods contemplated herein, a host cell may be transiently or non-transiently transfected (i.e., stably transfected) with one or more vectors described herein. In some embodiments, a cell is transfected as it naturally occurs in a subject (i.e., in situ). In some embodiments, a cell that is transfected is taken from a subject (i.e., explanted). In some embodiments, the cell is derived from cells taken from a subject, such as a cell line. Suitable cells may include stem cells (e.g., embryonic stem cells and pluripotent stem cells). A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors, or transfection with RNA), and modified through the activity of a complex, in order to establish a new cell line comprising cells containing the modification but lacking any other exogenous sequence.

A Platform Comprising Composable Mammalian Elements of Transcription (COMET)

The technical field of the invention relates to biological engineering in mammalian synthetic biology. Mammalian cells can be programmed for numerous applications, ranging from customized cell-based therapeutics to tools for probing fundamental biological questions. To date, however, the tools available for composing such biological programs are limited in number, and tuning the performance of such biological parts is challenging, limiting the scope of applications that can be pursued. To meet this need, we developed the Composable Mammalian Elements of Transcription (COMET) tootlkit. COMET comprises a suite of engineered proteins that regulate gene expression, including both activation and suppression of gene expression, and engineered DNA sequences that are regulated by these engineered proteins. Both the proteins and the cognate DNA sequences are modular in design, enabling one to tune the quantitative performance of the system and to multiplex these elements to build sophisticated, customized, cellular functions. We anticipate that the COMET toolkit will be of substantial use for applications in fundamental research, biotechnology, and medicine.

Applications for the disclosed technology may include, but are not limited to: (i) engineered cell-based therapies for cancer, auto-immune disease, regenerative medicine, and many other diseases; (ii) investigating fundamental biological questions (research), for example by expressing transgenes in mammalian cells at various levels or only under certain conditions; and (c) control of gene expression in biotechnology, for example production of recombinant proteins in mammalian cells Advantages of the disclosed technology may include, but are not limited to: (i) the disclosed technology comprises a set of comparable transcription factors which recognize orthogonal binding sites and can therefore be multiplexed and used in combination to perform different tasks within a single cell; and (ii) many different parameters are readily tunable in the disclosed technology using either design-driven or experimentally identified variations in the engineered proteins and/or DNA sequences of the disclosed technology.

The disclosed COMET technology may be integrated with previous described technology related to the use of Modular Expression Sensor Architecture (MESA). MESA technology is known in the art. (See e.g., Rachel M. Dudek, Ph.D. Dissertation entitled "Engineering Multiparametric Evaluation of Environmental Cues by Mammalian Cell-based Devices," Northwestern University, August 2015; Daringer et al., "Modular Extracellular Sensor Architecture for Engineering Mammalian Cell-based Devices," Nichole M. Daringer, Rachel M. Dudek, Kelly A. Schwarz, and Josh N. Leonard, ACS Synth. Biol. 2014, 3, 892-902, published Feb. 25, 2014; and international publication WO 2013/022739, published on Feb. 14, 2013; the contents of which are incorporated herein by reference in their entireties).

MESA systems typically include a pair of extracellular receptors where both receptors of the pair contain a ligand binding domain and transmembrane domain, and one receptor contains a protease cleavage site and a functional domain (e.g., transcription regulator such as a transcription regulator that promotes transcription or a transcription regulator that inhibits transcription) and the other receptor contains a protease domain. As used herein, a transcription regulator may include a transcription factor that promotes transcription (e.g., by recruiting additional cellular components for transcription) and/or a transcription inhibitor or transcription repressor). In some embodiments of the disclosed subject matter, a MESA receptor may comprise a transcription factor or transcription inhibitor as described herein for use in the COMET technology as described herein.

The disclosed COMET technology may be integrated with previous technology related to the use of TANGO assays. (See Barnea et al., "The genetic design of signaling cascades to record receptor activation," Proc Natl Acad Sci USA. 2008 Jan. 8; 105(1):64-69; the content of which is incorporated herein by reference in its entirety). In some embodiments of the disclosed subject matter, a TANGO assay and/or a receptor utilized in a TANGO assay may comprise a transcription factor or transcription inhibitor as described herein for use in the COMET technology as described herein.

The disclosed COMET technology may be integrated with previous technology related to the use of synNOTCH assays. (See Morsul et al., "Engineering Customized Cell Sensing and Response Behaviors Using Synthetic Notch Receptors," Cell. 2016 Feb. 11; 164(4): 780-791; the content of which is incorporated herein by reference in its entirety). In some embodiments of the disclosed subject matter, a synNOTCH pathway and/or a receptor utilized in a syn-NOTCH pathway may comprise or utilize a transcription factor or transcription inhibitor as described herein for use in the COMET technology as described herein.

ILLUSTRATIVE EMBODIMENTS

The following embodiments are illustrative and should not be interpreted to limit the scope of the claimed subject matter.

Embodiment 1. A modular transcription system comprising: (a) one or more engineered proteins selected from the group consisting of: an engineered protein that activates gene expression, the engineered protein comprising a DNA binding domain and a transcription activator domain; an engineered protein that inhibits gene expression, the engineered protein comprising a DNA binding domain and a transcription inhibitor domain; a combination of two engineered proteins comprising a first engineered protein comprising a DNA binding domain fused to a dimerization domain, and a second engineered protein comprising a transcription regulator domain fused to a dimerization domain, wherein the dimerization domains of the two engineered proteins dimerize in the presence of a ligand to which the dimerization domains of the two engineered proteins bind; and (b) one or more engineered expression vectors, the vectors comprising a minimal promoter and one or more DNA binding sites for the DNA binding domains of the engineered proteins of (i), (ii), and/or (iii), and optionally a gene of interest that is expressed from the minimal promoter.

Embodiment 2. The modular transcription system of embodiment 1 comprising the engineered protein of (i) and the engineered protein of (ii).

Embodiment 3. The modular transcription system of embodiment 1 or 2, wherein the DNA binding domain of the one or more engineered proteins of (i), (ii), and (iii) comprises one or more zinc fingers.

Embodiment 4. The modular transcription system of embodiment 3, wherein the DNA binding domain comprises 2, 3, or more zinc fingers.

Embodiment 5. The modular transcription system of any of the foregoing embodiments, wherein the engineered proteins are fusion proteins comprising heterologous domains.

Embodiment 6. The modular transcription system of any of the foregoing embodiments, wherein the transcription activator domain of the engineered protein of (i), (ii), and/or (iii) comprises a domain from a transcription activator selected from the group consisting of Herpes simplex virus protein 16 (VP16), a synthetic tetramer of VP16 (VP64), nuclear factor (NF) kappa-B (p65), heat shock transcription factor 1 (HSF1), and replication and transcription activator (RTA) of the gamma-herpesvirus family Embodiment 7. The modular transcription system of any of the foregoing embodiments, wherein the engineered protein of (ii) inhibits activation of transcription by the engineered protein of (i).

Embodiment 8. The modular transcription system of any of the foregoing embodiments, wherein the transcription regulator domain of the second engineered protein of the combination of engineered proteins of (iii) is a transcription activator domain optionally selected from the group consisting of Herpes simplex virus protein 16 (VP16), a synthetic tetramer of VP16 (VP64), nuclear factor (NF) kappa-B (p65), heat shock transcription factor 1 (HSF1), and replication and transcription activator (RTA) of the gamma-herpesvirus family Embodiment 9. The modular transcription system of any of the foregoing embodiments, comprising: (a) a first engineered protein that activates gene expression, the first engineered protein comprising a first DNA binding domain and a transcription activator domain; (b) a first engineered expression vector comprising a minimal promoter and first DNA binding sites for the first DNA binding domain of the first engineered protein, and a first gene of interest that is expressed from the minimal promoter, wherein the gene of interest encodes a second engineered protein, the second engineered protein comprising a second DNA binding domain and a transcription activator domain; and (c) a second engineered expression vector comprising a minimal promoter and second DNA binding sites for the second DNA binding domain of the engineered protein, and a second gene of interest that is expressed from the minimal promoter, wherein the second gene of interest encodes a detectable reporter protein; wherein the first engineered protein increases expression from the first engineered expression vector and the second engineered protein increases expression from the second engineered vector.

Embodiment 10. The modular transcription system of any of the foregoing embodiments wherein the engineered proteins of (i) or (ii) are present in an exogenous extracellular sensor.

Embodiment 11. The modular transcription system of embodiment 9, wherein the extracellular sensor comprises: (a) a ligand binding domain, (b) a transmembrane domain, (c) a protease cleavage site, and (d) the engineered protein of (i) or (ii).

Embodiment 12. An exogenous extracellular sensor system comprising: (i) a first exogenous extracellular sensor comprising: (a) a ligand binding domain, (b) a transmembrane domain, (c) a protease cleavage site, and (d) an engineered protein domain comprising a DNA binding domain and a transcription activator domain; (ii) a second exogenous extracellular sensor comprising (a) a ligand binding domain, (b) a transmembrane domain, and (c) a protease domain, and optionally (iii) an engineered expression vector comprising a minimal promoter and one or more DNA binding sites for the DNA binding domains of the first exogenous extracellular sensor, and optionally a gene of interest that is expressed from the minimal promoter; wherein: the ligand binding domain of the first exogenous extracellular sensor and the ligand binding domain of the second exogenous extracellular sensor bind to the same ligand to form a tertiary complex; the protease domain of the second exogenous extracellular sensor cleaves the protease cleavage site of the first exogenous extracellular sensor to release the engineered protein domain comprising the DNA binding domain and transcription activator domain; and the DNA binding domain of the engineered protein domain binds to the one or more DNA binding sites of the engineered expression vector and increases expression from the minimal promoter of the engineered expression vector.

EXAMPLES

The following Examples are illustrative and are not intended to limit the scope of the claimed subject matter.

A Platform Comprising Composable Mammalian Elements of Transcription (COMET)

Mammalian cells can be programmed for numerous applications, ranging from customized cell-based therapeutics to tools for probing fundamental biological questions. To date, however, the tools available for composing such biological programs are limited in number, and tuning the performance of such biological parts is challenging, limiting the scope of applications that can be pursued. To meet this need, we developed the Composable Mammalian Elements of Transcription (COMET) tool-kit. COMET comprises a suite of engineered proteins that regulate gene expression, including both activation and suppression of gene expression, and engineered DNA sequences that are regulated by these engineered proteins. Both the proteins and the cognate DNA sequences are modular in design, enabling one to tune the quantitative performance of the system and to multiplex these elements to build sophisticated, customized, cellular functions. We anticipate that the COMET tool-kit will be of substantial use for applications in fundamental research, biotechnology, and medicine.

Zinc Finger Activators, Number, and Positioning of Binding Sites. Each zinc finger activator (ZFa) comprises two domains: an activation domain (AD) and a DNA binding domain (See, e.g., FIG. 1A). The first domain includes previously well-characterized activation domains such as VP16, VP64, p65, HSF1, and RTA. The second domain is a DNA binding domain, such as a zinc finger (ZF) protein with three zinc finger DNA binding motifs (Khalil 2012). A short protein linker fuses the two domains. Each ZFa binds to a cognate sequence of DNA, bringing the AD near the DNA. The AD recruits the native cellular transcription machinery to transcribe a gene placed downstream of the ZF binding site(s) and under the control of a minimal promoter (Hansen et al, 2014). This results in expression of the gene downstream of the engineered promoter (FIG. 1A). Variables that affect expression from the minimal promoter include, but are not limited to: (i) the zinc finger of ZFa and its cognate binding sequence (see Khalil 2012); (ii) the distance between binding sites for the zinc finger of ZFa in the promoter, (ii) the number of binding sites for the zinc finger of ZFa in promoter, and (iii) the distance between the binding site or array of binding sites for the zinc finger of ZFa and the minimal promoter (e.g., TATA box of minimal promoter).

Various zinc fingers (ZF1, ZF2, ZF3, ZF4, and ZF5) were used to create corresponding ZFa's by fusing the zinc finger activators with the activation domain of VP16 (ZF1a, ZF2a, ZF3a, ZF4a, and ZF5a). (See Table 1).

TABLE 1

List of ZF used in this study. Numbers from Khalil et al. (Cell, 2012) are provided for reference. The 9-bp binding sequence of each ZF is listed.

| ZF Number | ZF Number (Khalil 2012) | Binding Sequence | Zinc Finger Residues | | |
|---|---|---|---|---|---|
| | | | Finger 1 | Finger 2 | Finger 3 |
| 1 | 43-8 | GAG TGA GGA | RQDRLDR | AKEHLAG | RRDNLNR |
| 2 | 37-12 | GAG GAC GTG | RNFILQR | DRANLRR | RHDQLTR |
| 3 | 158-2 | GTA GAT GGA | DKTKLRV | VRHNLTR | QSTSLQR |
| 4 | 97-4 | TTA TGG GAG | RQSNLSR | RNEHLVL | QKTGLRV |
| 5 | 92-1 | GAT GTA GCC | DSPTLRR | ARSSLVR | ERGNLTR |
| 6 | 150-4 | GTG TAG GGG | KGERLVR | RMDNLST | RKDALNR |

TABLE 1-continued

List of ZF used in this study. Numbers from Khalil et al. (Cell, 2012) are provided for reference. The 9-bp binding sequence of each ZF is listed.

| ZF Number | ZF Number (Khalil 2012) | Binding Sequence | Zinc Finger Residues | | |
|---|---|---|---|---|---|
| | | | Finger 1 | Finger 2 | Finger 3 |
| 7 | 172-5 | GGA GGG GCT | MKNTLTR | RQEHLVR | QKPHLSR |
| 8 | 173-3 | GAT GAA GCT | SAQALAR | QQTNLAR | VGSNLTR |
| 9 | 42-10 | GAC GCT GCT | TGQILDR | VAHSLKR | DPSNLRR |
| 10 | 13-6 | GAA GAT GGT | TNQKLEV | VRHNLQR | QHPNLTR |
| 11 | 36-4 | GAA GAC GCT | GRQALDR | DKANLTR | QRNNLGR |
| 12 | 62-1 | GCC GAA GAT | TGQRLRI | QNQNLAR | DKSVLAR |
| 13 | 21-16 | TTA GAA GTG | RNFILQR | QGGNLVR | QQTGLNV |
| 14 | 14-3 | GAC GAC GGC | APSKLDR | LGENLRR | DGGNLGR |
| 15 | 129-3 | GGG GAC GTC | TAAVLTR | DRANLTR | RIDKLGD |
| 16 | 54-8 | TGG GTG GCA | NKTDLGR | RRDMLRR | RMDHLAG |
| 17 | 55-1 | TGG GGT GCC | DESTLRR | MKHHLGR | RSDHLSL |
| 18 | 93-10 | TTT GTT GGC | APSKLKR | HKSSLTR | QRNALSG |
| 19 | 151-1 | GCA GGA GGT | IPNHLAR | QSAHLKR | QDVSLVR |

The ZFa's then were evaluated in an expression assay. (See FIG. 1B). Expression was highest for ZF1a which was selected for further testing. The number of binding sites for ZF1 in the synthetic promoter was then evaluated in an expression assay. (See FIG. 1C). Expression increased proportionally with an increase in the number of binding sites from 1 to 12. However, expression appeared to partially level-off at 10-12 binding sites. The distance of the array of binding sites from the TATA box also was evaluated in an expression assay. (See FIG. 1D). Distances tested included 33 bp, 117 bp, and 174 bp upstream of the TATA box. Expression was highest when the array of binding sites were present 33 bp from the TATA box, and expression decreased as the array of binding sites were further removed upstream of the TATA box. The distance between binding sites also was evaluated in an expression assay. (See FIG. 1E). Binding sites for ZF1 were placed either 6 bp apart (compact) or 16 bp apart (spaced). Higher expression was observed when the binding sites were placed greater than 6 bp apart up to 16 bp apart.

Figure 2:
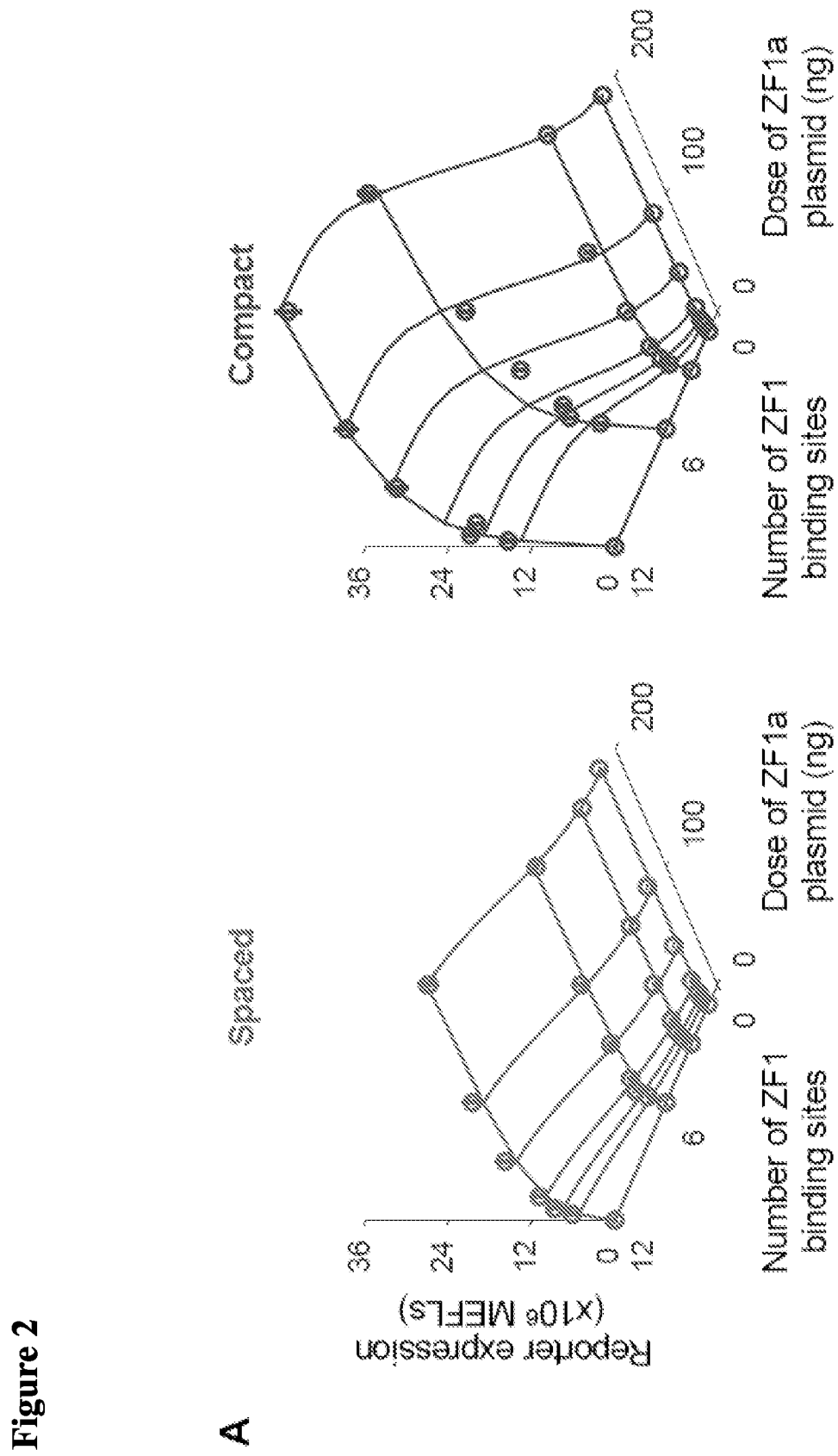
FIG. 2. Computational model for COMET. (A) A model that explains COMET-inducible gene expression using parameters for (1) a ZFa's regulation of the promoter, encompassing spacing and number of binding sites, and (2) a ZFa's pair of ZF and AD. The promoter affects m, and the ZFa affects both m and w. Lines show simulated end-point population mean reporter expression. Experimental data (circles) were collected in biologic triplicate, and processed as in FIG. 1. Error bars represent the S.E.M. Panels are representative of the same experiment. (B) Comparison of the COMET model with standard models for transcriptional regulation. Landscapes show normalized homogeneous reporter expression with different ZFa doses and numbers of binding sites. Standard models are grouped into four archetypal landscapes based on whether the cross-sectional response with respect to each axis is concave or sigmoidal. Parametric determinants of each archetype are: the Hill coefficient for non-cooperative (n=1) or cooperative (n>1) TF-DNA binding; a synergy term for non-cooperative (p=0) or cooperative (p>0) recruitment of RNAP by TFs; and equivalent (all α=1) or non-equivalent (not all α=1) maximal activation across different numbers of binding sites. Additional conditions for simulations are described in Methods.
Figure 2:
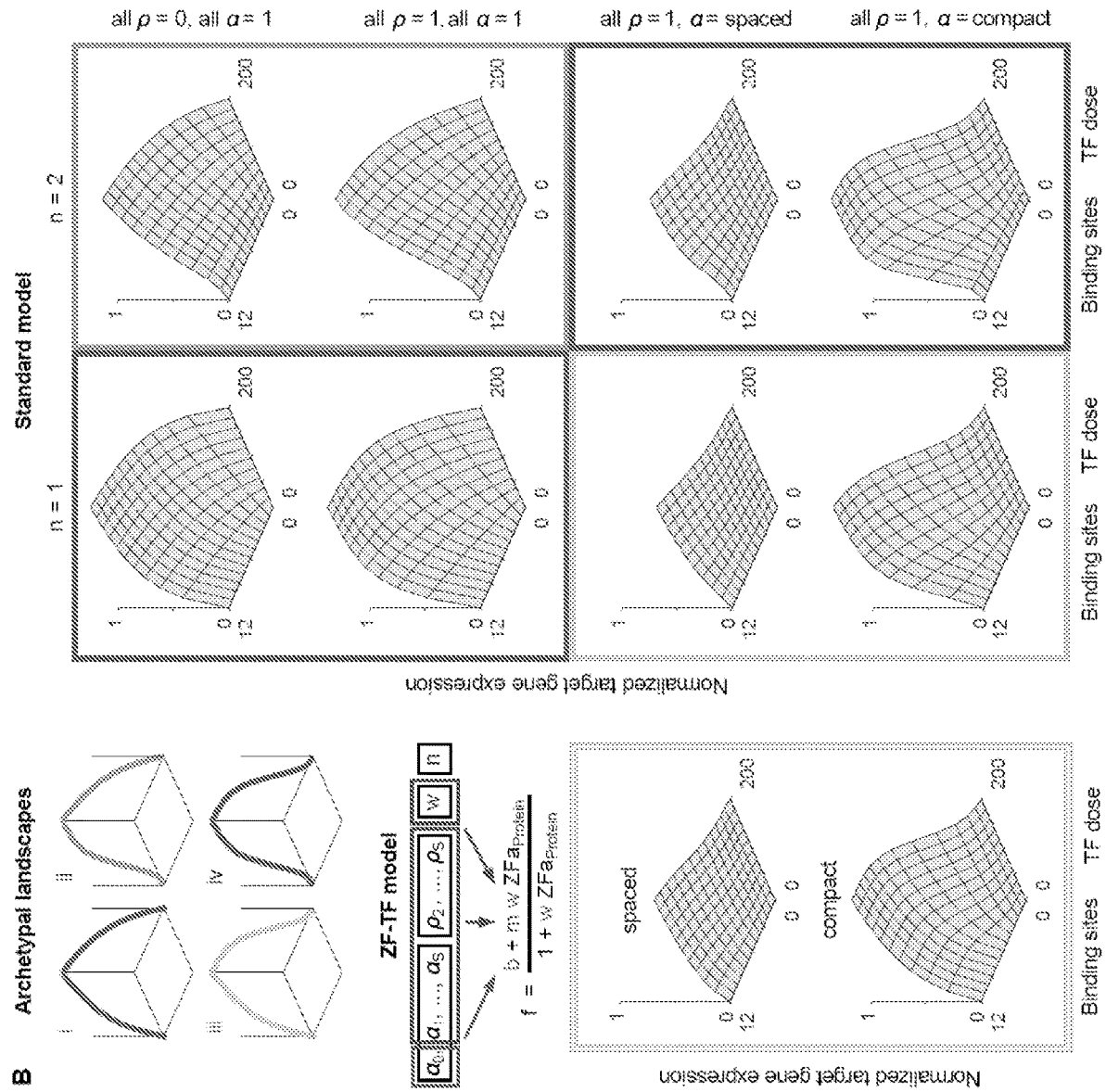

Computational model for COMET. Based on the results observed in FIG. 1, we created a computation model for COMET. (See FIG. 2A). The model in FIG. 2 explains COMET-inducible gene expression using parameters for (1) a ZFa's regulation of the promoter, encompassing spacing and number of binding sites, and (2) a ZFa's pair of ZF and AD. The computation model for COMET model was compared with standard models for transcriptional regulation. (See FIG. 2B). The computational model for COMET most closely resembled a standard model in which the TF dose response is concave and the binding site response is sigmoidal. This outcome arises from non-cooperativity in TF-DNA binding, cooperativity in RNAP recruitment, and maximum transcription that increases with number of binding sites. The COMET model explains the experimental outcomes using fewer parameters than the standard model.

Figure 3:
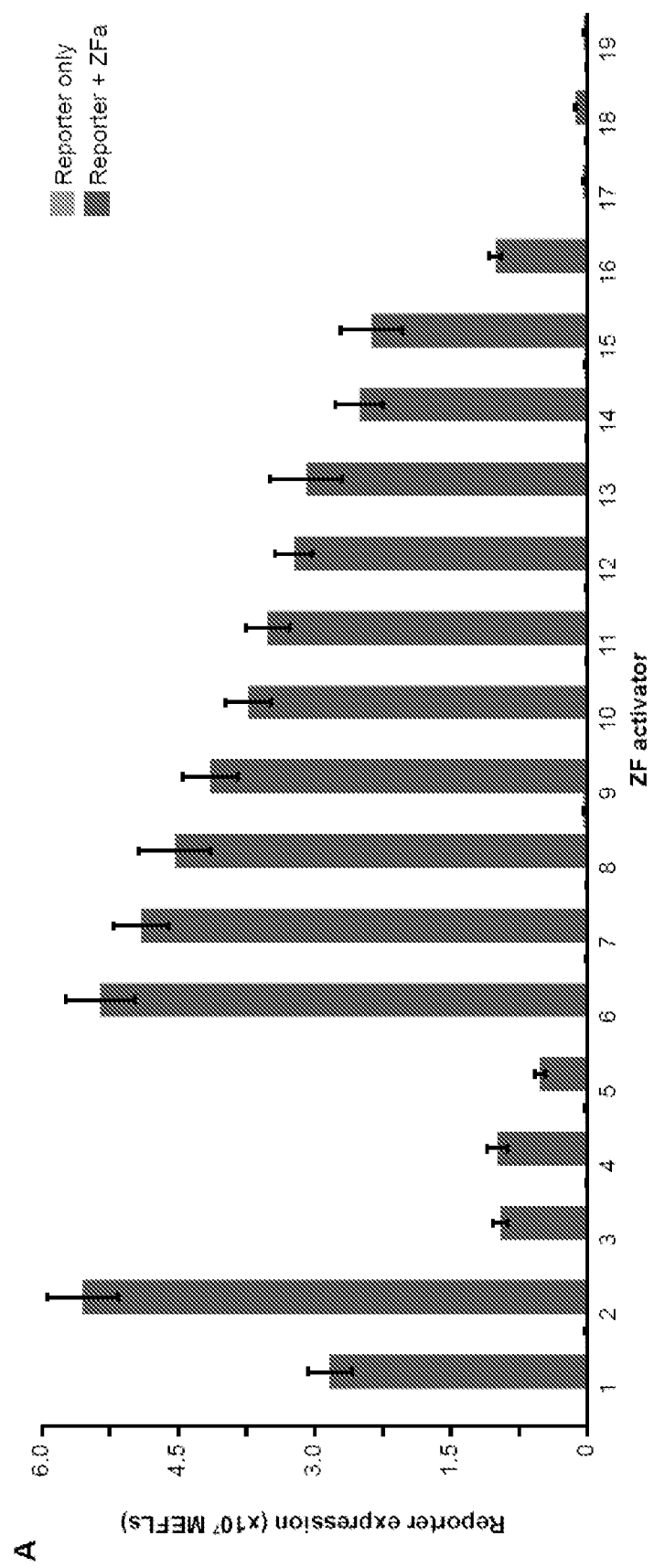
FIG. 3. Expanding the library of ZFa. (A) Activation conferred by 19 ZFa with different cognate binding sequences when paired with 6 binding site compact promoters. Evaluation of gene expression from compact promoters with varying numbers of binding sites for ZF2a (B) and ZF3a (C). (D) Investigating the orthogonality between the 12 strongest ZF, using 6 binding site compact promoters. Experiments were conducted in biologic triplicate, and data processed as in FIG. 1. Error bars represent the S.E.M. Each panel is representative of one experiment.
Figure 3:
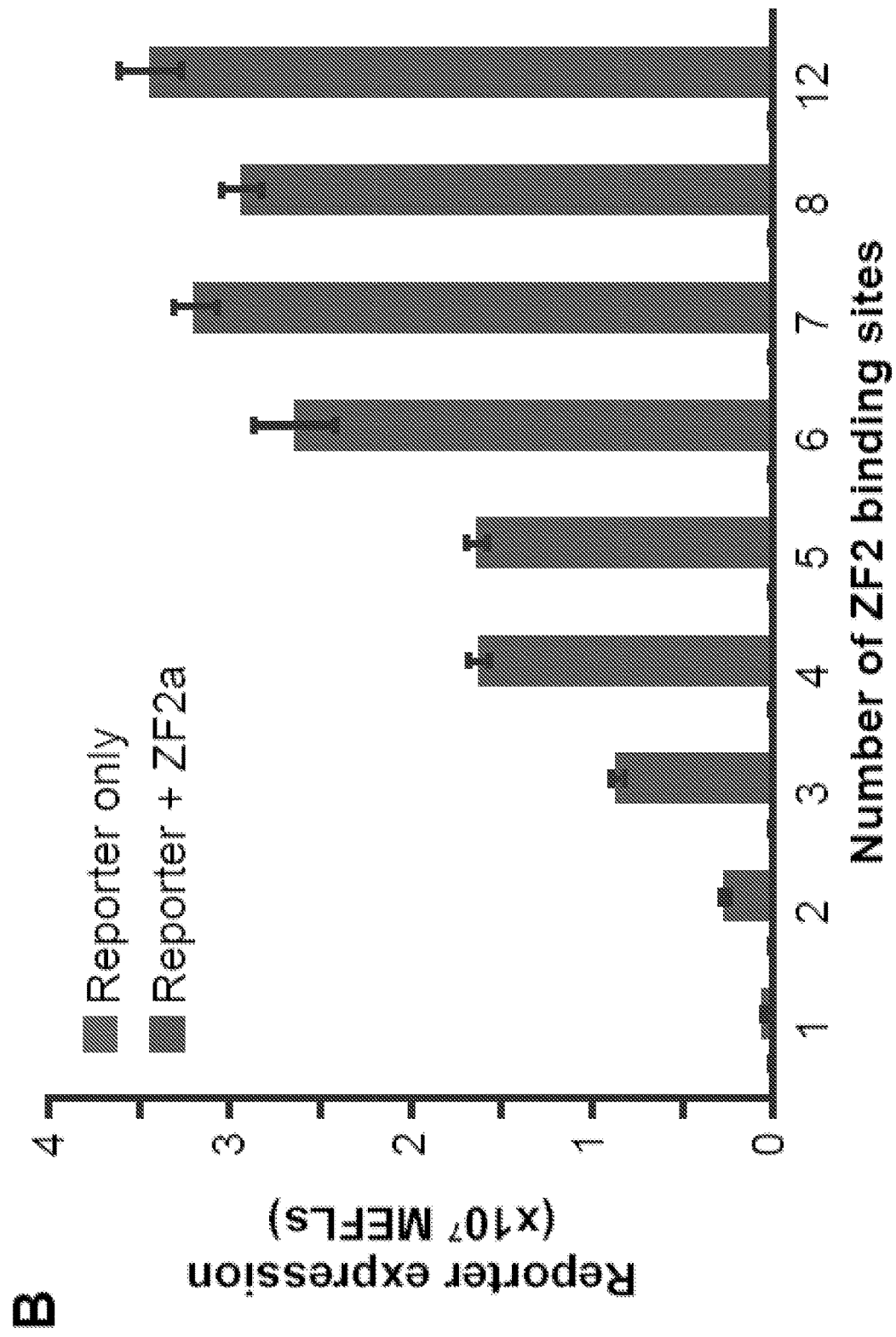
Figure 3:
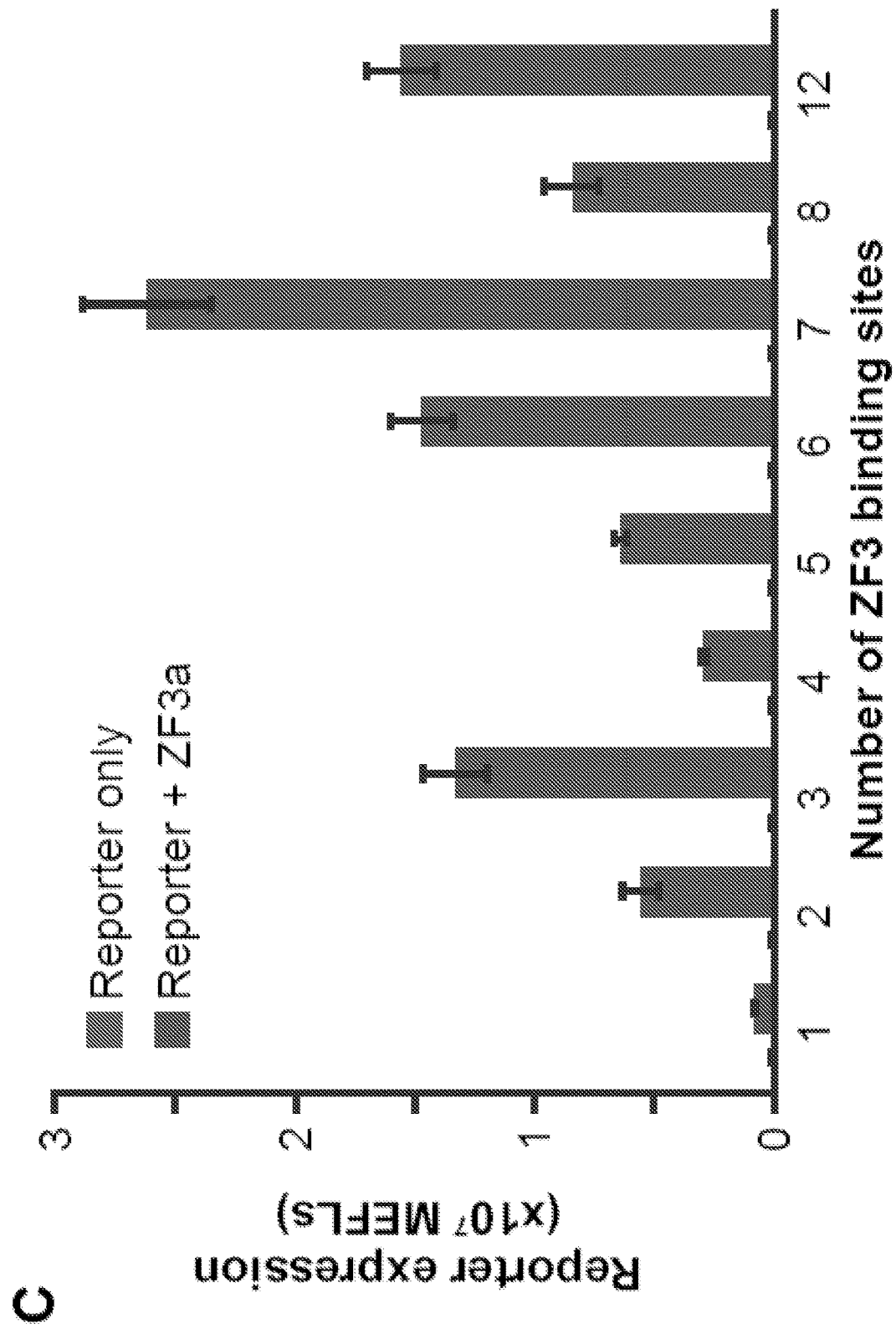
Figure 3:
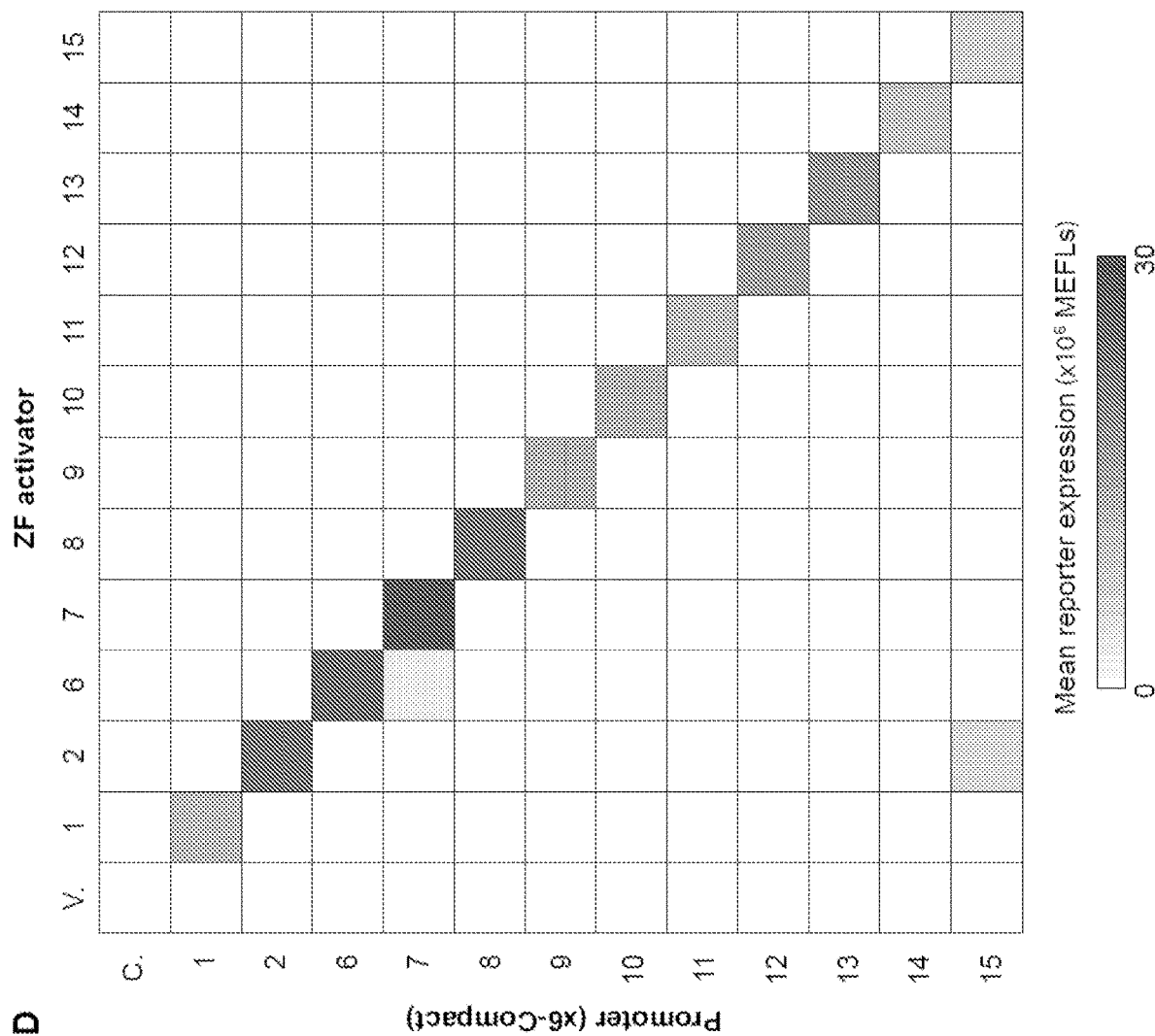

Expanded Library of ZFa. We next created an expanded number of ZFa's as per Table 1 (ZF1-19a). We tested nineteen different ZFa's in an expression assay by pairing each ZFa with 6 copies of its binding site spaced compactly in a synthetic promoter. (See FIG. 3A). ZF2a was most effective at increasing expression from the synthetic promoter. We selected ZF2a for further study and assessed the number of binding sites for ZF2a in the synthetic promoter in an expression assay. (See FIG. 3B). Expression increased proportionally with an increase in the number of binding sites from 1 to 12. However, expression appeared to partially level-off at 7-12 binding sites. We also selected ZF3a for further study and assessed the number of binding sites for ZF3a in the synthetic promoter in an expression assay. (See FIG. 3C). Expression increased proportionally with an increase in the number of binding sites from 1 to 7. However, expression appeared to partially level-off at 7 binding sites. We also investigated the orthogonality (i.e., match between ZF and cognate sequence) between the 12 strongest ZF of FIG. 3A using 6 binding site compact promoters similarly as in FIG. 3A. (See FIG. 3D). Significant promoter activation was observed only when a ZF was matched with its cognate binding sequence with the exception of ZF2 and binding sequence for ZF15.

Figure 4:
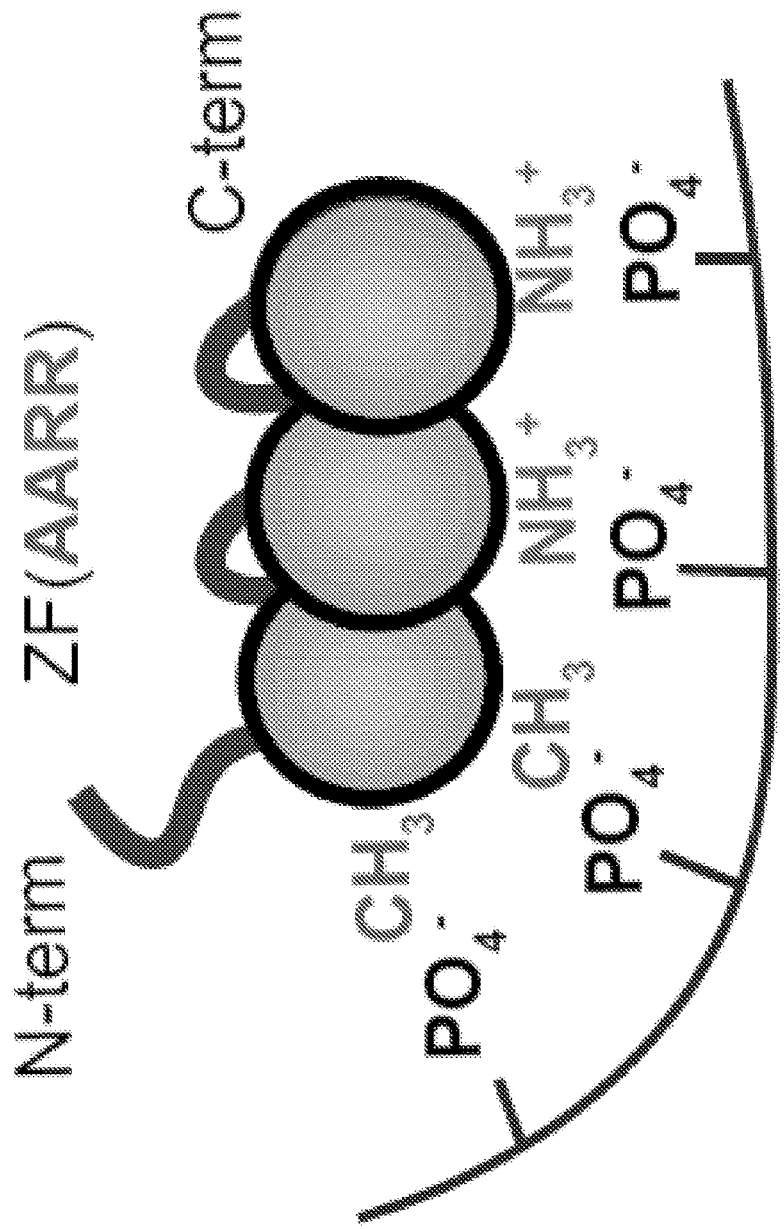
FIG. 4. Tuning transcription through ZFa engineering. (A) Schematic depicting the arginine to alanine DNA affinity mutations of ZF-based TFs. (B) Effects of DNA affinity mutations on TF strength. (C) Schematic depicting the activation domains of the ZFa. (D) Effects of activation domain on inducible gene expression, across several promoters. (E) Effects of activation domain on TF strength when paired with a weak ZF binding domain. (F) Summary of the tunable parameters of COMET promoters and ZFa.
Figure 4:
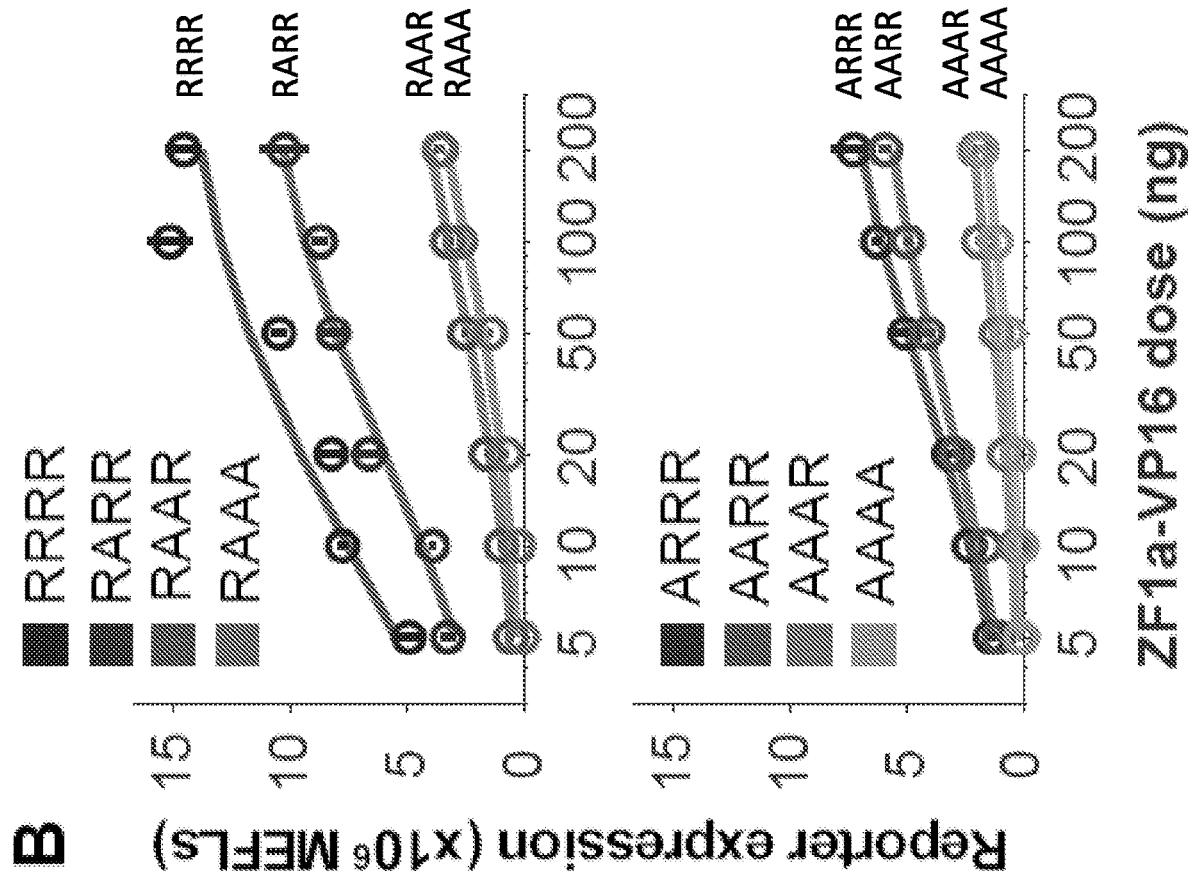
Figure 4:
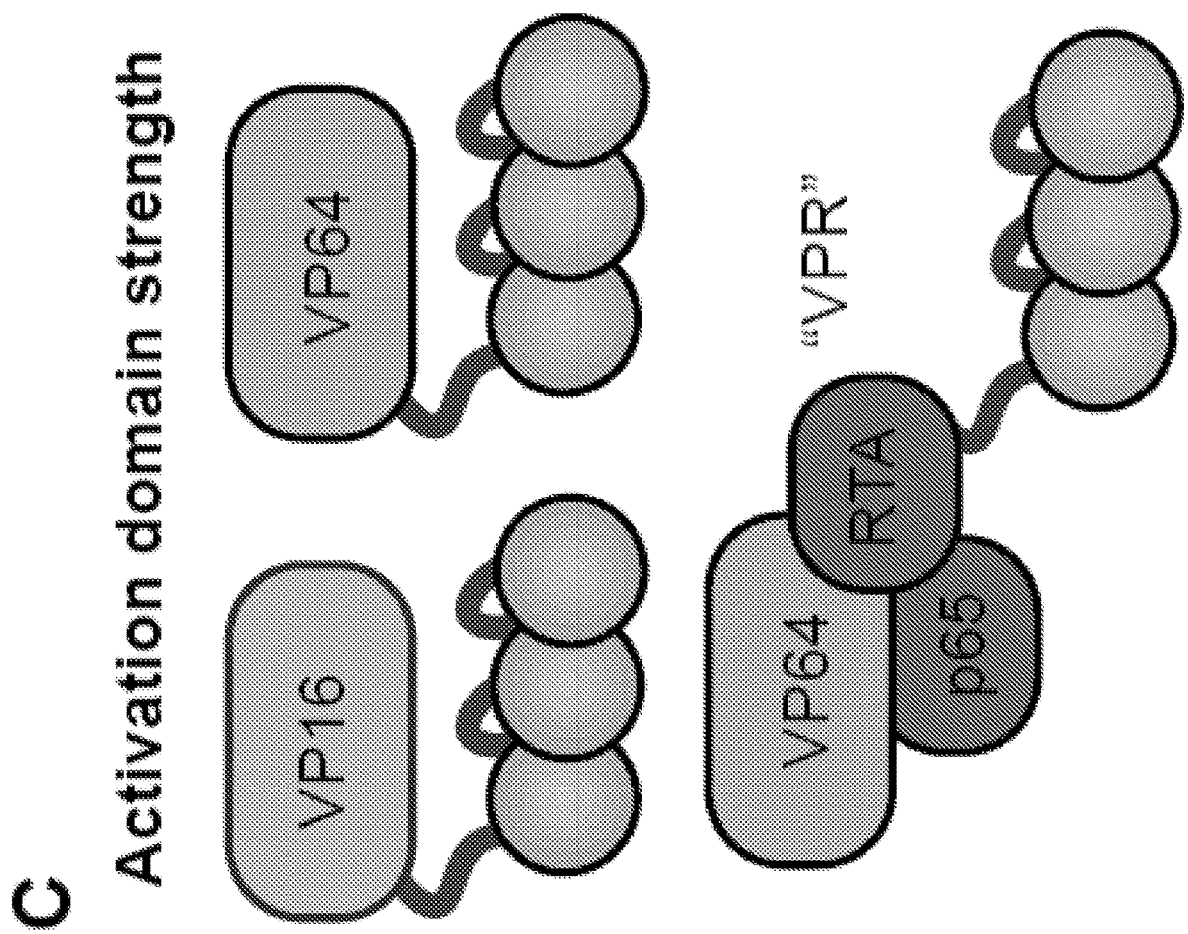
Figure 4:
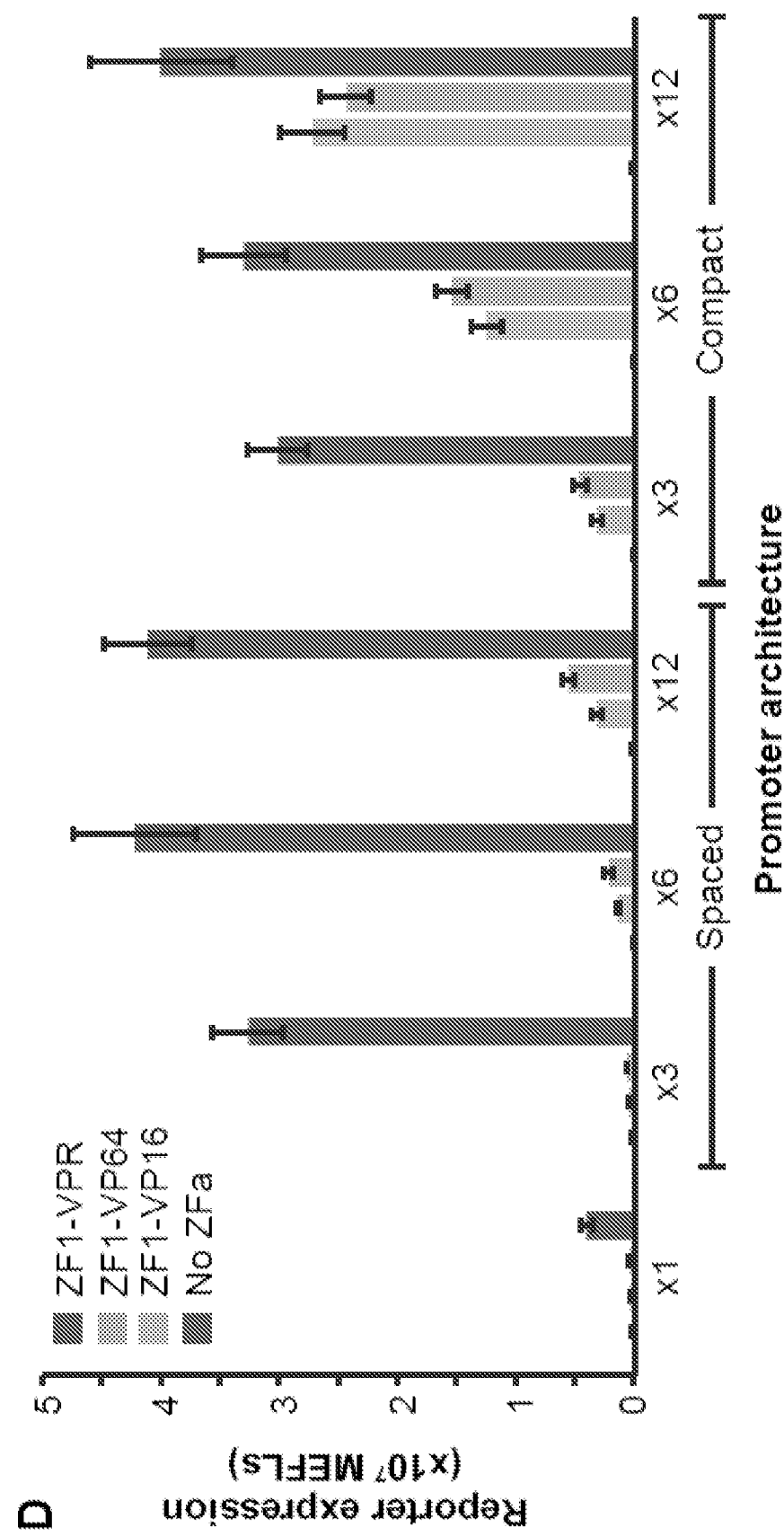
Figure 4:
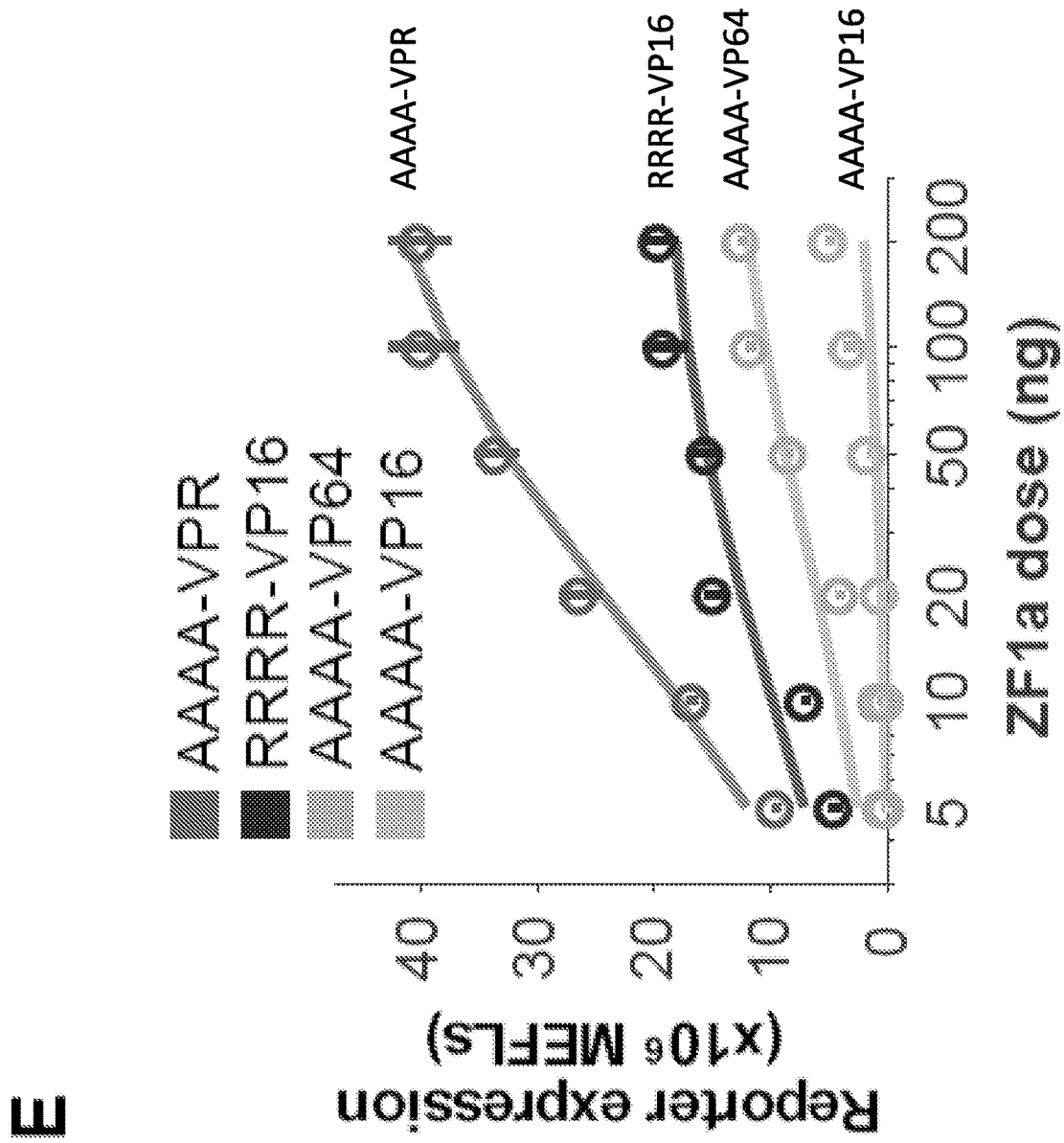
Figure 4:
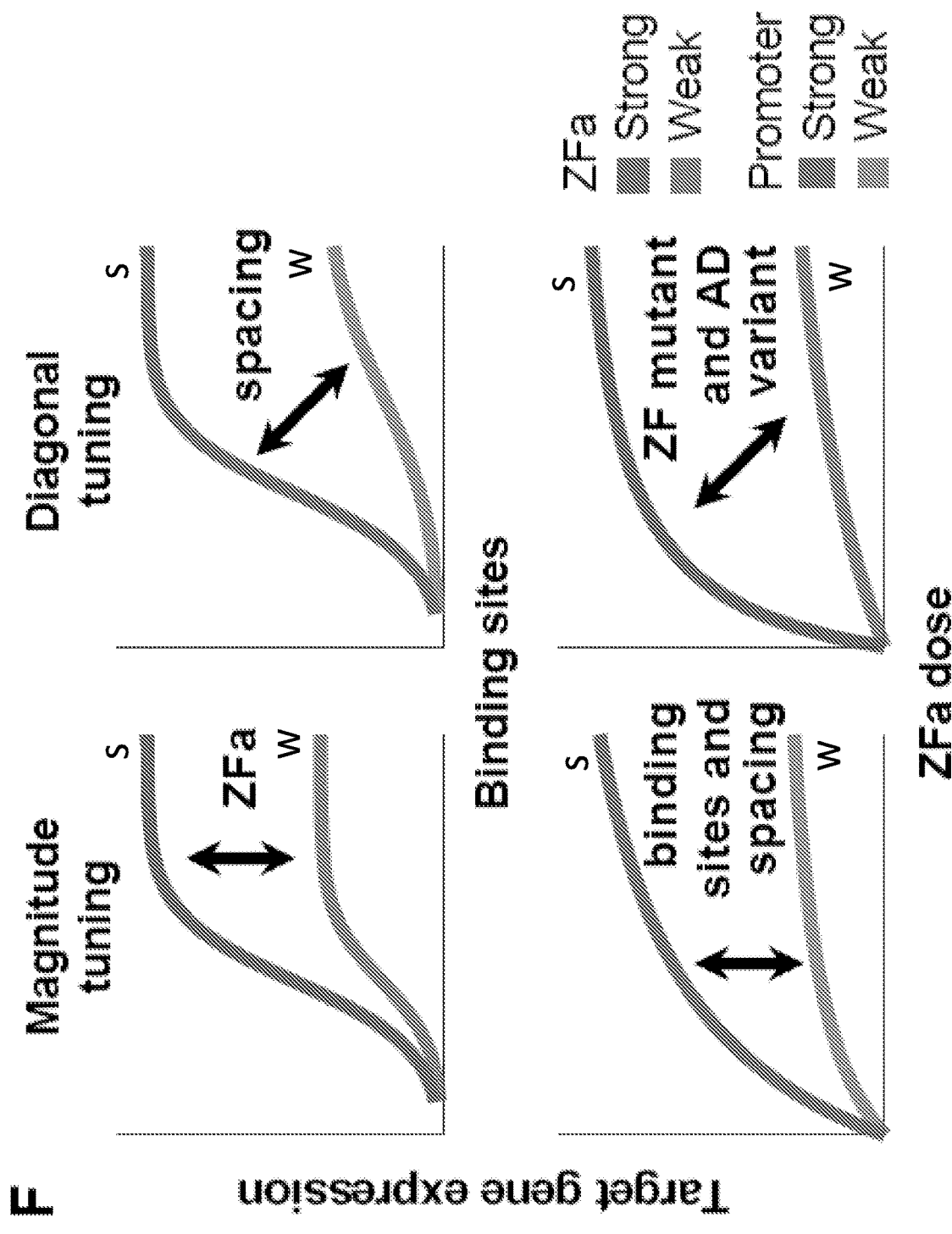

Tuning Transcription Through ZFa Engineering. Arginine residues in zinc fingers are thought to interact with DNA via an ionic interaction between positively charged amino groups in the arginine residues and negatively charged phosphate groups in the DNA. (See FIG. 4A). When arginine residues are replaced with alanine residues having methyl side chains, this ionic interaction no longer occurs. We explored whether we could tune binding of ZF1a to DNA by replacing arginine residues with alanine residues, or conversely, by replacing alanine residues with arginine residues. By replacing arginine residues with alanine residues we expected to reduce affinity of ZF1a for its cognate DNA sequence, and conversely, by replacing alanine residues with arginine residues with arginine residues we expected to increase affinity of ZF1a for its cognate DNA sequence. We expected that ZF1a variants having higher affinity would increase transcription from a synthetic promoter comprising cognate binding sites for ZF1a. We created eight ZF1a having arginine residues or alanine residues within a four amino sequence of ZF1a (i.e., RRRR, RARR, RAAR, RAAA, ATTT, AATT, AAAR, and AAAA). We observed higher expression from reporters when the ZF1a variant had a higher number of arginine residues within the four amino acid sequence (i.e., RRRR>RARR>RAAR>RAAA and ARRR>AARR>AAAR>AAAA). (See FIG. 4B). We also created additional ZF1a variants having different activation domains than VP16 (ZF1-VP16), including VP64 (ZF1-VP64) or a combination of VP64, RTA, and p65 referred to as "VPR" (ZF1-VPR). (See FIG. 4C). We then tested these additional variants having these different activation domains in an expression assay varying the number of binding sites for the zinc finger (×1, ×3, or ×6) and spacing of the binding sites (spaced 16 bp or compact 6 bp). (See FIG. 4D). ZF1-VPR exhibiting the highest activity in the expression assay and under configurations where ZF1-VP16 and ZF1-VP64 exhibiting little or no activity. (See FIG. 4D, ZF1-VPR at ×6, spaced). We also tested the effects of the activation domain (VP16, VP64, or VPR) when paired with a weak ZF binding domain (AAAA) versus a strong binding domain (RRRR). (See FIG. 4E). A summary of the tunable parameters of COMET promoters and ZFa is provided in FIG. 4F including a summary of the magnitude tuning (e.g., selection of ZF, cognate binding site, and spacing), and diagonal tuning (e.g., spacing of binding sites and mutation of ZF to modulate affinity for its binding site).

Zinc Finger Inhibitors. Each zinc finger inhibitor (ZFi) is also based on a ZF protein that can bind DNA. This ZF by itself can bind to the same sequence as a ZFa or a sequence that overlaps with the sequence of the ZFa. (See FIG. 5A). We created two COMET inhibitors. ZF1i and ZF1i-dsRed-Express2, each of which includes the zinc finger of ZF1a and can competitively bind to the cognate sequence of ZF1a. ZF1i lacks a transcription activator domain and ZF1i-dsRedExpress2 includes the dsRedExpress2 domain instead of a transcription activator domain. The ability of ZF1i and ZFi-dsRedExpress2 to inhibit transcription activation by ZF1a was tested in an expression assay. Both of ZF1i and ZF1i-dsRedExpress2 reduced transcriptional activation by ZF1a with ZF1i-dsRedExpress2 reducing transcriptional activation by ZF1a more severely. (See FIG. 1A)

Figure 5:
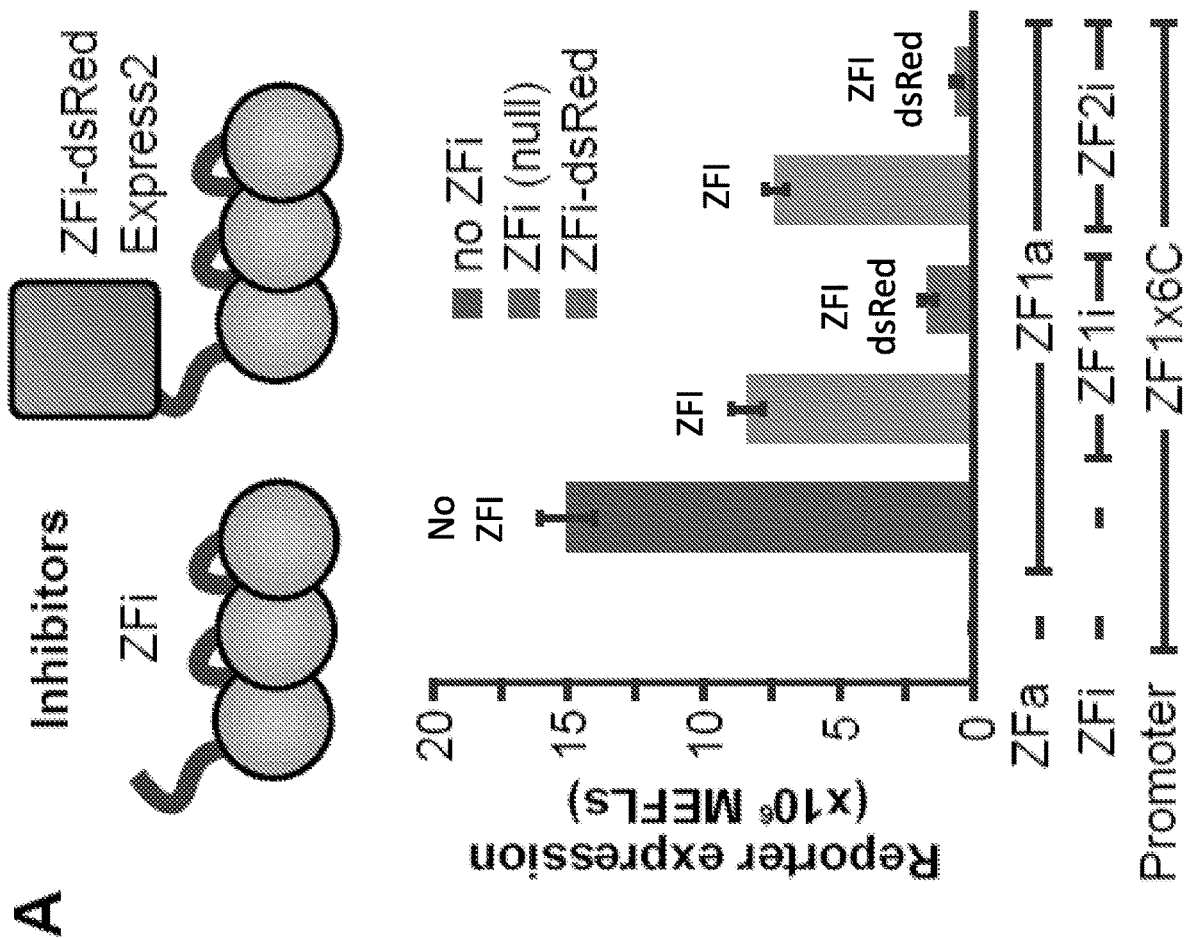
FIG. 5. Gene expression inhibition with ZFi. (A) Evaluating strategies for inhibition with ZFi. (B) COMET inhibitors use two mechanisms: (1) competitive inhibition of ZFa from binding the promoter, and (2) reduction in cooperativity by decreasing the effective compactness of ZFa. (C) ZFi and ZFi-dsRed differ from standard competitive inhibitors. Predictions for competitive inhibition alone track the solid lines, whereas COMET inhibitors track the dotted lines toward single-site promoter behavior. X-axes are scaled linearly from 0 to 10 ng and logarithmically above 10 ng. (D) Experimental measurements and model predictions for reporter expression regulated by a ZFa and a panel of ZF1i mutants with x6-Compact promoter. Experiments were conducted in biologic triplicate, and data processed as in FIG. 1. Error bars represent the S.E.M. Each panel is representative of one experiment.
Figure 5:
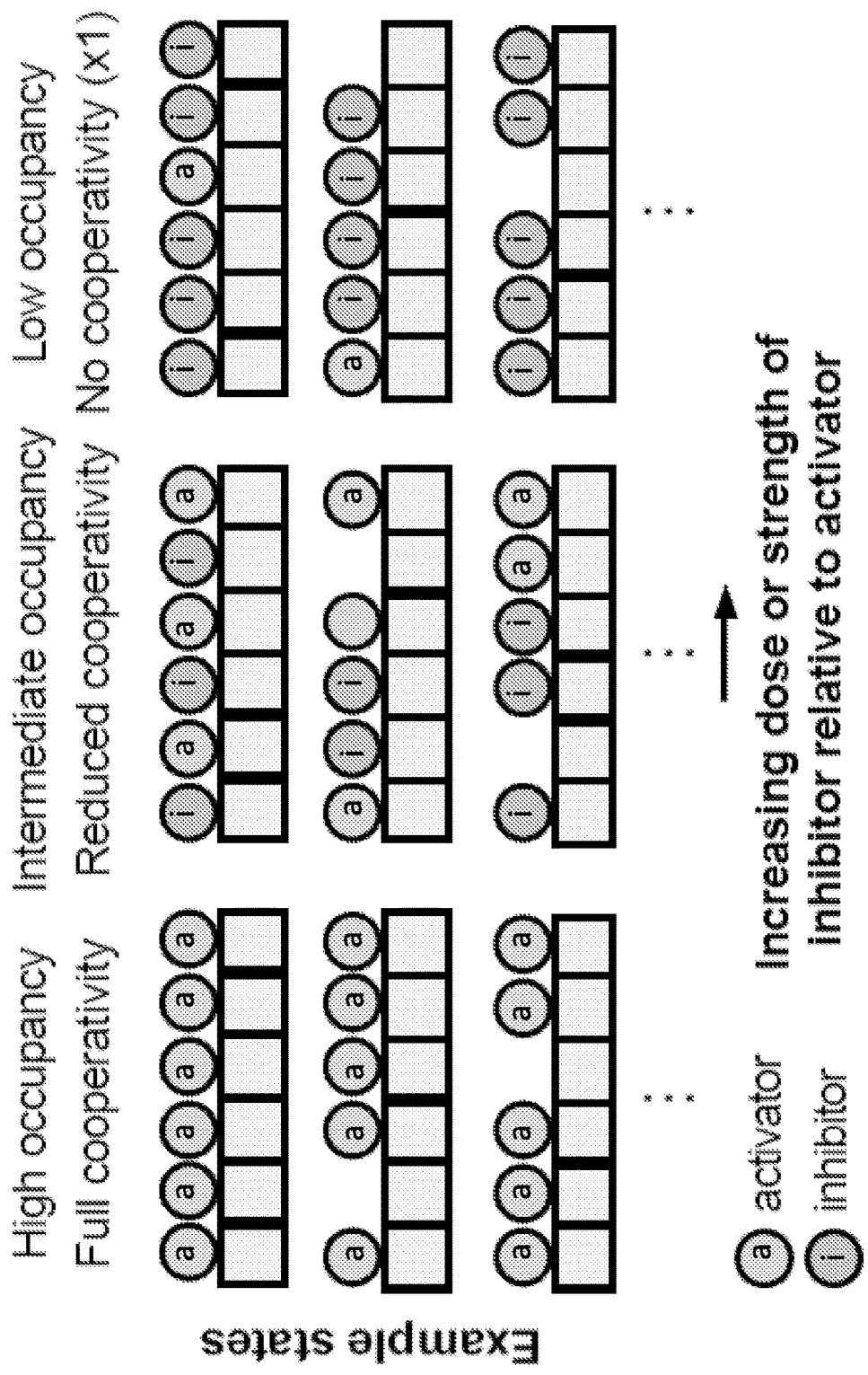
Figure 5:
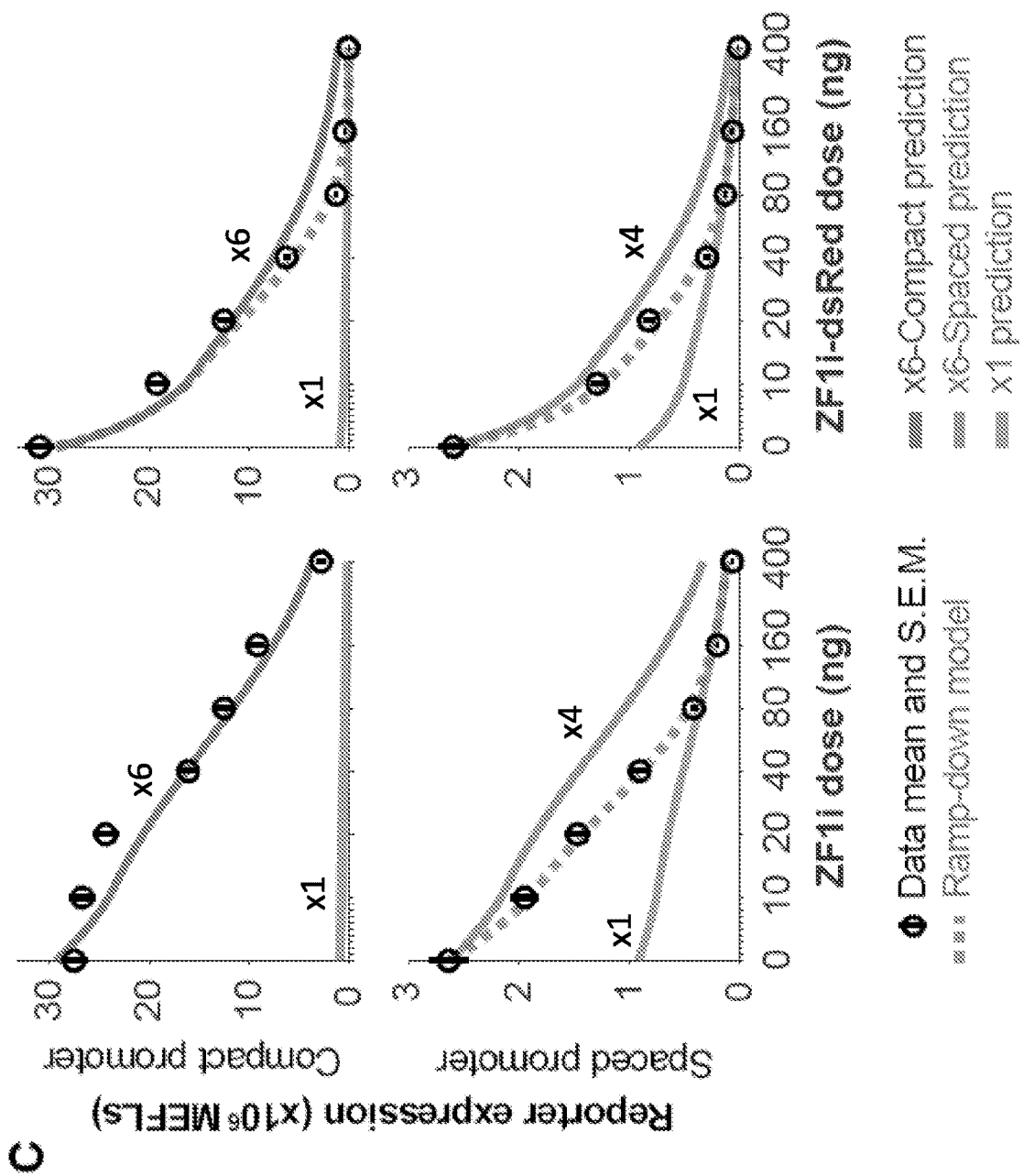
Figure 5:
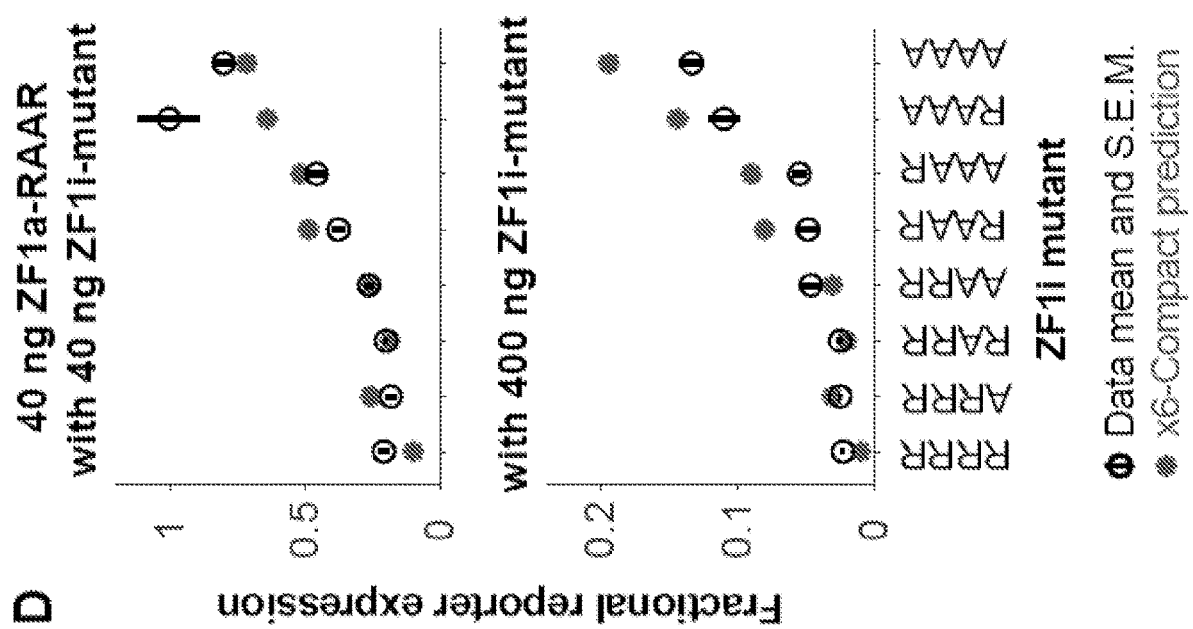

COMET inhibitors use two mechanisms: (1) competitive inhibition of ZFa from binding the promoter, and (2) reduction in cooperativity by decreasing the effective compactness of ZFa. These mechanisms are illustrated in FIG. 5B. A model based on these mechanisms might predict that the dose of an inhibitor ZFi versus a corresponding reduction in transcription activation by ZFa might not be linear and may exhibit a "ramp-down" curve. We tested the reduction in transcription activation by ZF1a versus dose of ZF1i or ZF1i-dsRedExpress2. We observed a "ramp-down" curve for ZF1i-dsRedExpress2 but not for ZF1i. (See FIG. 5C). ZF1i-dsRedExpress2 is larger in size than ZF1i and therefore may exhibit a larger effect in decreasing the effective compactness of ZF1a than does ZF1i. We also created and tested various ZF1i mutants having amino acid replacements in four amino acids arginine/alanine sequence. (See FIG. 5D). ZF1a-RAAR versus various ZF1i mutants were tested in an expression assay. ZF1i-RRRR exhibited the larger inhibition of transcriptional activation by ZF1a-RAAR, suggesting that ZF1i's binding affinity correlates with its ability to inhibit transcriptional activation by ZF1a-RAAR.

Figure 6:
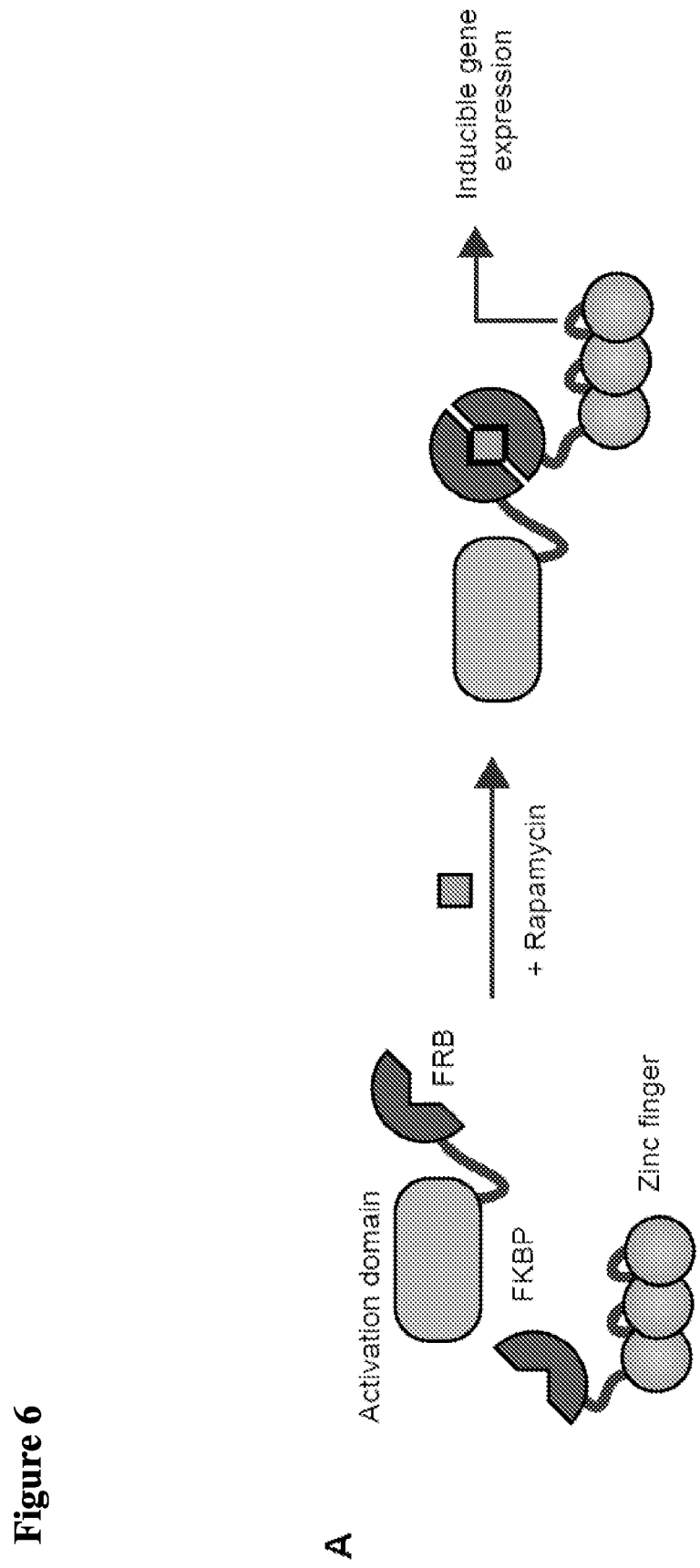
FIG. 6. Engineering small molecule-inducible TFs. (A) Schematic depicting chemically inducible control of gene expression with an RaZF. (B) Investigating the effects of promoter architecture and activation domain on RaZF performance. (C) Effects of component expression levels on RaZF performance. Experiments were conducted in biologic triplicate, and data processed as in FIG. 1. Error bars represent the S.E.M. Each panel is representative of one experiment.
Figure 6:
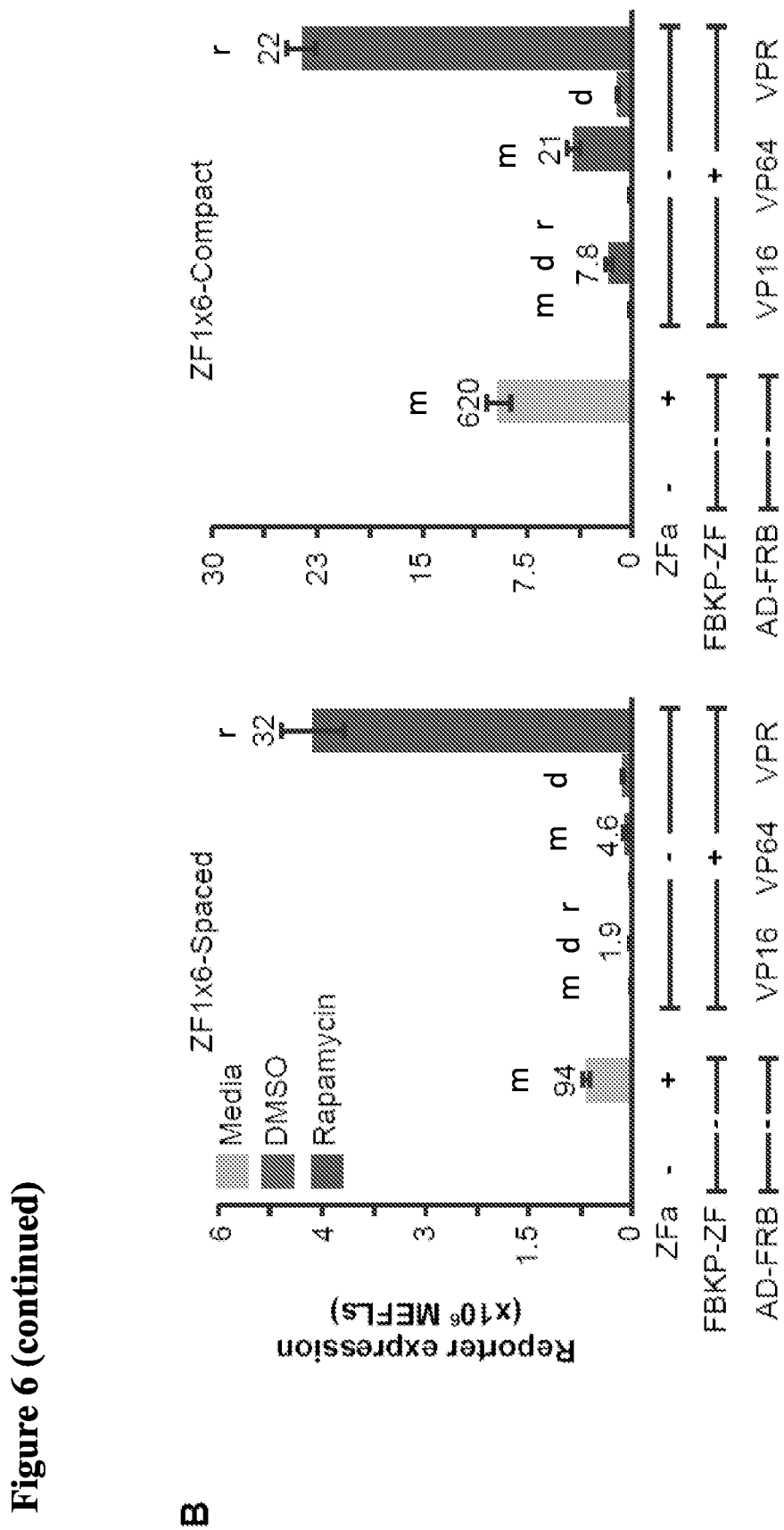
Figure 6:
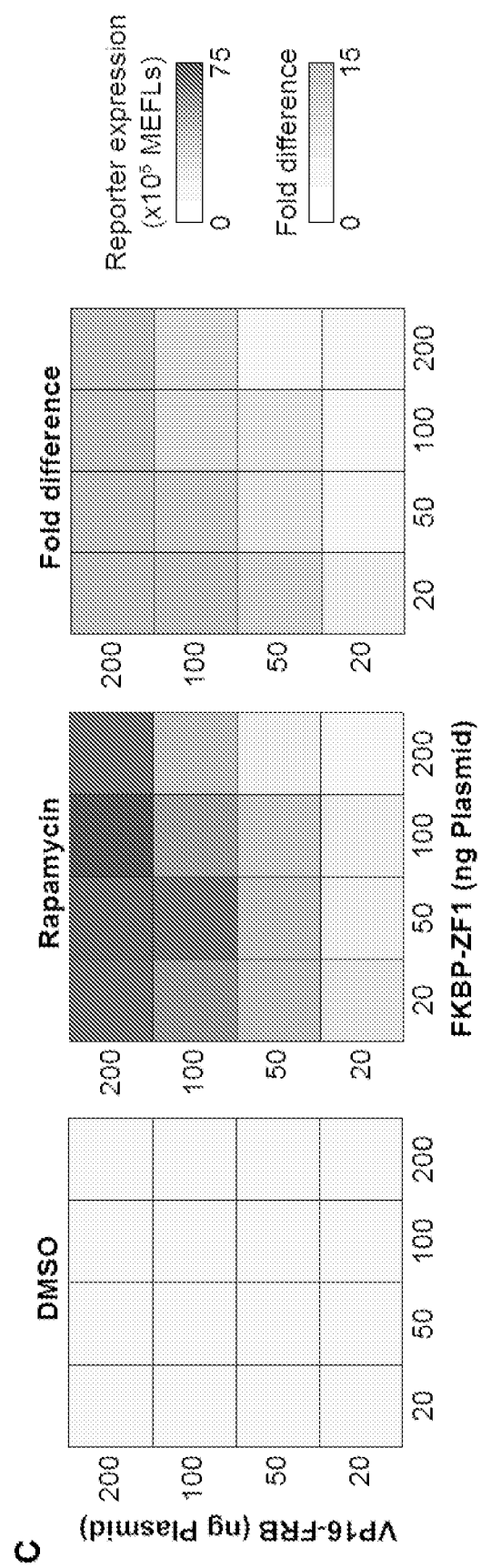

Engineering Small Molecule-Inducible TFs. We next tested whether we could engineer small molecule-inducible transcription factors. We selected rapamycin as a small molecule utilized the FRB and FKBP binding domains to create a bi-partite transcription factor. (See FIG. 6A). The bi-partite transcription factor includes a DNA-binding part that includes a zinc finger fused to FKBP and a transcriptional activation part that includes a transcriptional activation domain fused to FRB. In the presence of rapamycin, the DNA-binding part via its FKBP binding domain and the transcriptional activation part via its FRB binding domain can bind the rapamycin and constitute a transcriptional factor that can bind DNA via its zinc finger and activate transcription via its transcriptional activation domain. (See FIG. 6A). We created and tested three such bi-partite transcription factors having transcriptional activation domains from VP16, VP64, and VPR in an expression assay in the presence of rapamycin and compared their activity to the ZF1a. (See FIG. 6B). The bi-partite transcription factors were inducible in the presence of rapamycin with the transcription factor having a VPR activation domain exhibiting the highest transcription activation, even higher than ZF1a. (See FIG. 6B). The effects of component expression levels on the performance of these rapamycin-inducible transcription factors is shown in FIG. 6C.

Figure 7:
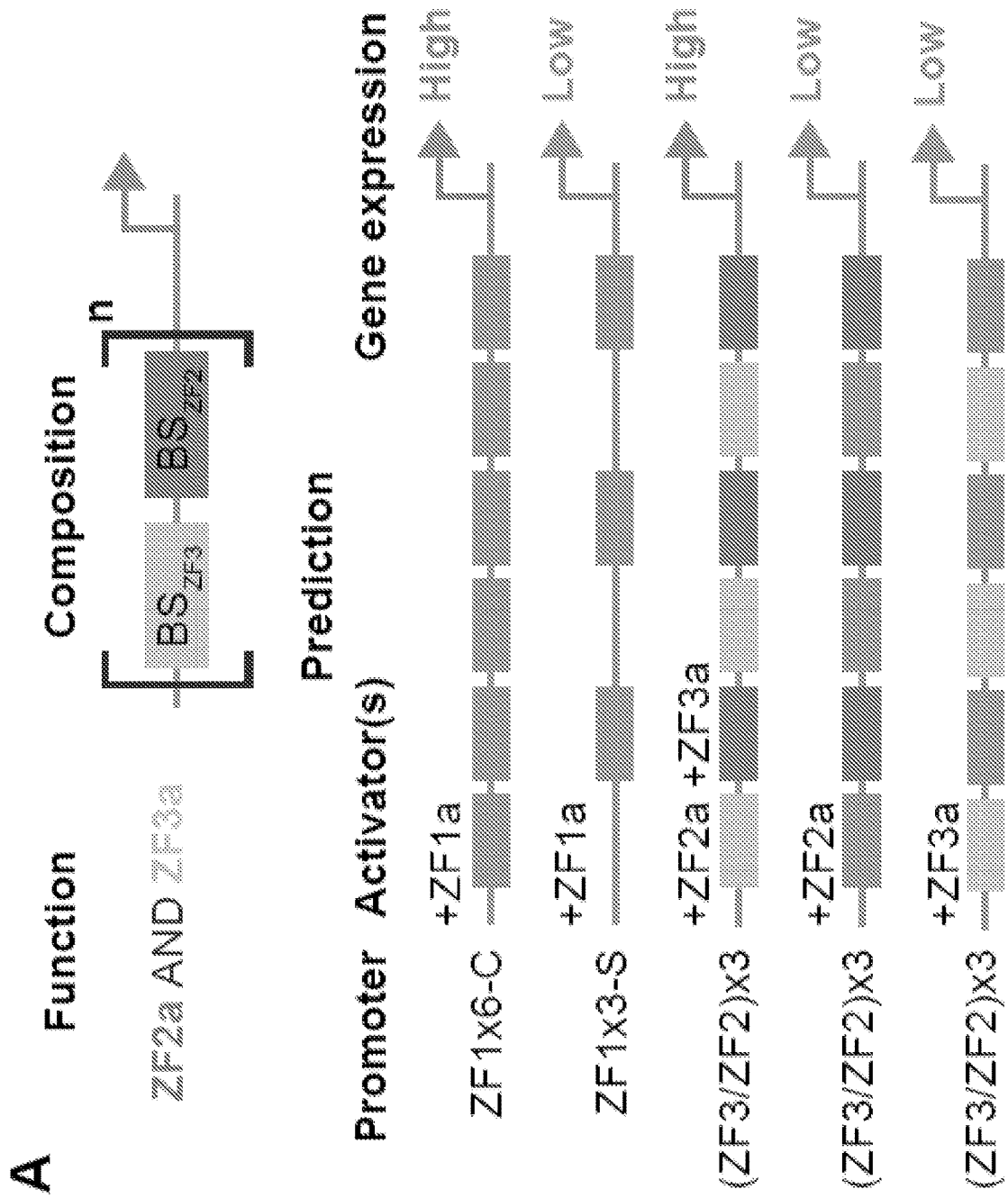
FIG. 7. Cellular logic gates with COMET. (A) Strategy for designing promoter-based logic gates with COMET. (B) Performance of two-input AND gates with one to four repeats of the paired binding site motif. (C) Dose response profile for the AND gate with three repeats of the paired binding site motif. (D) Comparison of standard models with ZF-TF AND gate behavior. (E) Performance of a three-input AND gate with two repeats of the triplet binding site motif. (F) Incorporation of repressors into cellular logic, demonstrated by a four-input gate. Experiments were conducted in biologic triplicate, and data processed as in FIG. 1. Error bars represent the S.E.M. Each panel is representative of one experiment.
Figure 7:
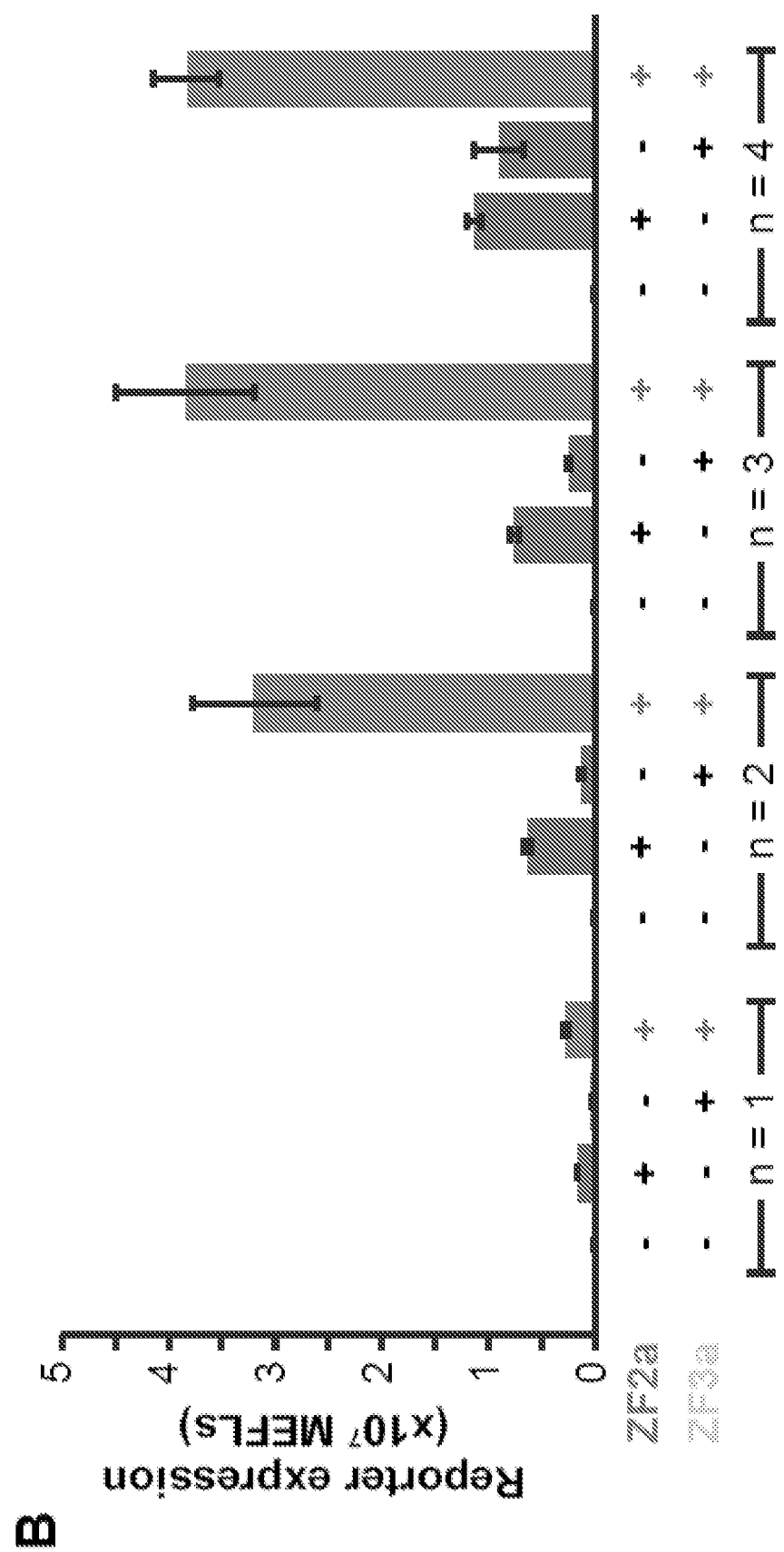
Figure 7:
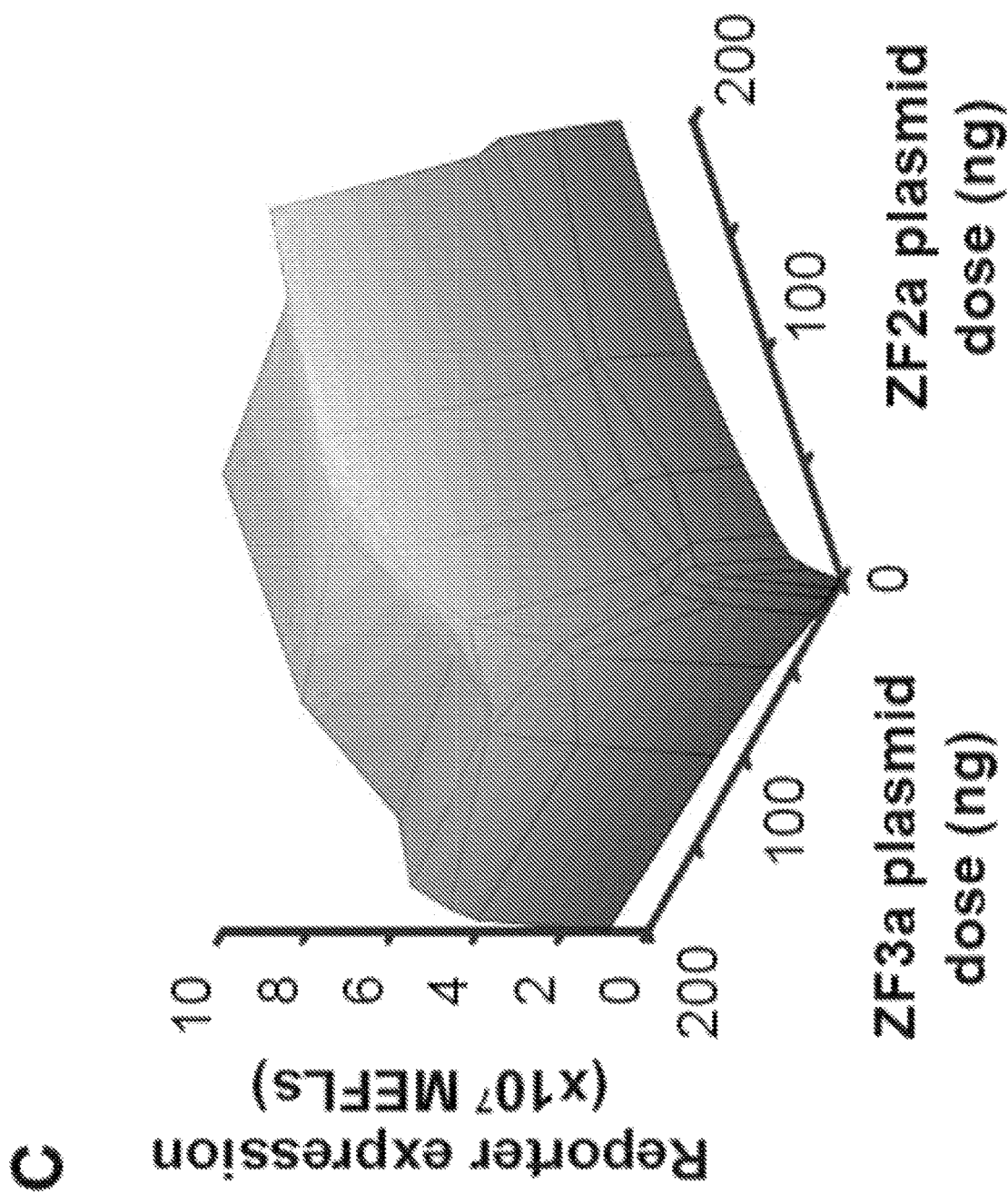
Figure 7:
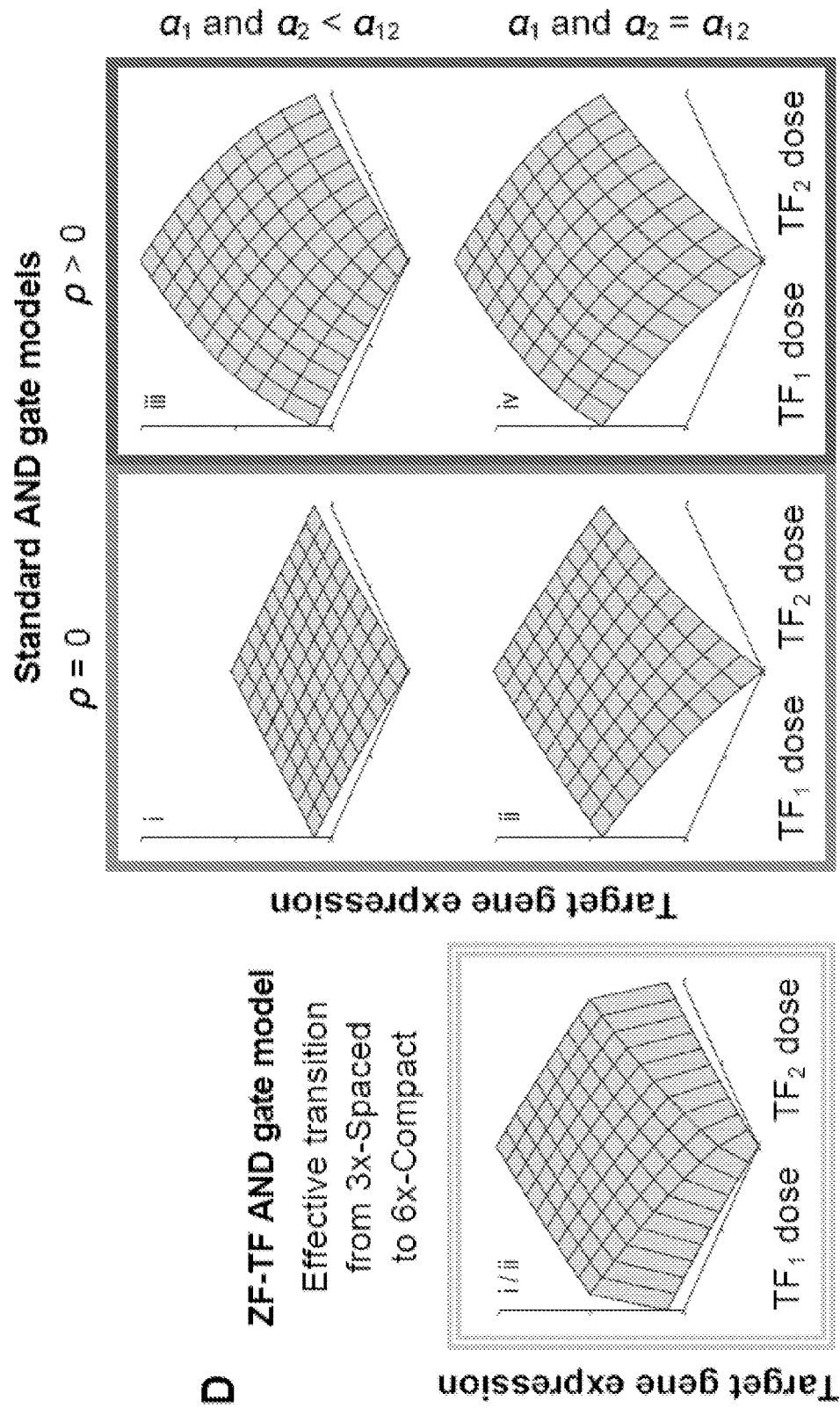
Figure 7:
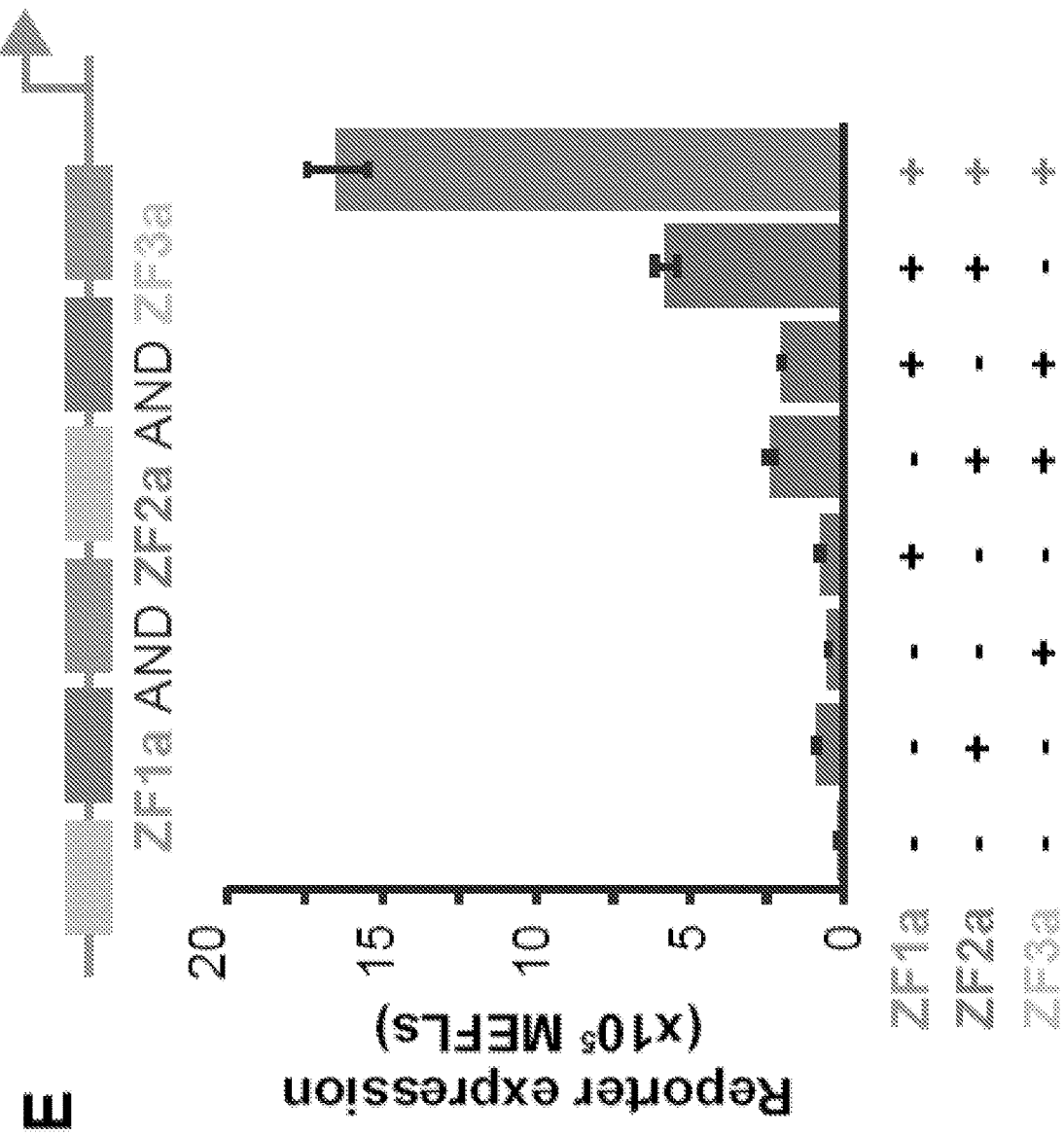
Figure 7:
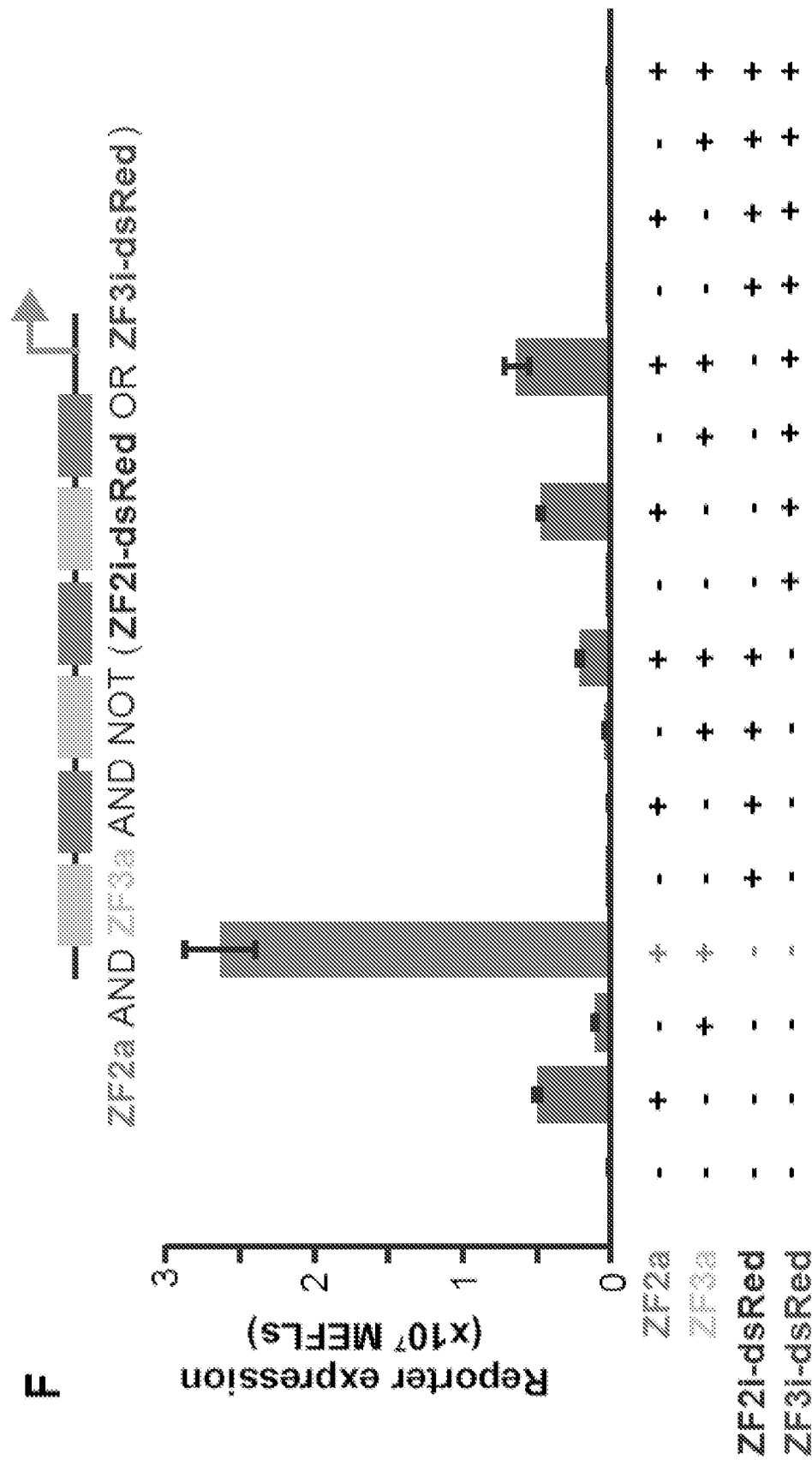

Engineered Promoters. Engineered promoters consist of two parts: a minimal promoter, which allows the recruitment of RNA polymerases and the initiation of transcription, and a ZF binding site array. This ZF binding site array consists of one or more ZF binding sites, which are 9 base pair sequences of DNA to which a ZF can bind, for one or more ZF. The promoters are then followed by a gene of interest, which in all constructs tested so far is a fluorescent protein that can be visualized by methods including microscopy or flow cytometry. Strategies for designing promoters are illustrated in FIG. 7A.

A promoter including 3 binding sites for a single ZFa exhibits low expression whereas a promoter including 6 binding sites for the single ZFa exhibits high expression. However, as indicated, promoters may be hybrid type promoters including binding sites for multiple zinc fingers. For example, hybrid promoter including three binding sites for each of ZF2a and ZF3a would be predicted to exhibit high expression only in the presence of both of ZF2a and ZF3a. Therefore, this hybrid promoter could be engineered to exhibit "AND" type logic in regard to expression. We tested hybrid promoters including 1, 2, 3, or 4 copies of the binding sites for ZF2a and/or ZF3a in an expression assay. (See FIG. 7B). We observed that expression was highest only when the promoter included multiple binding sites for both of ZF2a and ZF3a and when both of ZF2a and ZF3a were present, indicative of an "AND" logic gate. A dose response profile for the AND gate with three repeats of the paired binding site motif is provided in FIG. 7C, and a comparison of standard models with ZF-TF AND gate behavior is provided in FIG. 7D.

We tested a three-input gate as well utilizing a promoter having two binding sites for each of ZF1a, ZF2a, and ZF3a in the presence of ZF1a, ZF2a, and/or ZF3a in an expression assay. (See FIG. 7E). Again, we observed highest expression for the promoter having two binding sites for each of ZF1a, ZF2a, and ZF3a only when a combination of ZF1a, ZF2a, and ZF3a was present, indicative of three-input AND logic gate.

We similarly tested a four-input gate. We utilized a promoter including three binding sites for each of ZF2a and ZF3a and tested expression in the presence of ZF2a and/or ZF3a, as transcription activators, and ZF2i-dsRed and/or ZF3i-dsRed, as transcription inhibitors. (See FIG. 7F). Transcription was highest only in the presence of both of ZF2a and ZF3a and in the absence of ZF2i-dsRed and/or ZF3i-dsRed, indicative of four-input AND logic gate.

Supplemental Studies

Figure 8:
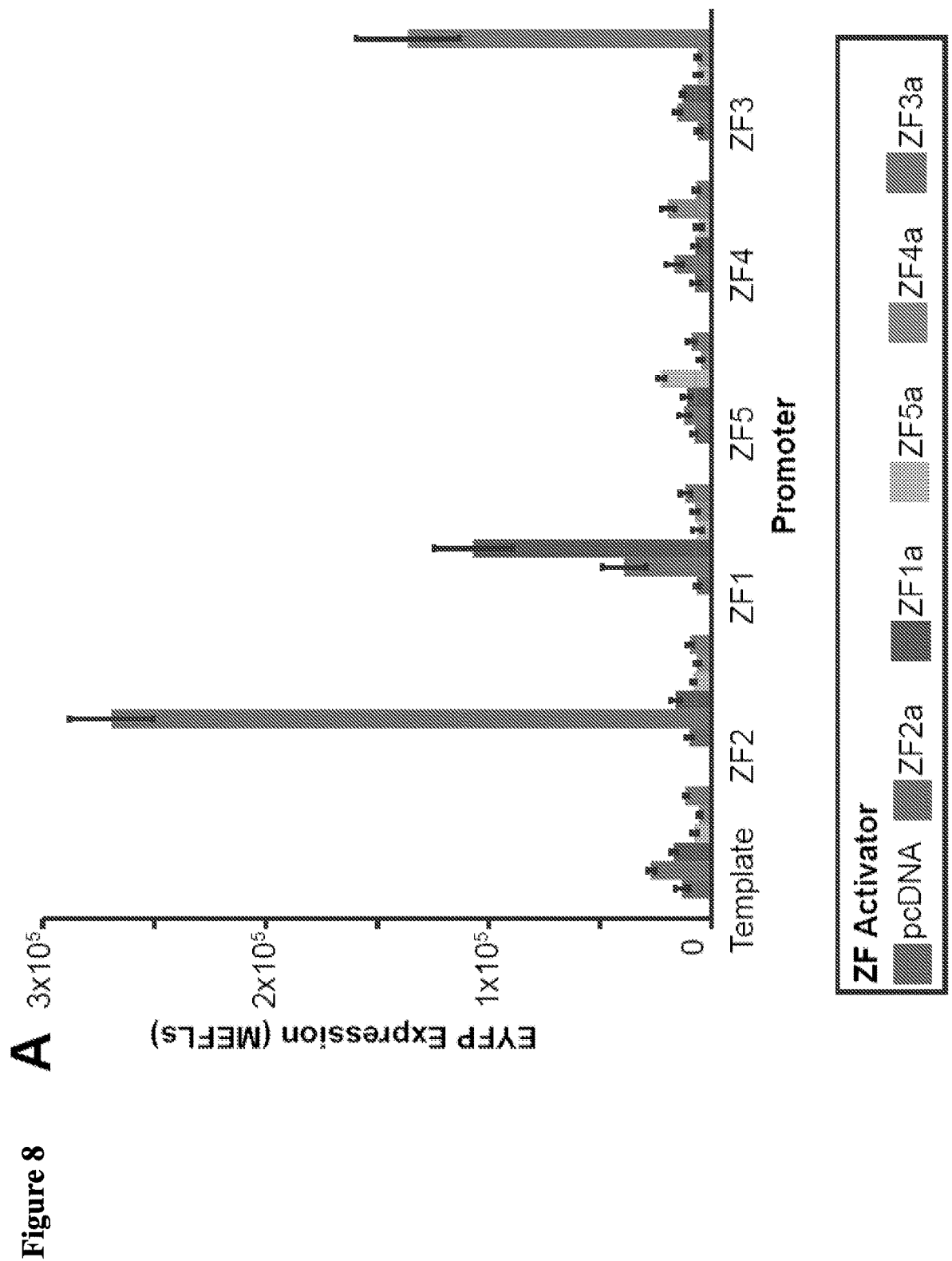
FIG. 8. ZFa induce transcription orthogonally.

ZFa induce transcription orthogonally. Plasmids encoding a ZFa or an empty vector (pcDNA) were transfected with the reporter constructs with either (i) one ZF binding site or (ii) a "Template" construct containing a minimal promoter and EYFP gene but no added ZF binding sites. (See FIG. 8). Each promoter was maximally responsive to its own ZFa (with the exception of ZF4 which responded equally to both ZF2a and ZF4a). Likewise, each ZFa induced the maximal reporter expression only when paired with its cognate promoter. ZF2a was able to activate transcription from several reporters, however this may be due to a cryptic binding site rather than affinity for another ZF binding site, as evidenced by its activation of gene expression from the "Template" construct.

Figure 9:
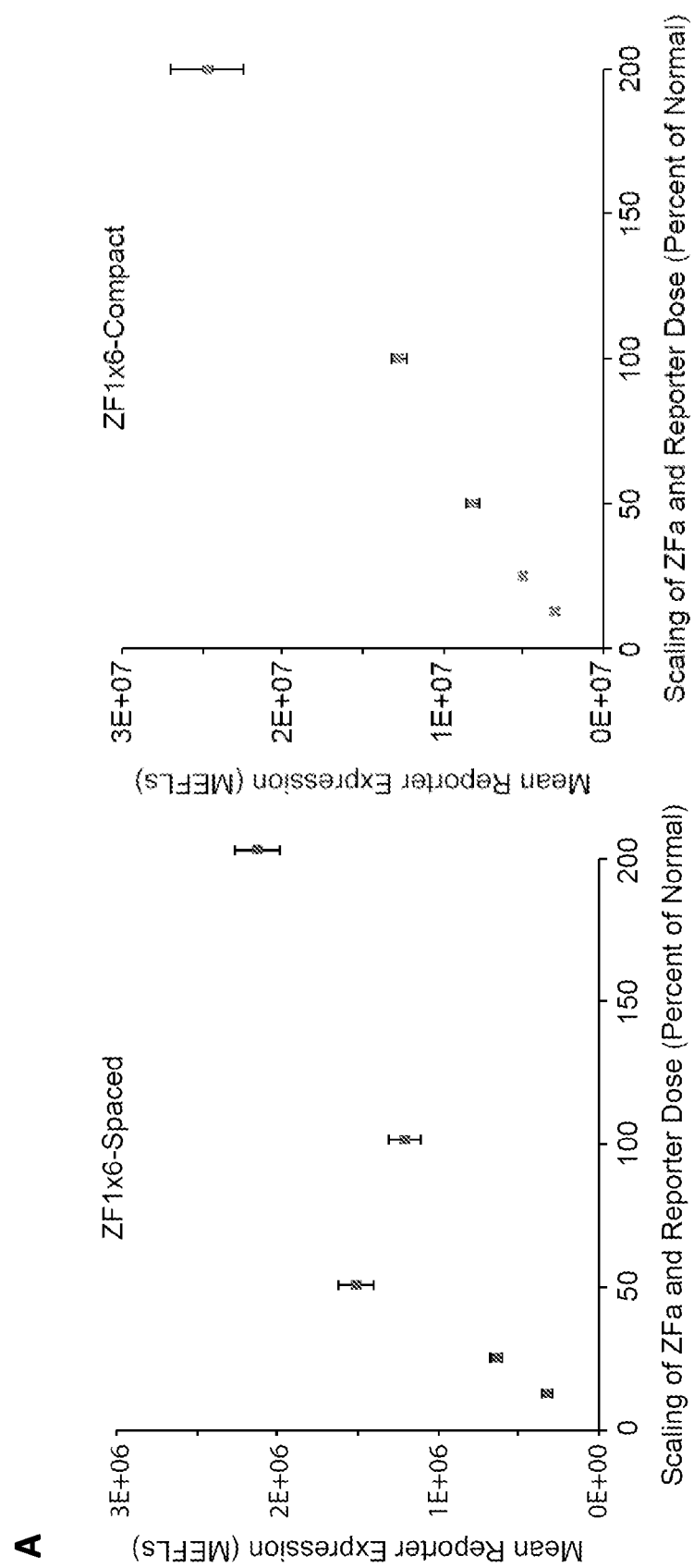
FIG. 9. Exploring the upper bound of EYFP expression. (A) Cells were transfected with ZFa43 and the 43×6-Spaced (left) or 43×6-Compact (right) reporter plasmids. (B) A statistical model for cell heterogeneity enables more accurate representations of genetic circuit behavior. The in silico population has 200 cells and up to six plasmids. Left: marginal distributions show intercellular variation in the relative expression of each gene. Right: pairwise correlations show intracellular variation in the relative expression of each gene. (C) Effects of the number and spacing of binding sites and the ZFa dose. Upper: reporter expression depends sigmoidally on the number of binding sites. Middle: the sigmoidal response to the number of binding sites holds across ZFa plasmid doses. Lower: the concave response to ZFa dose holds across the number and spacing of binding sites. (D) Predicted dose responses for ZFa that vary in m or w (rows), and differences between the mean cell and population mean (columns) (E) Flow cytometric and simulated distributions of reporter expression for different ZF1a doses and numbers of binding sites. Simulated reporter expression is in internally consistent a.u., and is linearly scaled to align with experiment-specific MEFLs.
Figure 9:
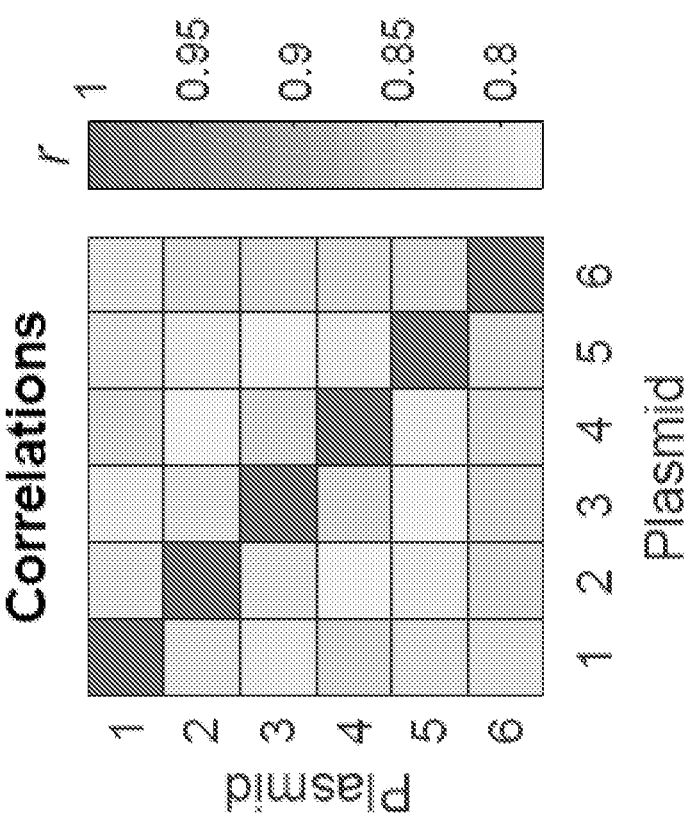
Figure 9:
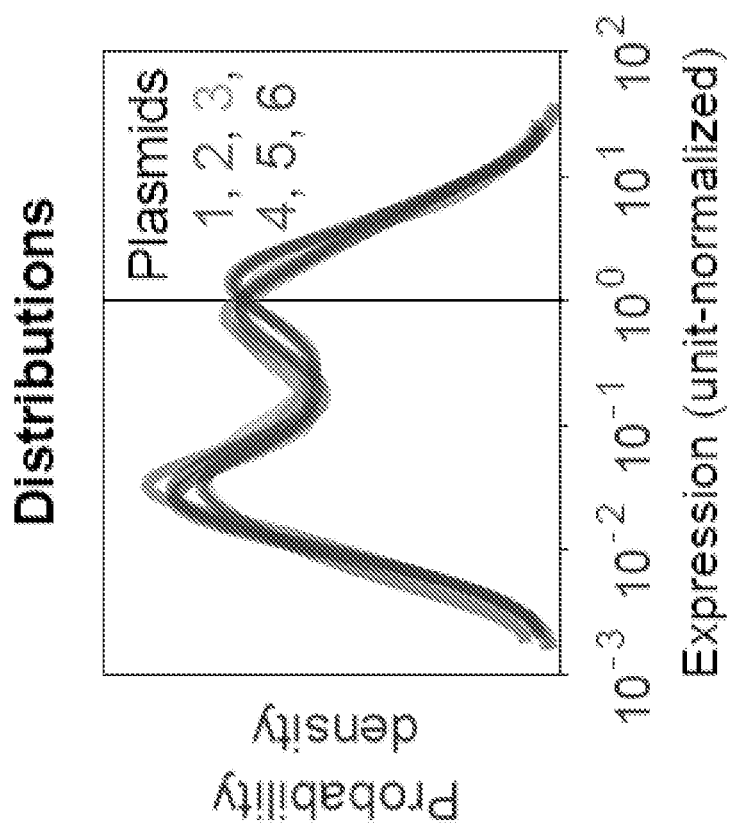
Figure 9:
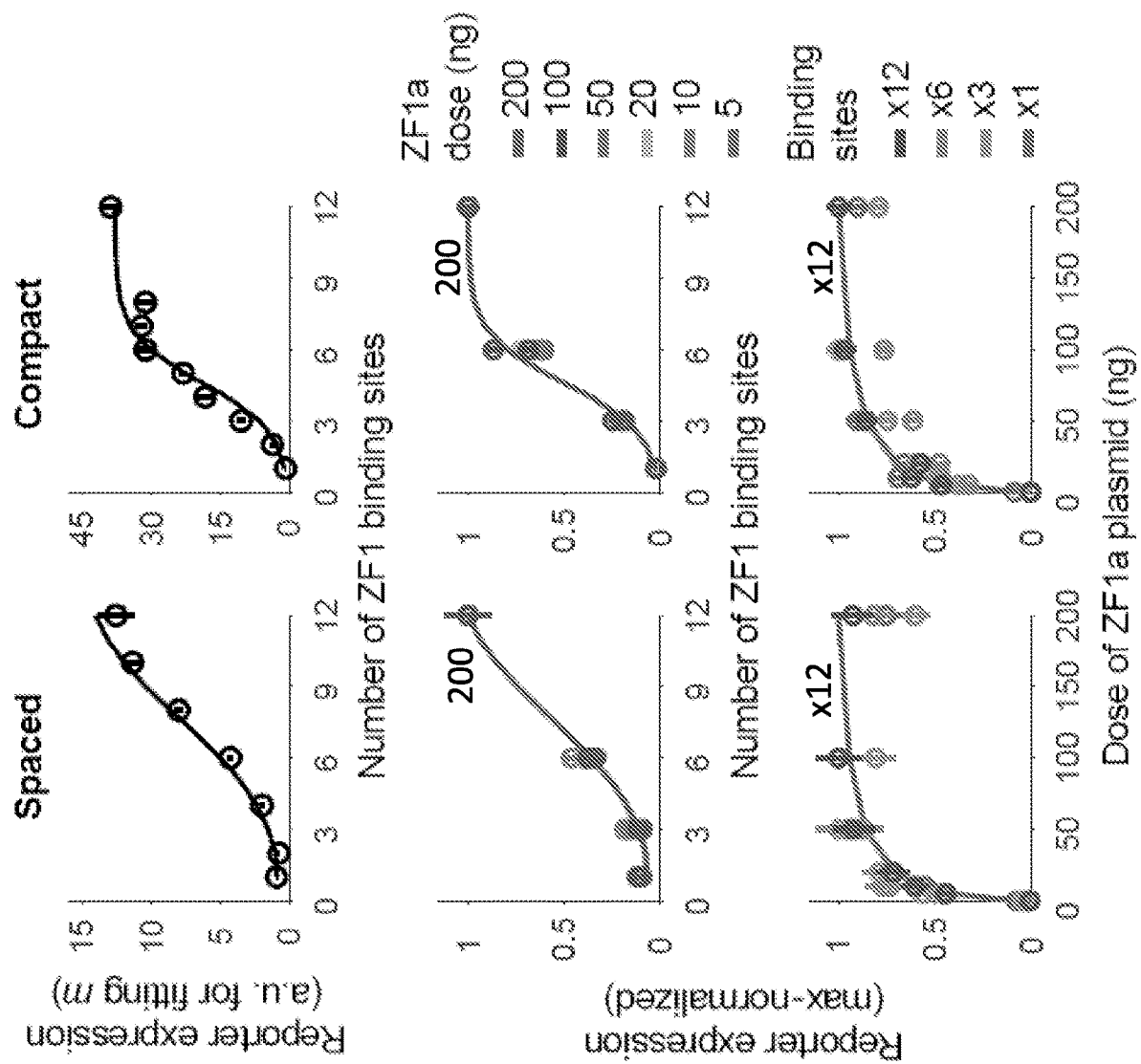
Figure 9:
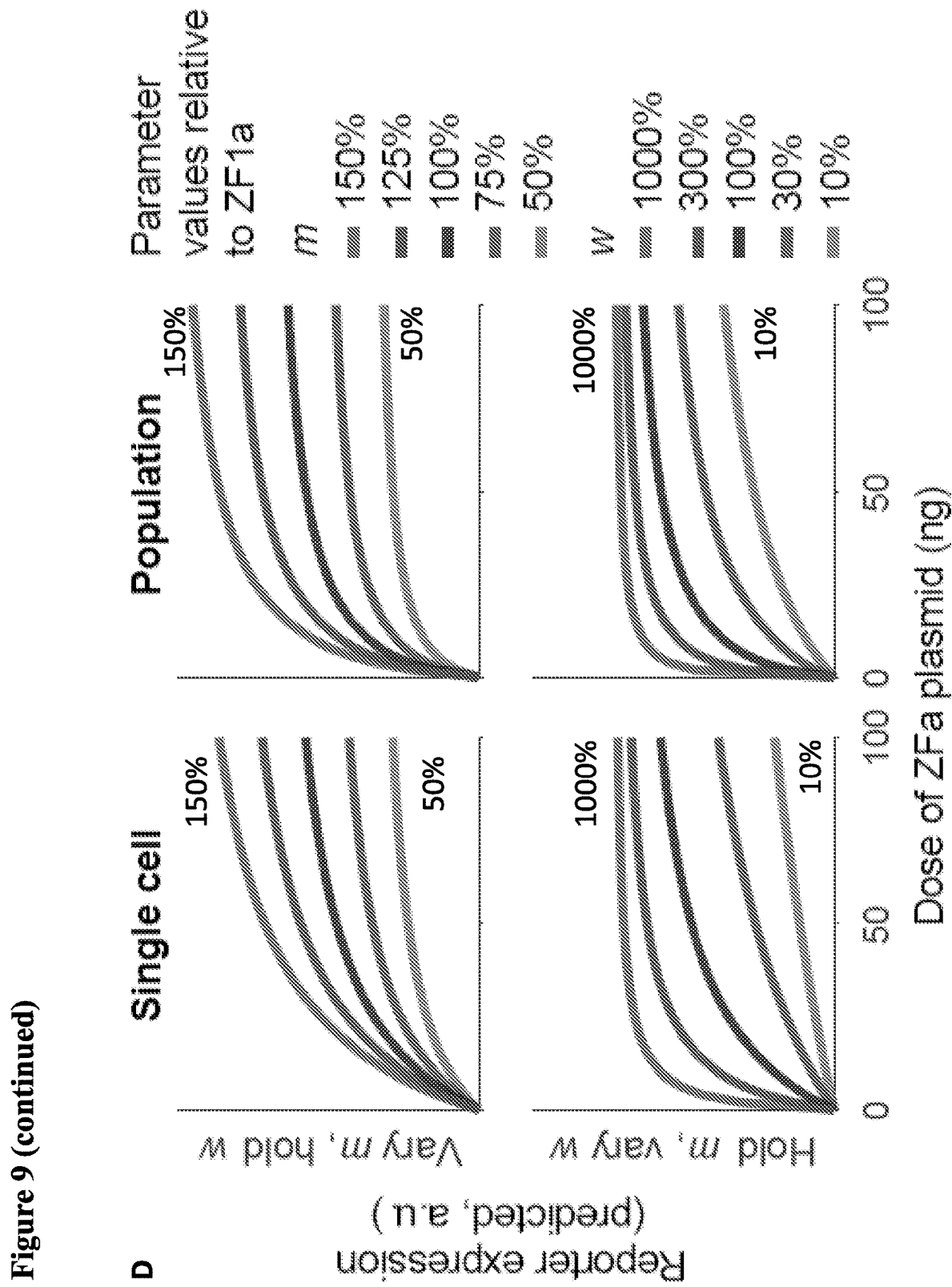
Figure 9:
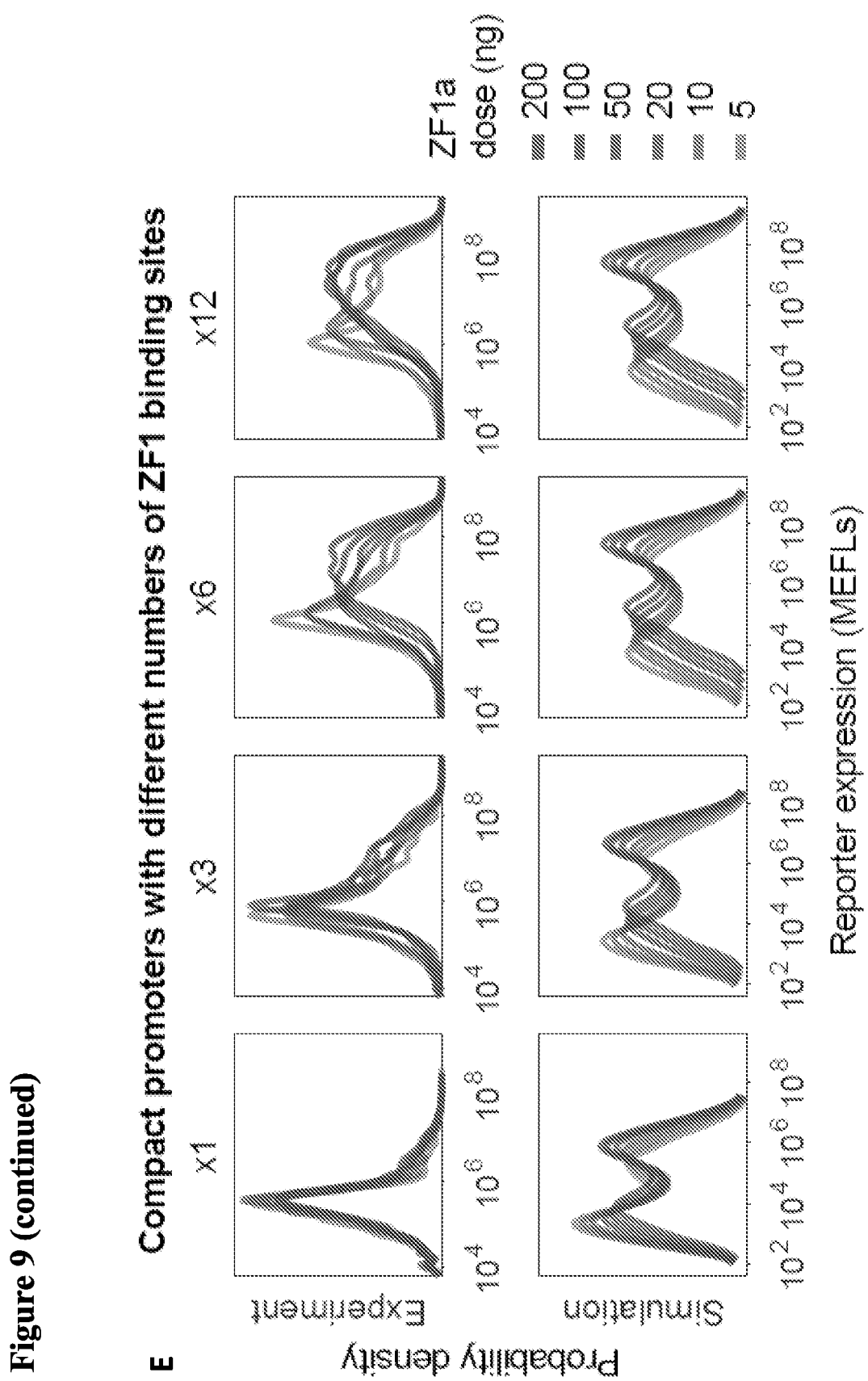

Exploring the upper bound of EYFP expression. Cells were transfected with ZFa43 and the 43×6-Spaced or 43x6-Compact reporter plasmids. (See FIG. 9A). These two plasmids were maintained at a constant ratio of 1:2 (ZFa:Reporter) while the total doses of plasmids were scaled (100% on the x-axis represents 100 ng of ZFa43 plasmid and 200 ng of reporter plasmid). In previous experiments, most reporter constructs were in the plateau range of their dose-response profile at the 100% dose; however, doubling the amount of ZFa when the amount of plasmid was also doubled resulted in a continuation of the linear range of gene expression. This indicates that the amount of plasmid was the limiting factor in gene expression, i.e., the ZFa induced as much expression from those plasmids as the VP16 AD could.

Statistical Model for Cell Heterogeneity

We also generated a statistical model for cell heterogeneity in order to provide a more accurate representation of genetic circuit behavior. (See FIG. 9B).

Effects of the number and spacing of binding sites and the ZFa dose. Upon max-normalization of the landscape cross-sections from FIG. 2A, data series collapse onto the same profile—a notable feature of COMET that differs from other TFs in general.

Predicted Dose Responses for ZFa. We assessed reporter expression versus dose of ZFa. (See FIG. 9D). Since heterogeneity tends to inflate the outcomes, a model fitted using a standard homogeneous approach would overestimate parameter values, whereas an approach that appropriately accounts for heterogeneity is more accurate.

Flow cytometric and simulated distributions of reporter expression for different ZF1a doses and numbers of binding sites. We studied flow cytometric distribution and a model of simulated distribution of reporter expression for different ZF1a doses and numbers of binding sites. The model captures the observation of bimodal log-Gaussian distributions, and that at increasing ZFa doses the probability density shifts from the lower mode to the upper mode. We note that in experiments, bimodality is less apparent with promoters that have a low number of binding sites due to limited resolution of the flow cytometer in the low fluorescence range.

Figure 10:
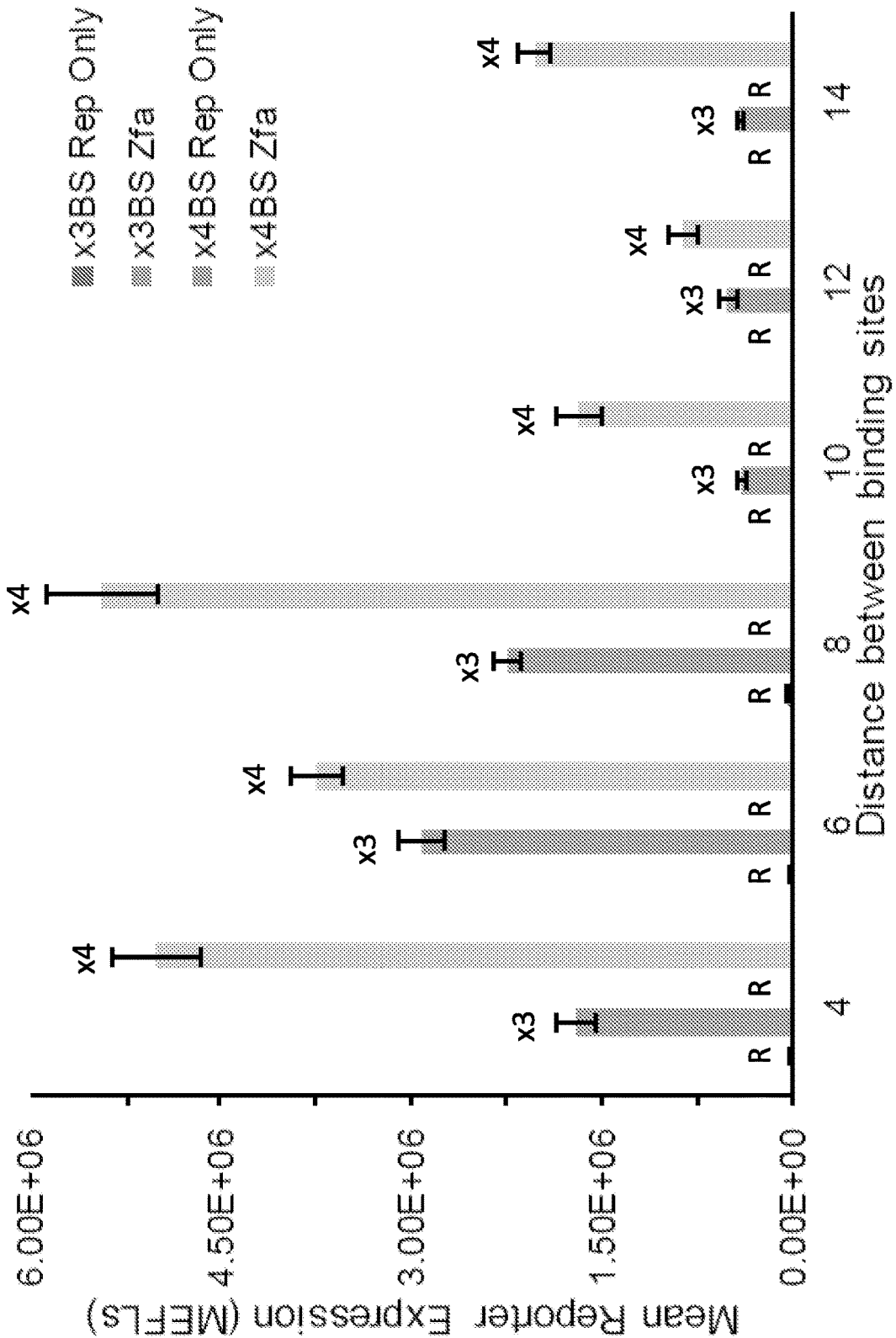
FIG. 10. Assessing distance between binding sites.

Distance between binding sites. Constructs with either 3 or 4 binding sites in the promoter and a varying number of base pairs were transfected into cells with and without ZFa. (See FIG. 10). In all cases, the 4 binding site promoter led to more gene expression than the 3 binding site promoter. This suggests that the decrease in gene expression from 3 binding sites to 4 binding sites seen in FIG. 3C was due to the nucleotide sequence of the DNA in between the binding sites rather than the distance between the binding sites.

Mutations that alter ZF affinity for the DNA modulate the m and w parameters. Mutations that alter ZF affinity for the DNA modulate the m and w parameters in the equation $m=7.3\times10^2 w+8.6$, $R^2=0.87$. (See FIG. 11A). Correlation in values for the ZF1a mutants reveals a single axis for ZF1a strength. Flow plots for expression versus binding sites for each R/A variant is provided in FIG. 11B and FIG. 11C. The wild type and four ZFa affinity mutants were transfected with compact promoters containing varying numbers of binding sites. The mutant ZFa did not display squelching at higher doses of ZFa, unlike the WT.

Figure 11:
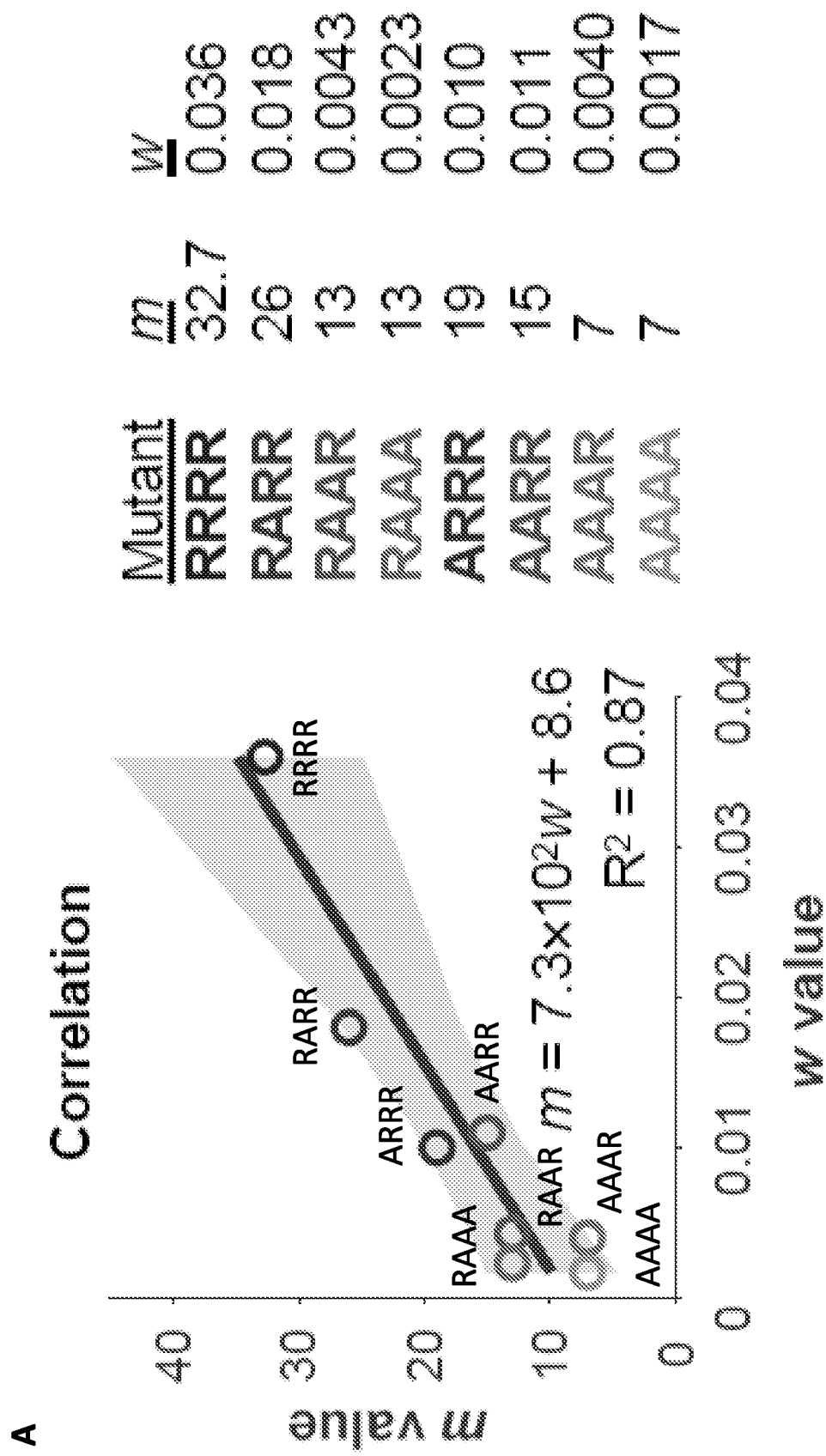
FIG. 11. Assessing mutations that alter ZF affinity. (A) Mutations that alter ZF affinity for DNA modulate the m and w parameters. Correlation in values for the ZF1a mutants reveals a single axis for ZF1a strength. The 95% confidence interval for the regression line is indicated by the shaded region. (B) (C) Properties of ZFa mutants. The wild type and four ZFa affinity mutants were transfected with compact promoters containing varying numbers of binding sites. The mutant ZFa did not display squelching at higher doses of ZFa, unlike the WT (B). (C) Data from (B) is normalized to show the expression induced by the ZFa mutant relative to the WT for each promoter. (D) Activation domains VP16, VP64, and VPR fused to all 5 original ZFa. (E) Effects of varying the AD and ZF mutation.
Figure 11:
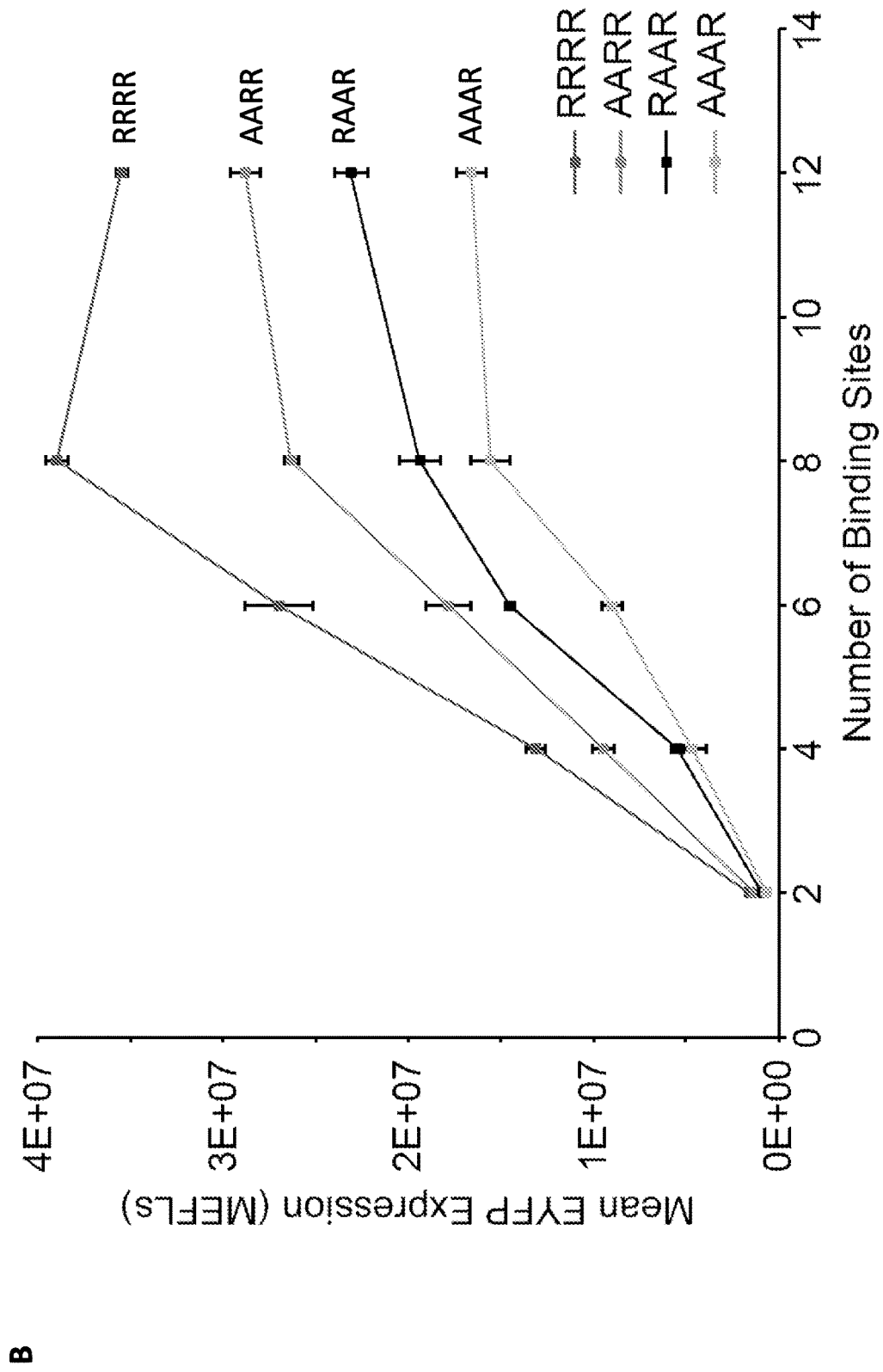
Figure 11:
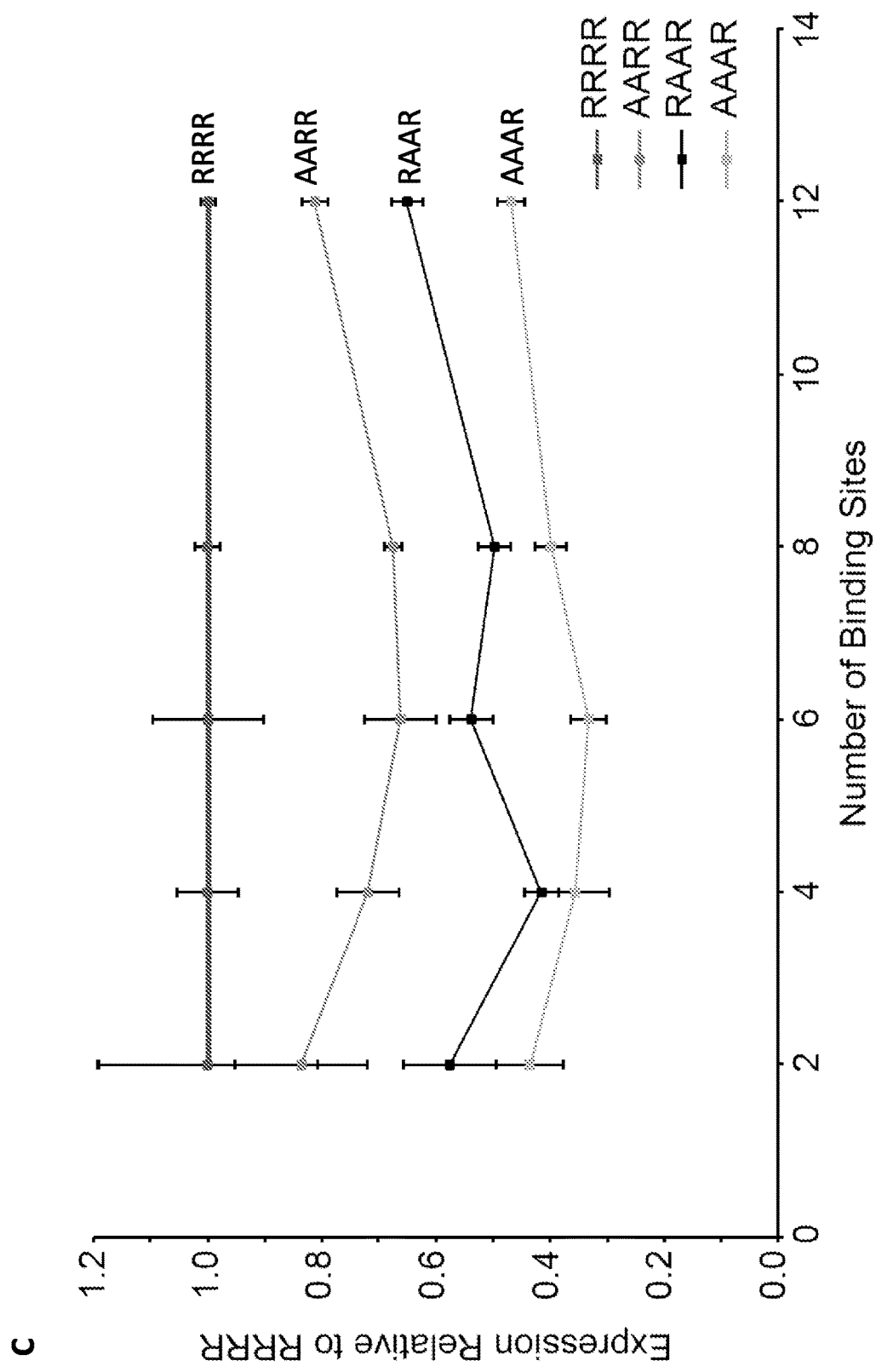
Figure 11:
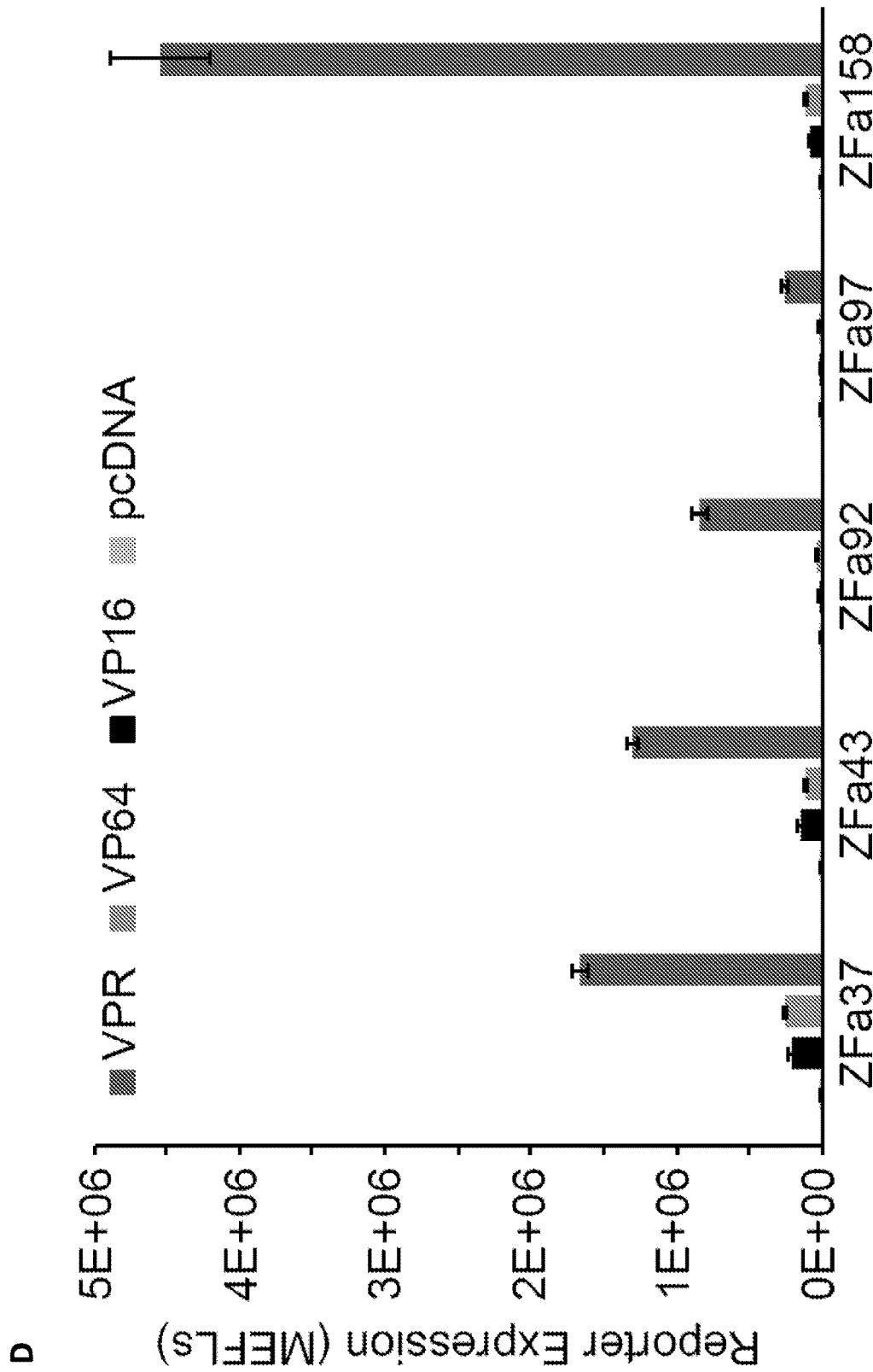
Figure 11:
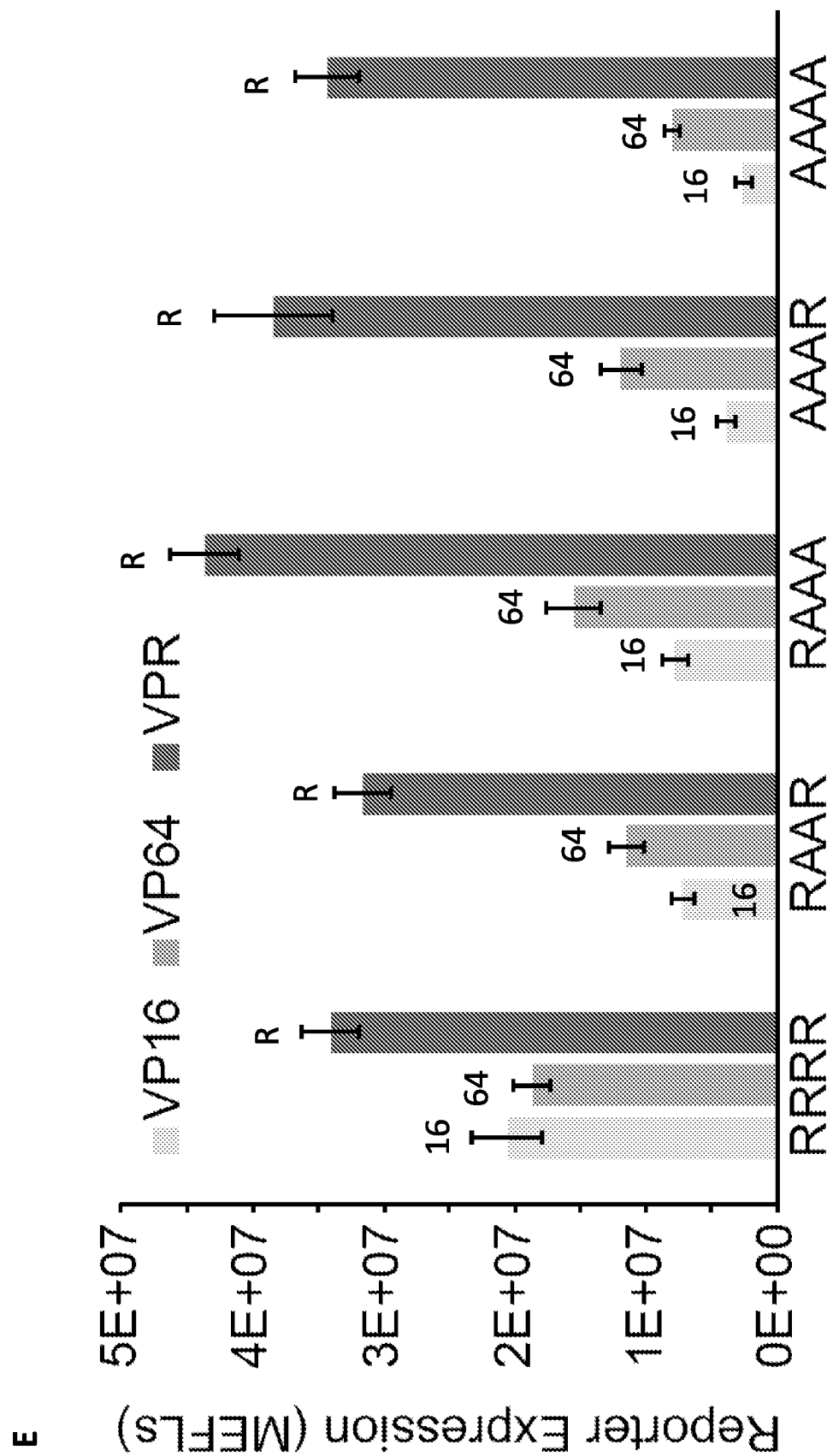

Effect of various activation domains. The effect of various activation domains fused to all 5 original ZFa is illustrated in FIG. 11D. VP16, VP64, and VPR were fused to the original panel of five ZFa and transfected with their cognate 1 binding site reporter. VPR led to higher expression than VP16, while VP64 either had no or a small impact compared to VP16.

Effects of varying AD and ZF R/A mutations. Effects of varying AD and ZF R/A mutations are illustrated in FIG. 11E. VP16, VP64, and VPR fused ZFa with various affinity mutations were transfected at 100 ng per well (a saturating or near-saturating dose for each). Unlike for the WT ZFa, the VP64 fusion resulted in more expression than VP16, for each mutant. VPR again led to the highest expression for each ZFa tested, with all ZFa-VPR fusions resulting in expression as high as or higher than the WT ZFa-VPR fusion.

Figure 12:
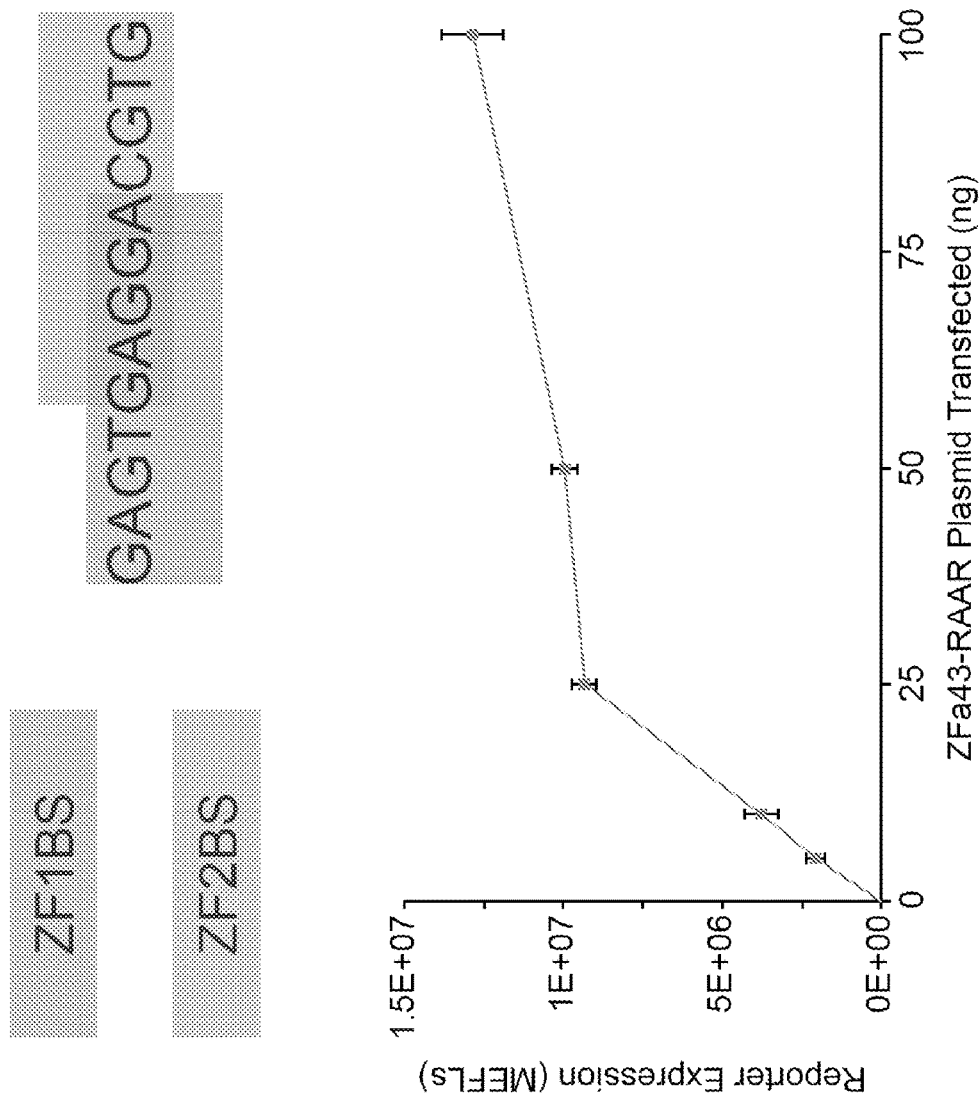
FIG. 12. (A) Hybrid reporter schematic and activation profile. (B) (C) Dose-response of zinc finger inhibitors. (D) ZFi inhibit gene expression in a similar pattern at high doses. Data presented on the Top and the right are from the same experiment; the panel on the Bottom is zoomed in to more clearly show the differences between the low levels of gene expression. (E) A model for regulation of target gene expression using greater mechanistic detail than the m-w ZF-TF model. Reversible association and dissociation reactions (lines) occur between different components (color-coded). The DNA variable represents a reporter gene with a single ZF binding site. The variables ZFi and free AD are expected to form non-productive complexes with DNA and RNAP, respectively. The DNA.TF.RNAP variable at steady state is a proxy for reporter expression. (F) The abundance and/or properties of ZFa, ZFi, and free AD. Arrows emphasize the diagonal tuning. (G) The predicted effect of the inhibitor. Arrows emphasize the diagonal tuning.
Figure 12:
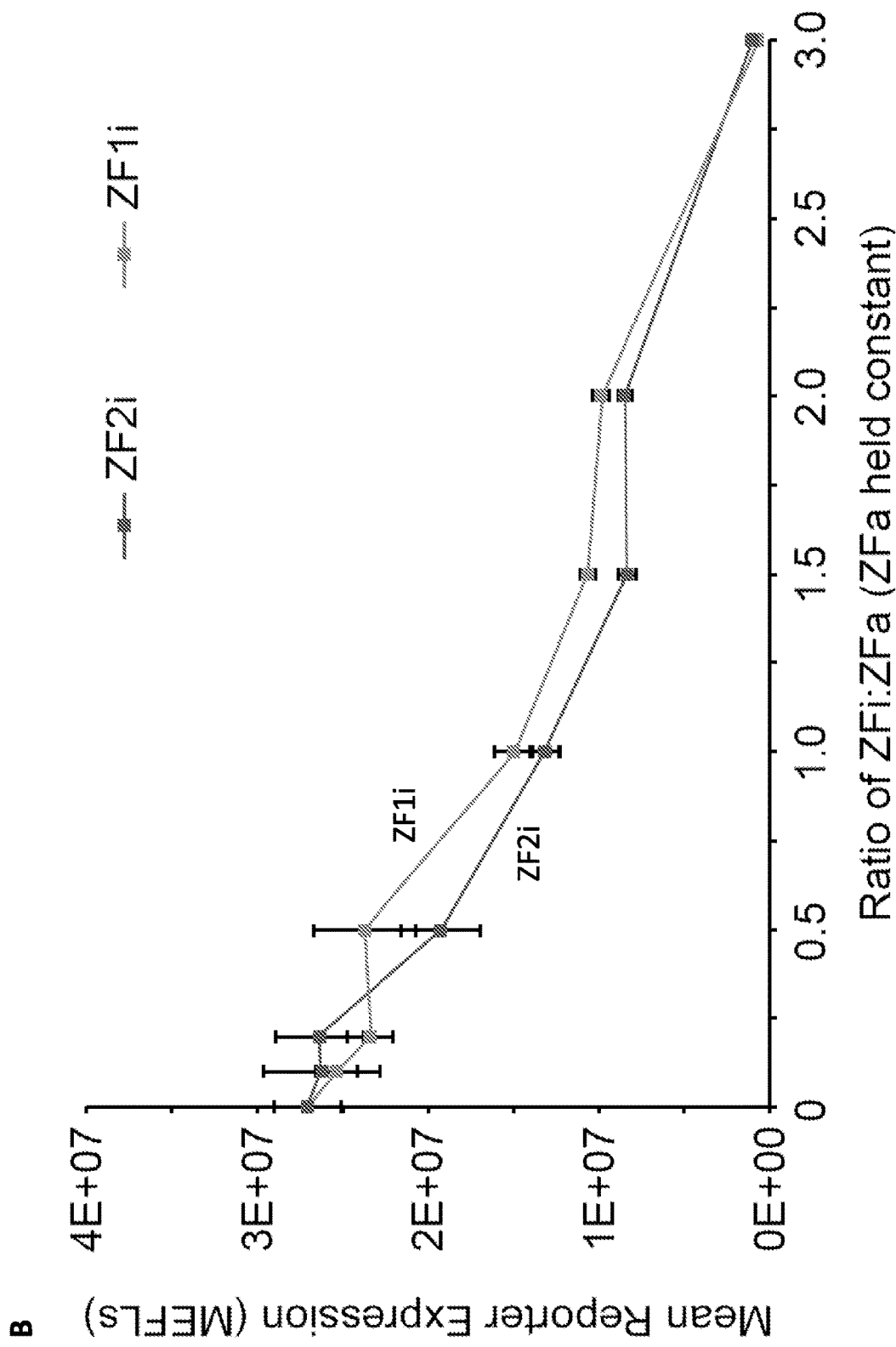
Figure 12:
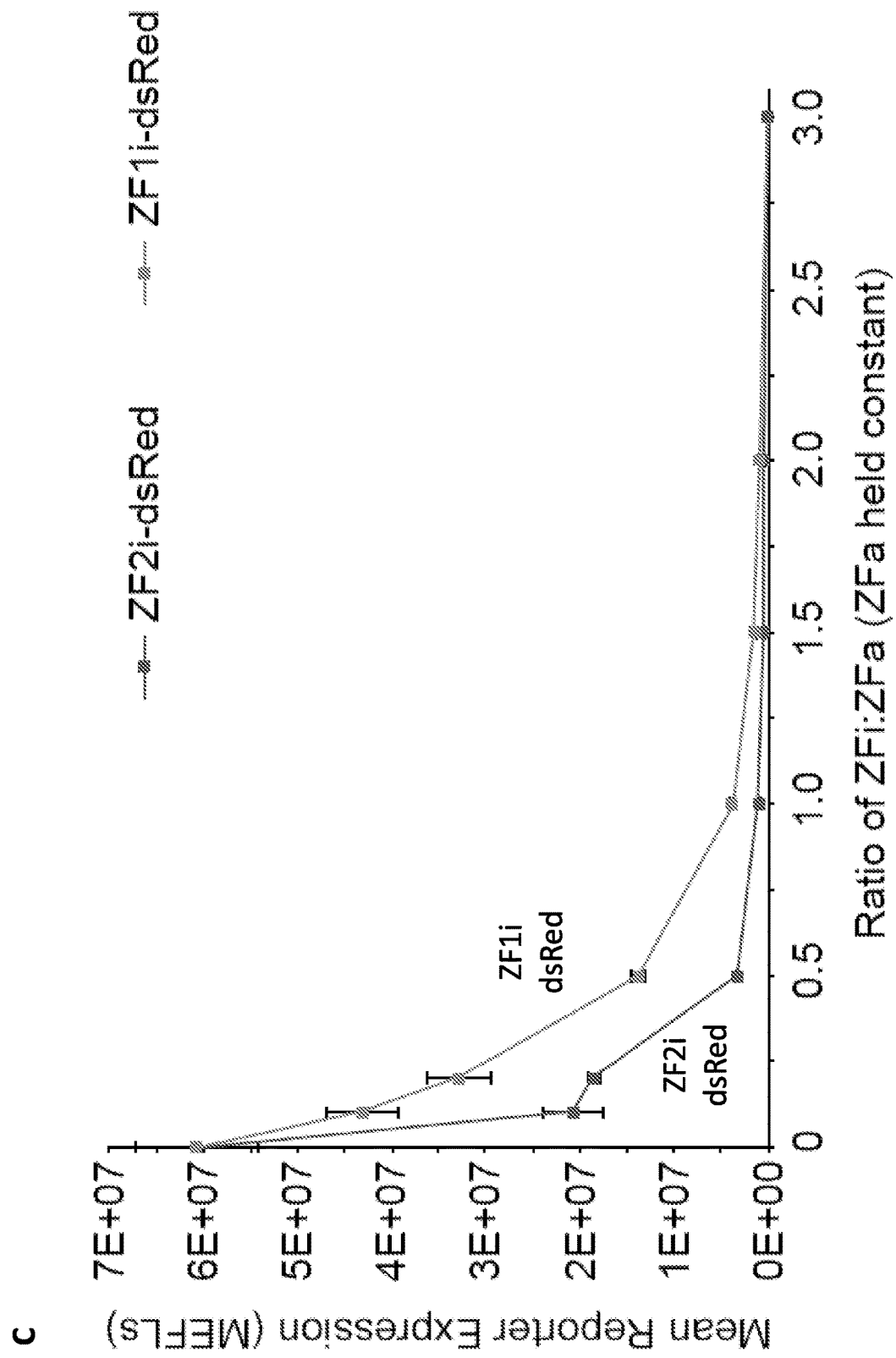
Figure 12:
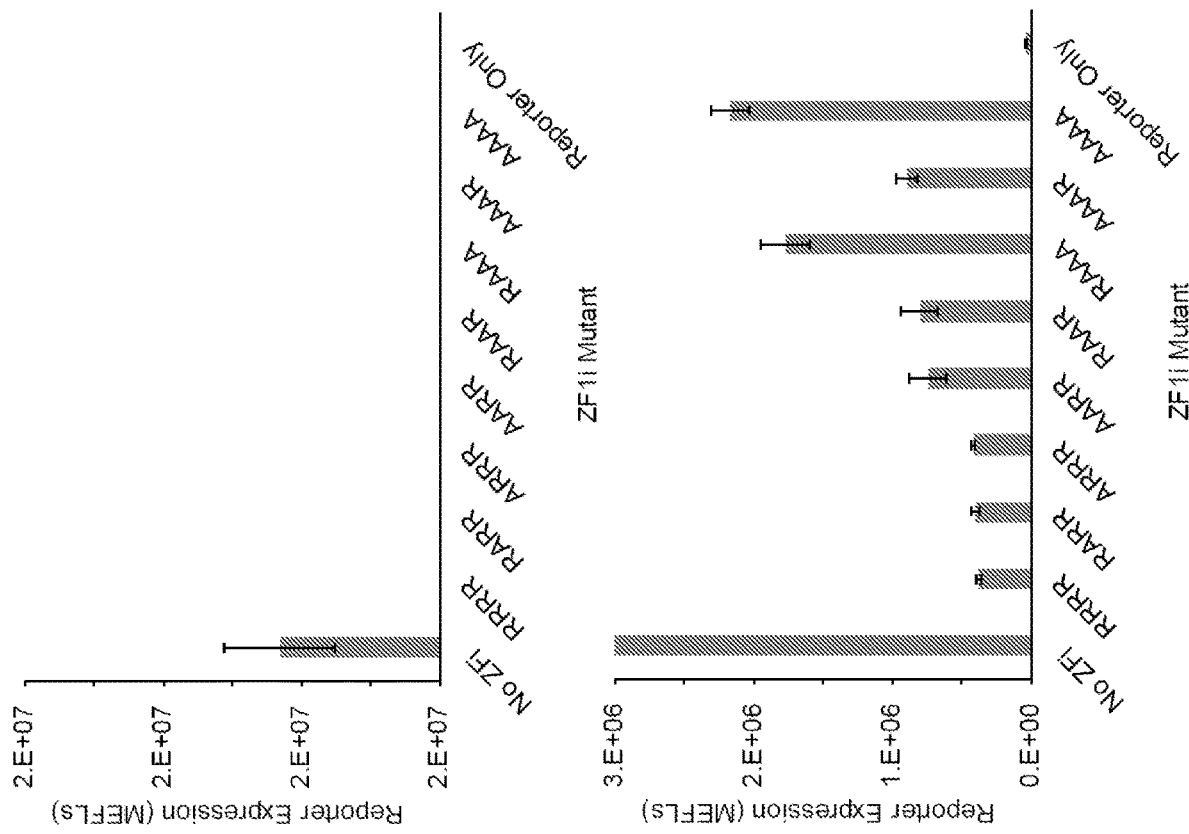
Figure 12:
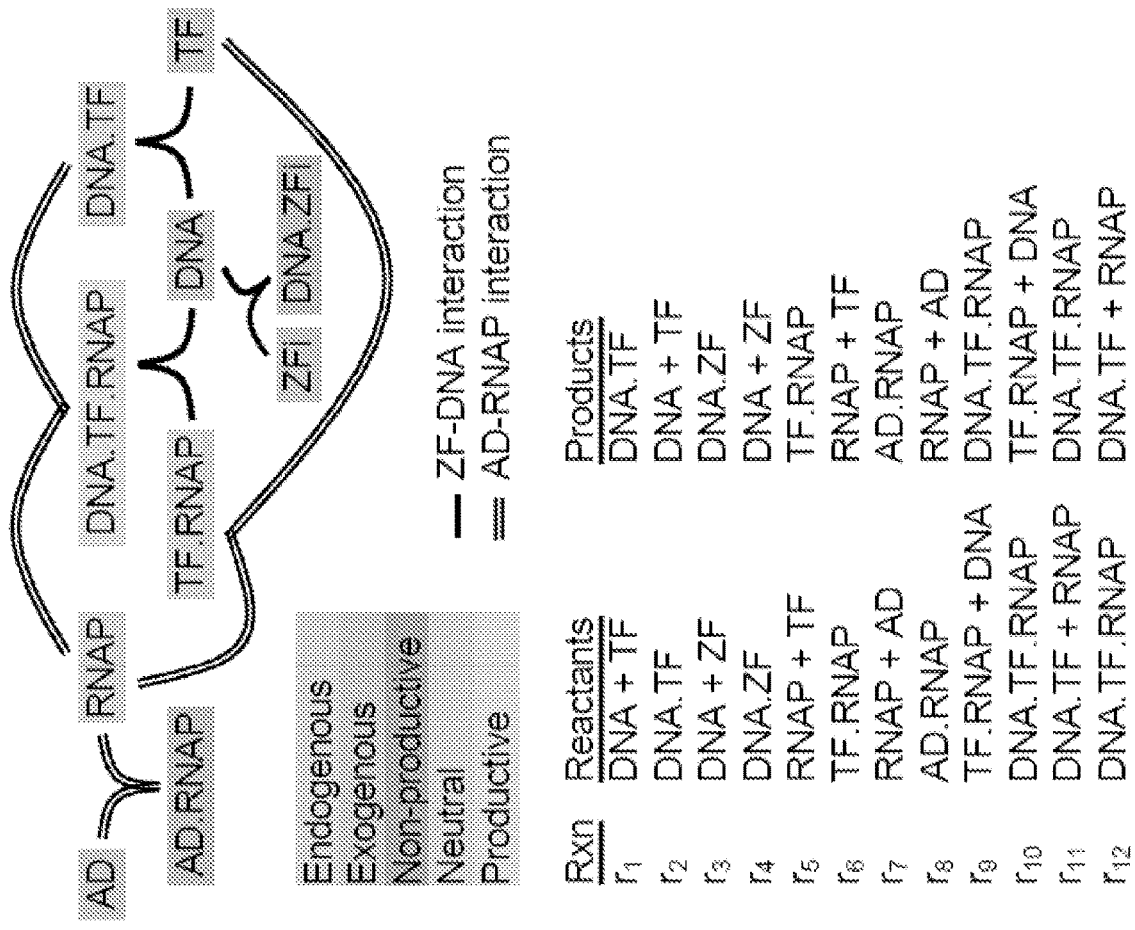
Figure 12:
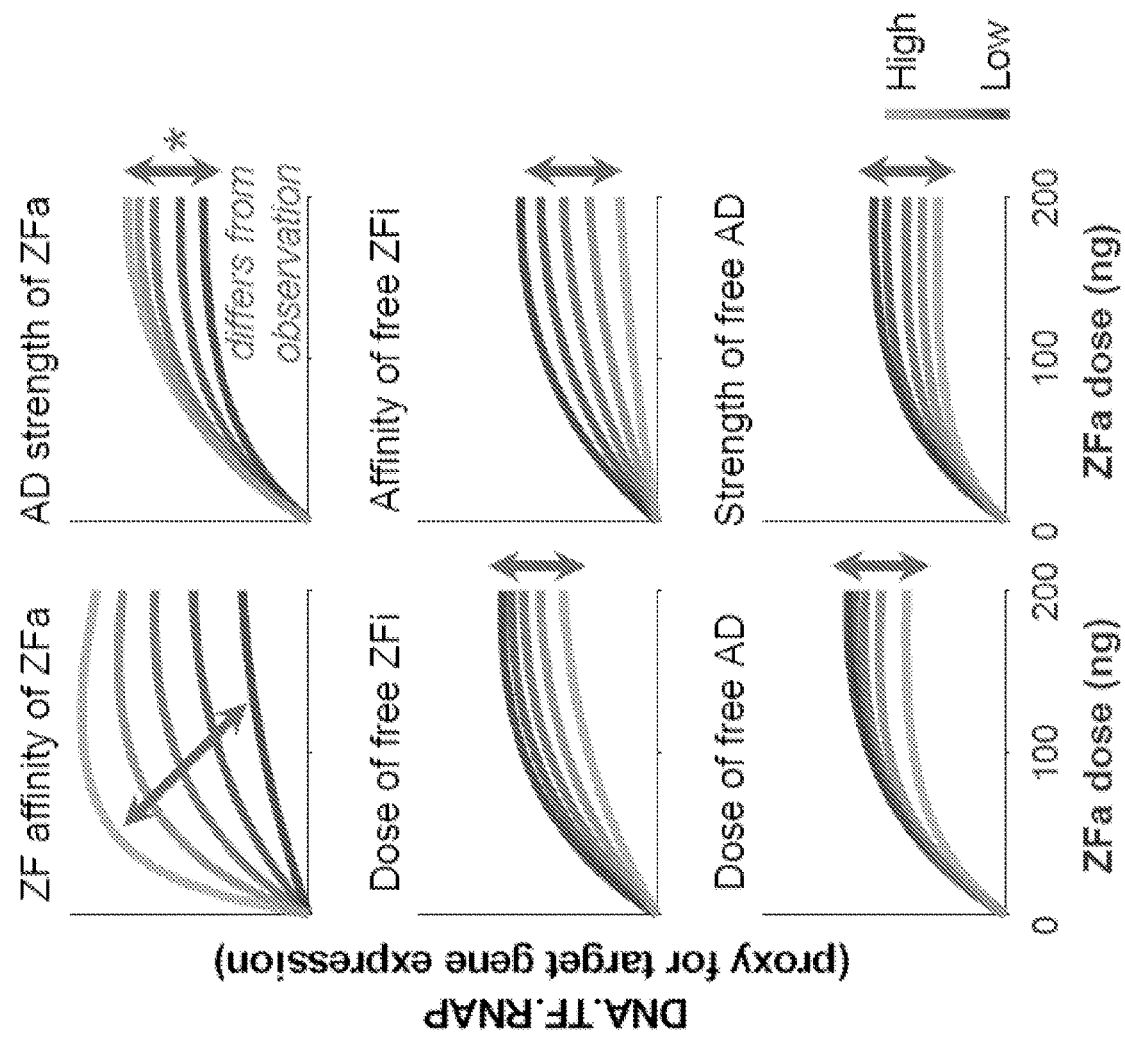
Figure 12:
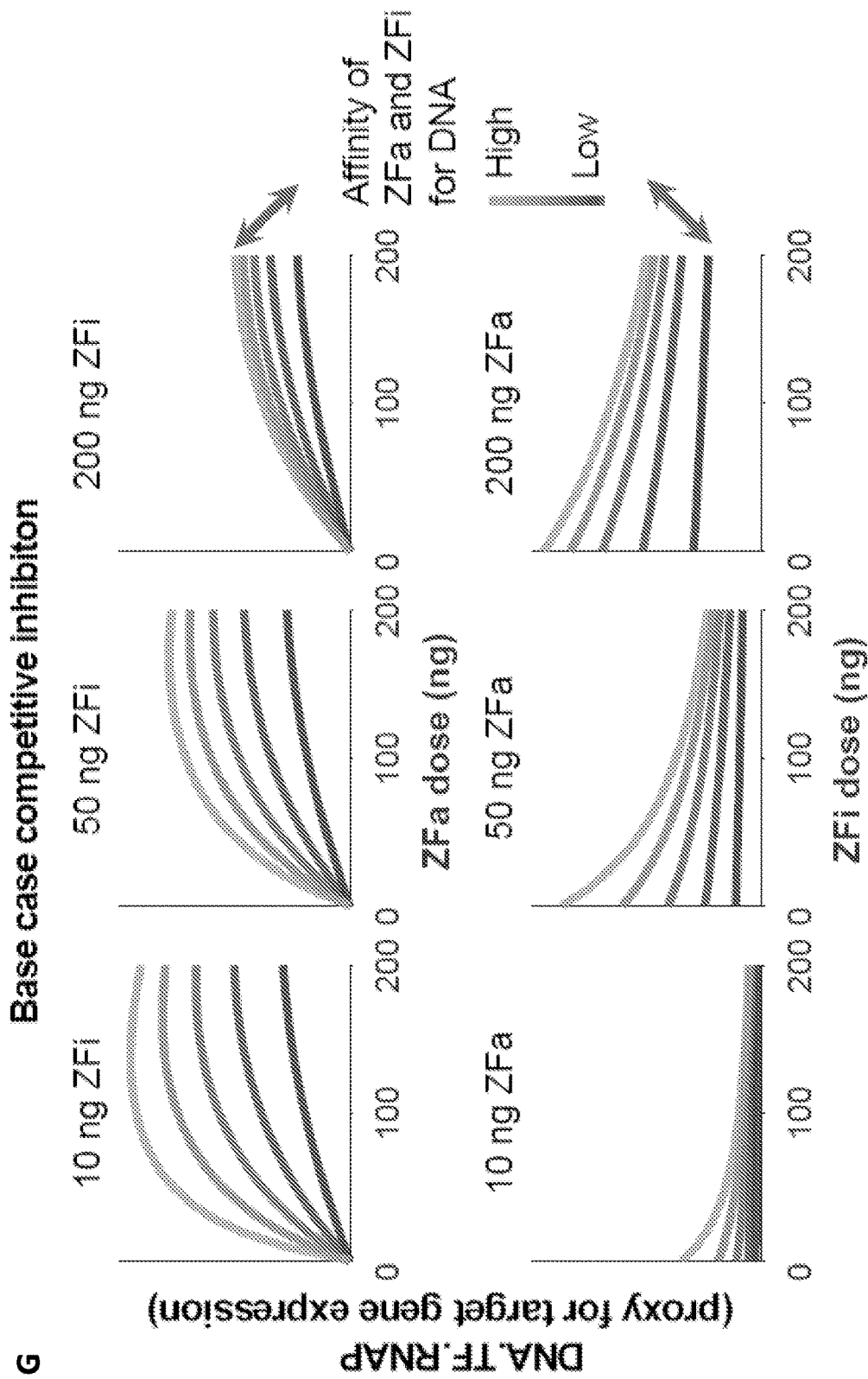

Hybrid Promoter Schemes. FIG. 12A illustrates a hybrid reporter schematic and activation profile. The last 5 nucleotides of the ZF1 binding site are the same as the first 5, allowing a hybrid reporter to be constructed by arranging 6 binding sites for ZF1 to be constructed with 6 base pairs of spacing in between each, where the first four base pairs are the last four base pairs of the ZF2 binding site. On the right, the dose response profile for ZF1a (with the RAAR affinity mutations) on the hybrid reporter, which resembles the profile on the 43×6-Compact reporter in FIG. 2A. A flow cytometry plots from FIG. 5A is also provided in FIG. 12A.

Dose-response of zinc finger inhibitors. The dose-response of zinc finger inhibitors is illustrated in FIG. 12B. In these experiments, the doses of ZFa and reporter plasmid were held constant, while the dose of ZFi was increased. For null ZFi, there was no difference in repression between the overlapping ZF2i or same ZF1i. (See FIG. 12C). ZF2i-dsRed was a stronger repressor than ZF1i-dsRed. (See FIG. 12C). ZFi were observed to inhibit gene expression in a similar pattern at high doses. (See FIG. 12D). ZFi were transfected with ZFa at a 10:1 ratio and were observed to follow the same pattern seen at a 1:1 transfection ratio.

Model for Regulation of Target Gene Expression. A model for regulation of target gene expression using greater mechanistic detail than the m-w ZF-TF model is provided in FIG. 12E.

Abundance and/or Properties of ZFa, ZFi, and free AD. The abundance and/or properties of ZFa, ZFi, and free AD are predicted to have the effects shown in FIG. 12F. While the predicted "diagonal" tuning effect of ZFa affinity qualitatively agrees with experimental observations, the effect of AD strength of the ZFa does not (experiments show it also has a diagonal effect). This lack of agreement reinforces the TF cooperativity on RNAP recruitment inferred in FIG. 2A and FIG. 2B. We note that at very high dose and affinity of ZFa, a non-monotonic dose response phenomenon called squelching is predicted, in which the formation of TF.RNAP and DNA.TF occurs at the expense of DNA.TF.RNAP. In FIG. 12G, the predicted effect of the inhibitor on a single-site reporter is shown as if it were purely competitive, and did not decrease the effective ZF-TF cooperativity.

Cause of Rapamycin-independent Signaling for RaZF. We also investigated the cause of rapamycin-independent signaling for rapamycin inducible transcription factors (RaZF). VPR-FRB was transfected alone, with FKBP-ZF, ZF only, or ZFi-dsRed and a 43×6-Compact reporter, in the presence or absence of rapamycin results are presented in FIG. 13A. VPR-FRB induced some expression from the reporter even when transfected alone. However, the amount of gene expressed induced by VPR-FRB in the absence of rapamycin increased when either FKBP-ZF or ZF1i were included in the transfection. This could possibly be due to chance collisions between the promoter and VPR-FRB that is pre-loaded with transcriptional complex, resulting in a small amount of expression. It increases in the presence of ZF because the ZF-bound DNA is more accessible. The effect is negated in the presence of ZF1i-dsRed, which can block transcription from the promoter.

Requirement for Nuclear Localization Signal. We also investigated whether removing the nuclear localization signal (NLS) from the RaZF would affect function. To test whether excluding one or both components from the nucleus until rapamycin addition would decrease background signaling, the nuclear localization signal (NLS) was removed from each part. Results are presented in FIG. 13B. No consistent improvement in fold induction was seen by removing the NLS from either component.

Figure 13:
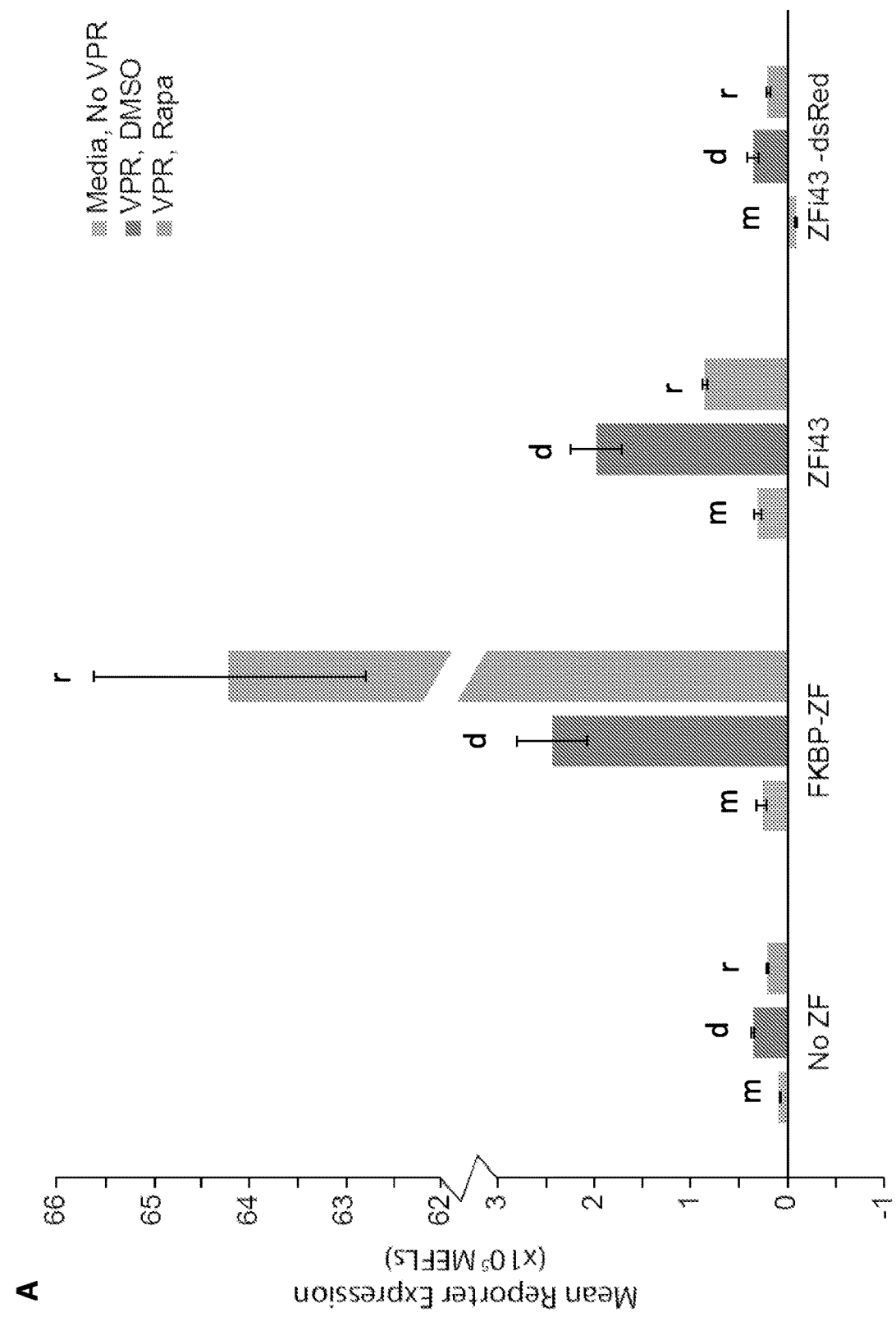
FIG. 13. (A) Investigating the cause of rapamycin-independent signaling for RaZF. (B) Removing the NLS from the RaZF. (C) (D) The effect of ratios of FKBP-ZF:AD-FRB on performance of VP64-RaZF and VPR-RaZF. (E) RaZF with all components expressed at a 1:5 FKBP-ZF:AD-FRB ratio.
Figure 13:
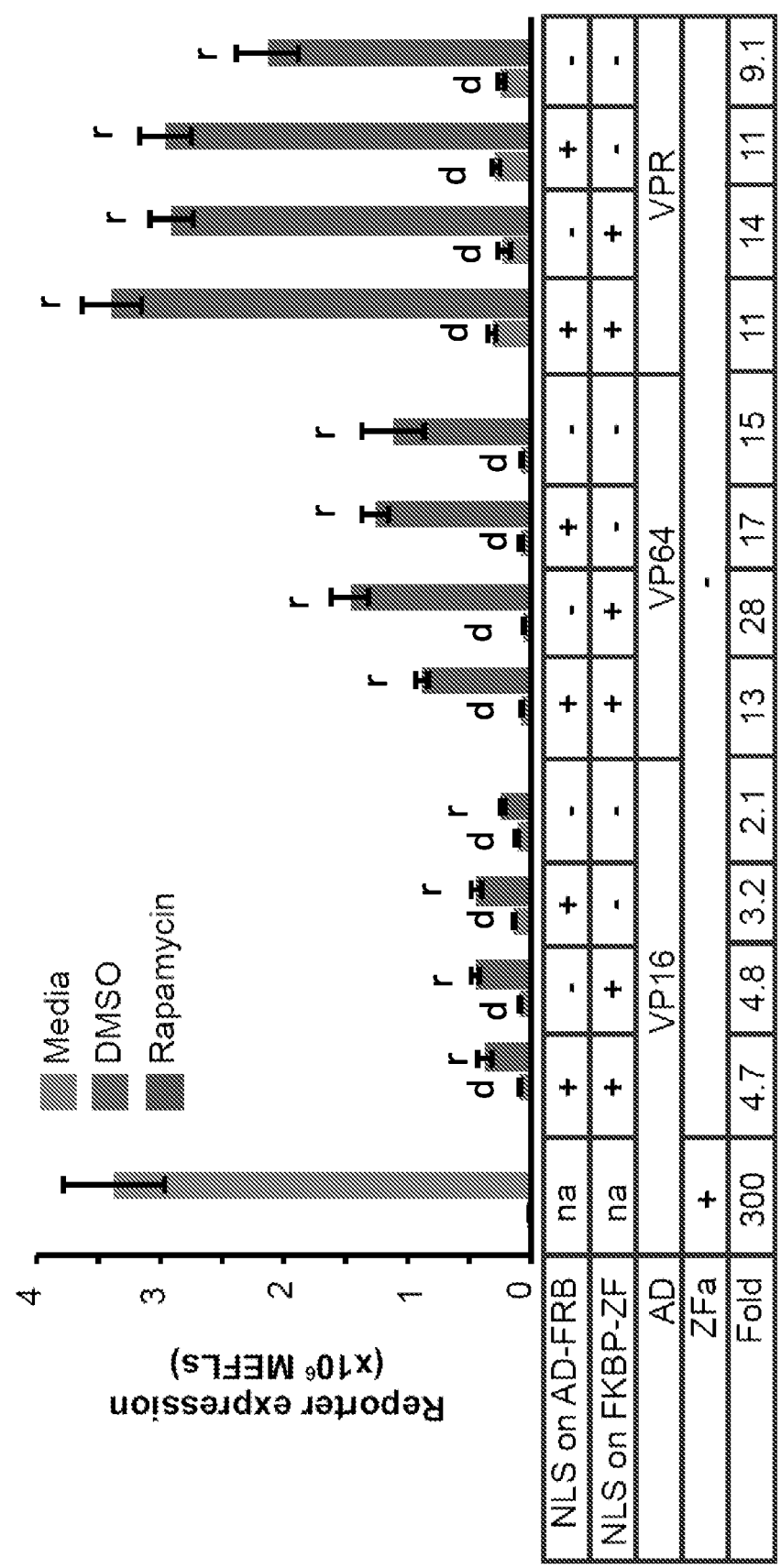
Figure 13:
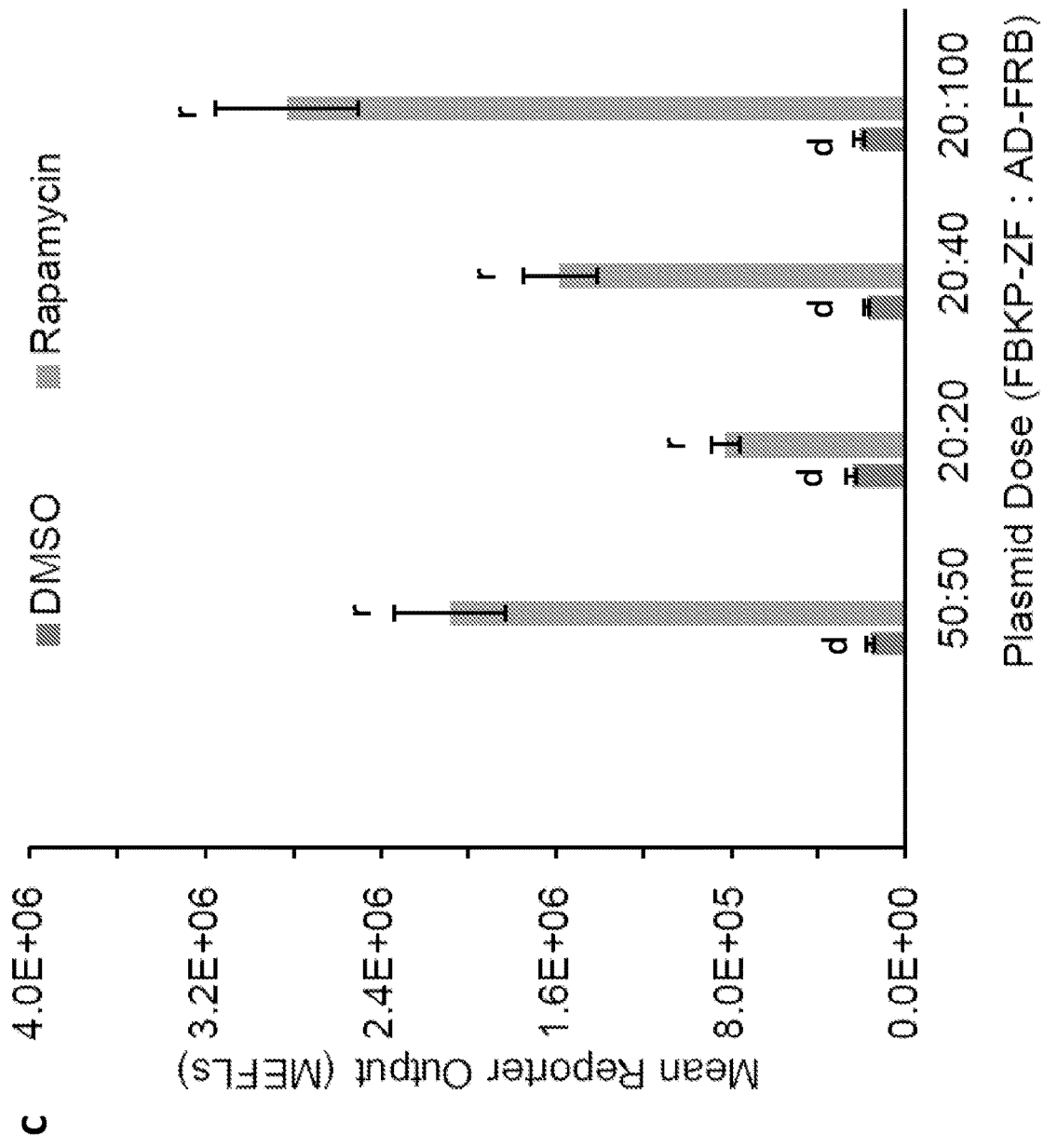
Figure 13:
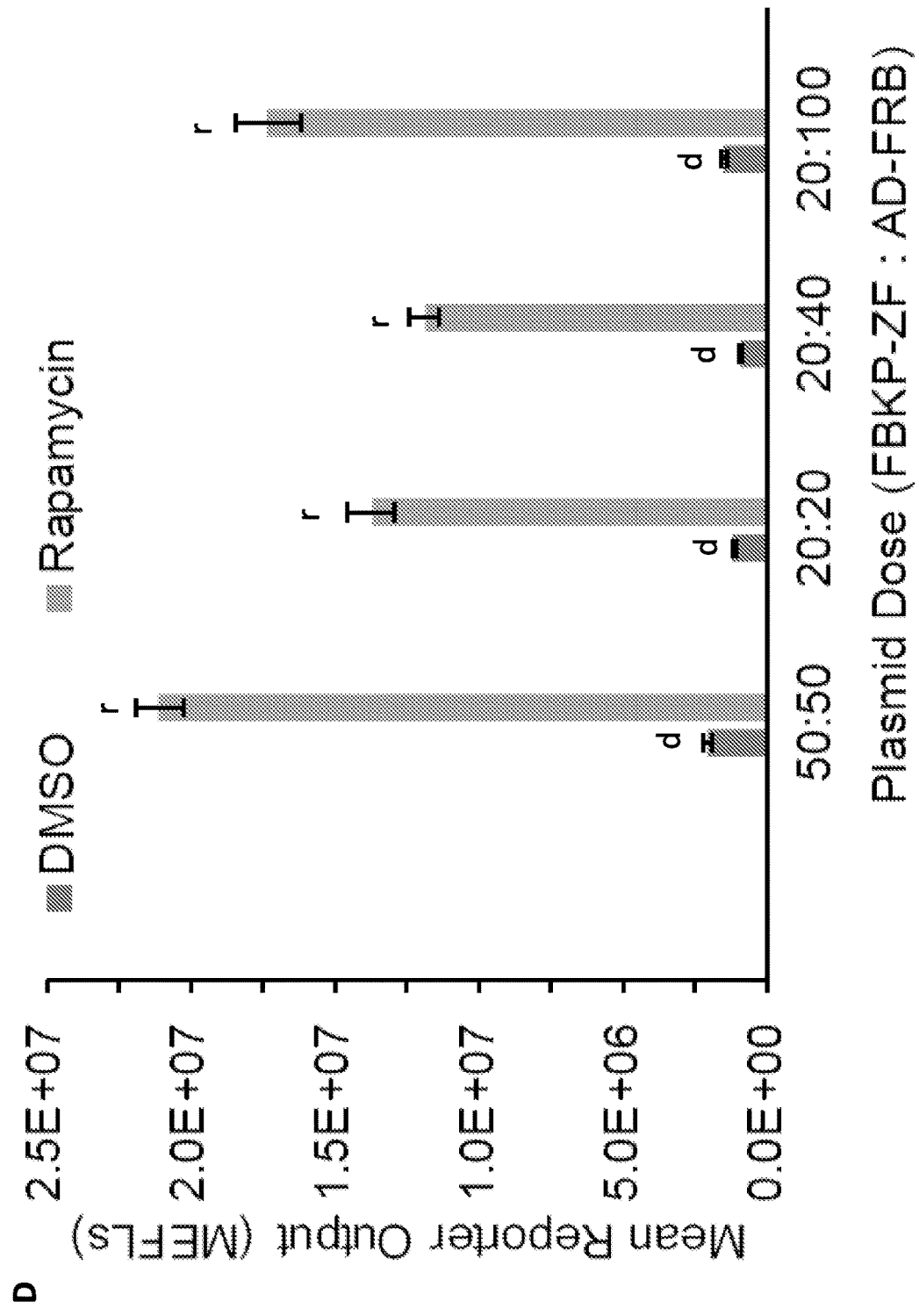
Figure 13:
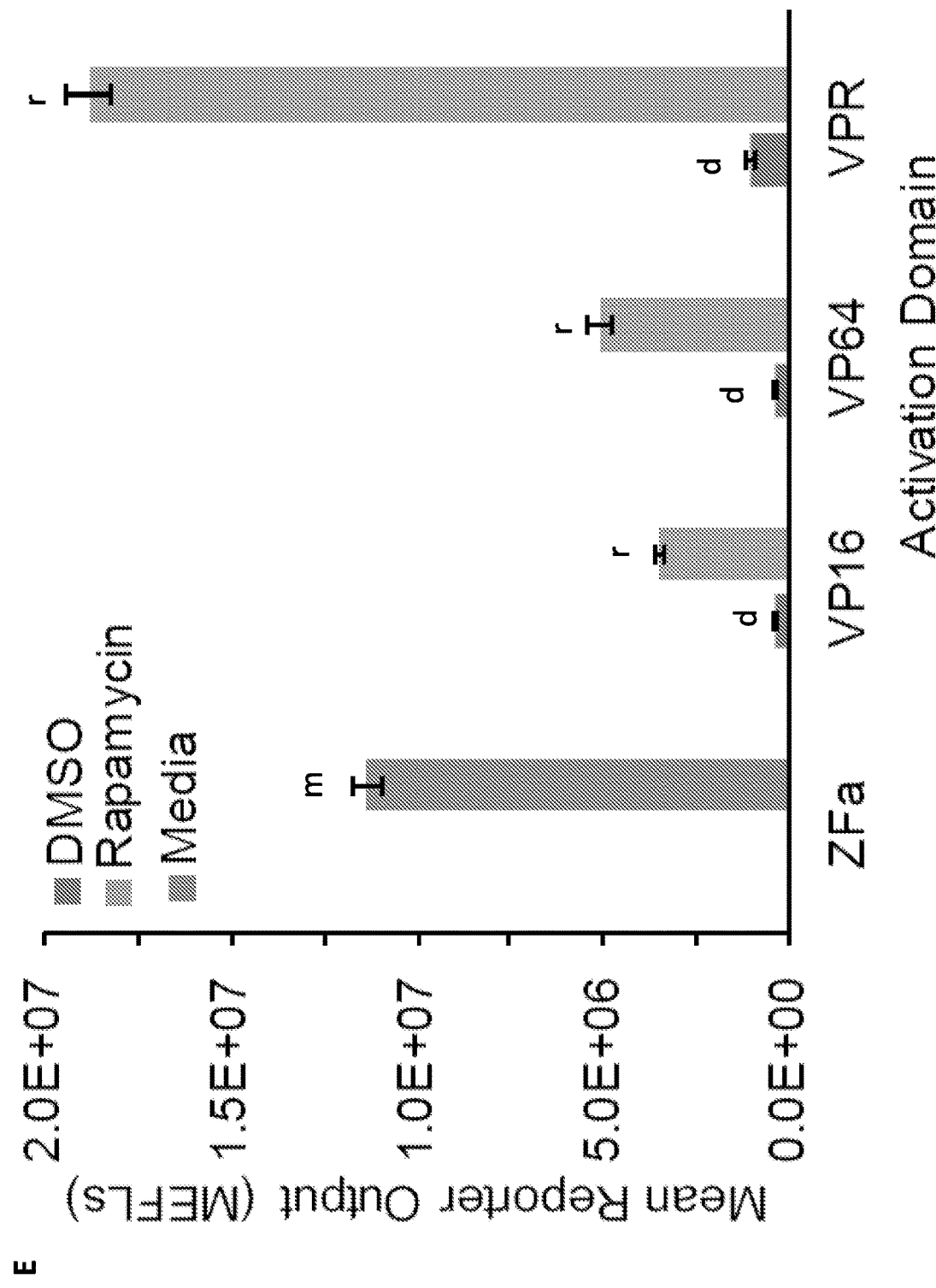

Ratios of FBKP-ZF and AD-FRB on RaZF Performance. We also studied the effect of ratios of FBKP-ZF and AD-FRB on performance of VP64 based RaZF (FIG. 13C) and VPR based RaZF (FIG. 13D). Ratios of FBKP-ZF and AD-FRB for the RaZF based on VP64 and VPR were studied. In both cases, performance could not be improved by decreasing the dose of FKBP-ZF and then increasing the dose of AD-FRB, unlike for the VP16 based RaZF examined earlier. In FIG. 13E, performance of VP16-based RaZF, VP64-based RaZf, and VPR-based RaZF were compared with all components expressed at a 1:5 FKBP-ZF:AD-FRB ratio, using 20 ng of the FKBP-ZF.

Figure 14:
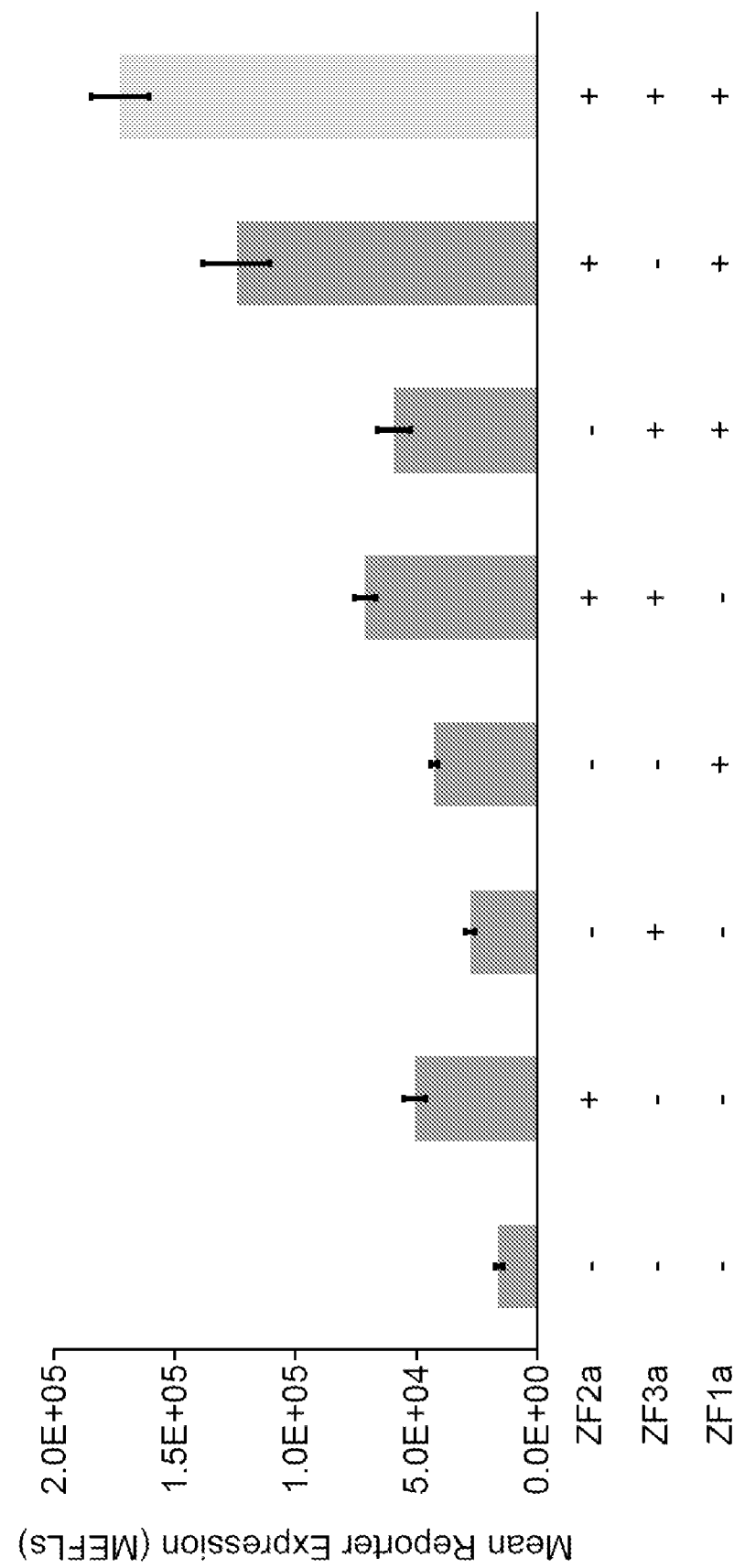
FIG. 14. Multiple-input AND Gates. (A) Three-input AND gate with one motif repeat. (B) Four-input gate with two ZFa and two ZFi-dsRed. (C) Effect of increasing doses of ZF1i-dsRed.
Figure 14:
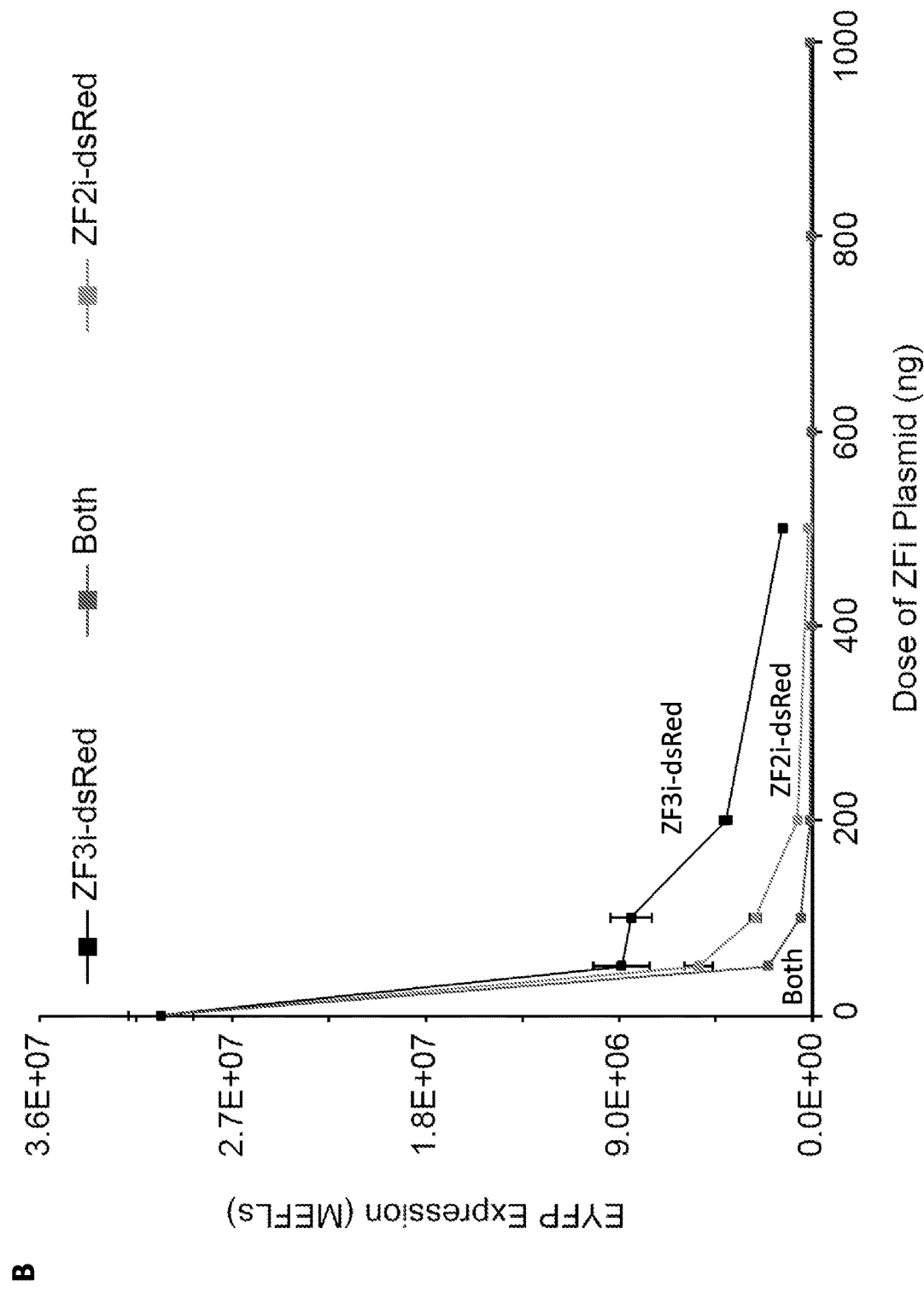
Figure 14:
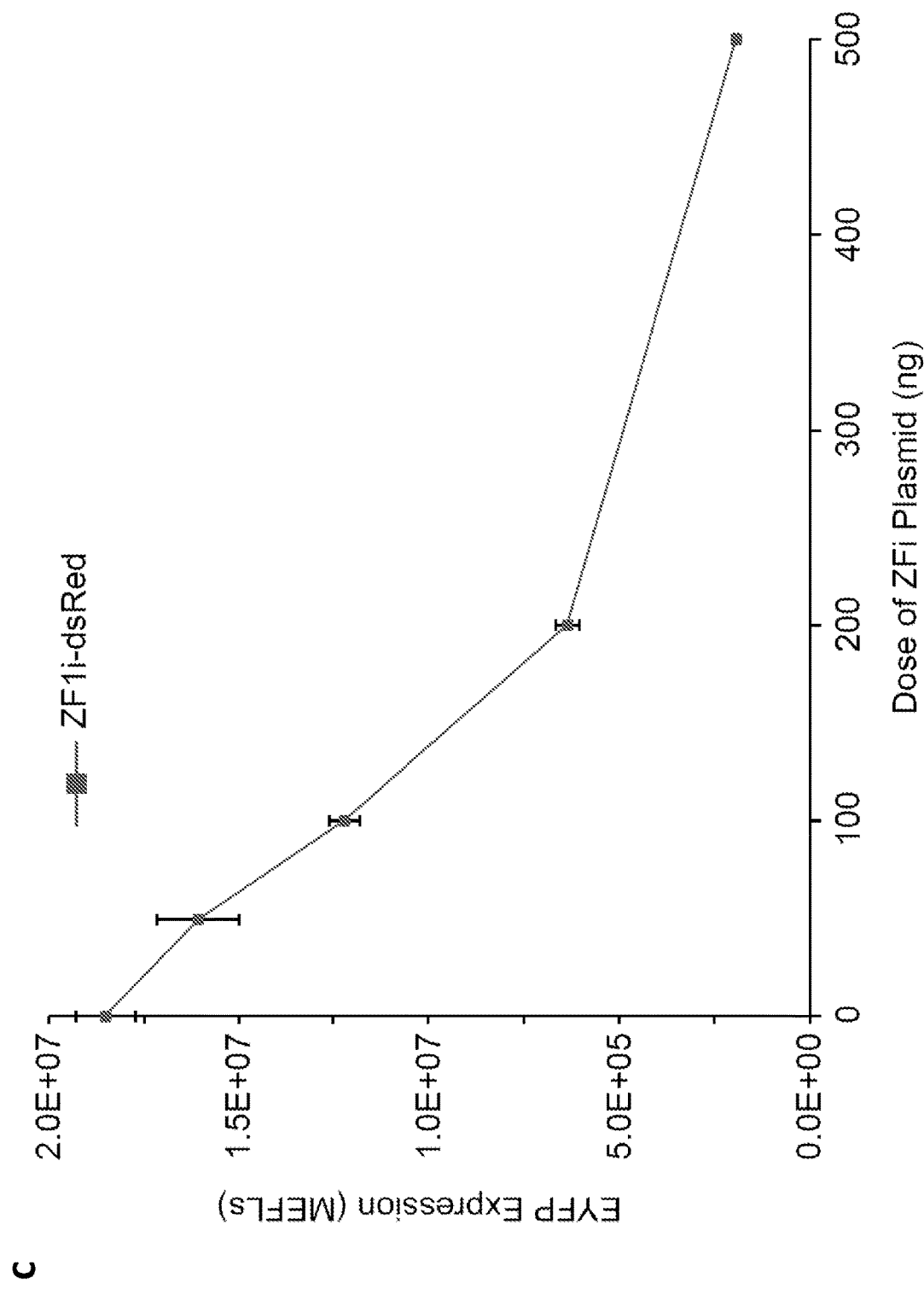

Exemplary Three Input AND Gate. FIG. 14A illustrates the results of a three-input AND gate with one motif repeat. Cells were transfected with the reporter, with a 1 repeat of the 3 binding site promoter (1 each of ZF1, ZF2, and ZF3) and combinations of ZFa. The promoter did not produce high expression even in the presence of all three ZFa.

Exemplary Four Input AND Gate. FIG. 14B and FIG. 14C illustrate a four-input gate with two ZFa and two ZFi-dsRed. Cells were transfected with the three-repeat hybrid promoter, for ZF2, and ZF3. This promoter also utilized the strategy wherein ZF1 binding sites in the linker regions overlap with the ZF2 binding sites. Increasing doses of ZF2-dsRed and ZF3-dsRed (or both) were able to inhibit the AND gate (FIG. 14B), while increasing doses of ZF1i-dsRed resulted in only mild inhibition (FIG. 14C).

Gene Expression Cascades and Programs. By placing the expression of one ZFa under the control of a second ZFa, we demonstrated that sequential activation is possible, to create a gene expression cascade or program.

Cell-based biosensors. We demonstrated ZFa could be integrated into our previously published engineered biosensor platform (MESA (Daringer et al., 2014)), such that triggering the MESA biosensor releases a ZFa to control expression of the output gene.

REFERENCES

Khalil et al. "A synthetic biology framework for programming eukaryotic transcription functions," Cell, 2012.

Hansen et al., "Transplantation of prokaryotic two-component signaling pathways into mammalian cells," PNAS, 2014.

Daringer et al., "Modular Extracellular Sensor Architecture for Engineering Mammalian Cell-based Devices," ACS Synthetic Biology, 2014.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A modular transcription system effective to modulate transcription in mammalian cells, the system comprising:
  (a) one or more engineered proteins selected from the group consisting of:
    (i) an engineered protein that activates gene expression, the engineered protein comprising a zinc finger DNA binding domain with three zinc fingers and a transcription activator domain;
    (ii) an engineered protein that inhibits gene expression, the engineered protein comprising a zinc finger DNA binding domain with three zinc fingers and a transcription inhibitor domain;
    (iii) a combination that activates gene expression, where the combination comprises two engineered proteins comprising a first engineered protein comprising a zinc finger DNA binding domain with three zinc fingers fused to a dimerization domain, and a second engineered protein comprising a transcription activator domain fused to a dimerization domain, wherein the dimerization domains of the two engineered proteins dimerize in the presence of a ligand to which the dimerization domains of the two engineered proteins bind;

(iv) a combination that inhibits gene expression, where the combination comprises two engineered proteins comprising a first engineered protein comprising a zinc finger DNA binding domain with three zinc fingers fused to a dimerization domain, and a second engineered protein comprising a transcription inhibitor domain fused to a dimerization domain, wherein the dimerization domains of the two engineered proteins dimerize in the presence of a ligand to which the dimerization domains of the two engineered proteins bind; and (b) one or more engineered expression vectors, the vectors comprising a minimal promoter and one or more DNA binding sites for the zinc finger DNA binding domains of the engineered proteins of (i), (ii), (iii) and/or (iv), and optionally a gene of interest that is expressed from the minimal promoter.

2. The modular transcription system of claim 1 comprising the engineered protein of (i) and the engineered protein of (ii).

3. The modular transcription system of claim 1, wherein the engineered proteins are fusion proteins comprising heterologous domains.

4. The modular transcription system of claim 1, wherein the transcription activator domain of the engineered protein of (i) comprises a domain from a transcription activator selected from the group consisting of Herpes simplex virus protein 16 (VP16), a synthetic tetramer of VP16 (VP64), nuclear factor (NF) kappa-B (p65), heat shock transcription factor 1 (HSF1), and replication and transcription activator (RTA) of the gamma-herpesvirus family.

5. The modular transcription system of claim 1, wherein the engineered protein of (ii) inhibits activation of transcription by the engineered protein of (i).

6. The modular transcription system of claim 1, wherein the transcription activator domain of the second engineered protein of the combination of engineered proteins of (iii) is selected from the group consisting of Herpes simplex virus protein 16 (VP16), a synthetic tetramer of VP16 (VP64), nuclear factor (NF) kappa-B (p65), heat shock transcription factor 1 (HSF1), and replication and transcription activator (RTA) of the gamma-herpesvirus family.

7. The modular transcription system of claim 1, comprising:

(a) a first engineered protein that activates gene expression, the first engineered protein comprising a first zinc finger DNA binding domain with three zinc fingers and a transcription activator domain;

(b) a first engineered expression vector comprising a minimal promoter and first DNA binding sites for the first zinc finger DNA binding domain with three zinc fingers of the first engineered protein, and a first gene of interest that is expressed from the minimal promoter, wherein the gene of interest encodes a second engineered protein, the second engineered protein comprising a second zinc finger DNA binding domain with three zinc fingers and a transcription activator domain; and (c) a second engineered expression vector comprising a minimal promoter and second DNA binding sites for the second zinc finger DNA binding domain with three zinc fingers of the engineered protein, and a second gene of interest that is expressed from the minimal promoter, wherein the second gene of interest encodes a detectable reporter protein;

wherein the first engineered protein increases expression from the first engineered expression vector and the second engineered protein increases expression from the second engineered vector.

8. The modular transcription system of claim 1, wherein at least one of the one or more engineered expression vectors comprises two or more of the DNA binding sites, spaced apart from each other by one or more spacers.

9. The modular transcription system of claim 8, where at least one spacer has a length of five to seven base pairs.

10. The modular transcription system of claim 9, where at least one spacer has a length of six base pairs.

11. The modular transcription system of claim 8, where each spacer has a length of five to seven base pairs.

12. The modular transcription system of claim 11, where each spacer has a length of six base pairs.

13. The modular transcription system of claim 8 wherein at least one of the one or more engineered expression vectors of (b) comprises at least six and no more than eight DNA binding sites.

14. The modular transcription system of claim 11, wherein at least one of the one or more engineered expression vectors of (b) has six DNA binding sites.

15. The modular transcription system of claim 1, wherein the minimal promoter of the one or more engineered expression vectors of (b) is a YB_TATA minimal promoter.

16. The modular transcription system of claim 1, wherein the one or more DNA binding sites of the one or more engineered expression vectors of (b) are located at a position not more than about 117 base pairs upstream of the minimal promoter.

17. The modular transcription system of claim 16, wherein the one or more DNA binding sites of the one or more engineered expression vectors of (b) are located at a position not more than about 33 base pairs upstream of the minimal promoter.

18. The modular transcription system of claim 16, wherein at least one of the one or more engineered expression vectors of (b) comprises at least four DNA binding sites.

19. The modular transcription system of claim 16, wherein at least one of the one or more engineered expression vectors of (b) comprises at least eight DNA binding sites.

20. The modular transcription system of claim 16, wherein at least one of the one or more engineered expression vectors of (b) comprises at least twelve DNA binding sites.

* * * * *